(12) United States Patent
Lau et al.

(10) Patent No.: US 12,702,515 B2
(45) Date of Patent: Aug. 11, 2026

(54) DRAPE FOR ARMS OF A ROBOTIC SURGICAL SYSTEM

(71) Applicant: Auris Health, Inc., Redwood City, CA (US)

(72) Inventors: Kandice H. Lau, Mountain View, CA (US); Benjamin L. Smith, Sunnyvale, CA (US)

(73) Assignee: Auris Health, Inc., Santa Clara, CA (US)

( * ) Notice: Subject to any disclaimer, the term of this patent is extended or adjusted under 35 U.S.C. 154(b) by 1339 days.

(21) Appl. No.: 17/094,578

(22) Filed: Nov. 10, 2020

(65) Prior Publication Data

US 2021/0153966 A1 May 27, 2021

Related U.S. Application Data

(60) Provisional application No. 62/938,648, filed on Nov. 21, 2019.

(51) Int. Cl.
*A61B 46/10* (2016.01)
*A61B 34/30* (2016.01)

(52) U.S. Cl.
CPC .............. *A61B 46/10* (2016.02); *A61B 34/30* (2016.02)

(58) Field of Classification Search
CPC ......... A61B 46/00; A61B 46/10; A61B 46/23; A61B 46/27; A61B 46/40; A61B 34/30; A61B 2034/301; A61B 5/062; A61B 2017/00477; A61B 50/13; A61B 50/00
USPC ......................................... 128/849, 855, 856
See application file for complete search history.

(56) References Cited

U.S. PATENT DOCUMENTS

| | | | |
|---|---|---|---|
| 3,528,720 | A | 9/1970 | Treace |
| 3,763,860 | A | 10/1973 | Clarke |
| 4,040,413 | A | 8/1977 | Ohshiro |
| 4,198,960 | A | 4/1980 | Utsugi |
| 4,470,407 | A | 9/1984 | Hussein |
| 4,532,935 | A | 8/1985 | Wang et al. |
| 4,685,458 | A | 8/1987 | Leckrone |
| 4,747,405 | A | 5/1988 | Leckrone |
| 4,854,301 | A | 8/1989 | Nakajima |
| 4,898,574 | A | 2/1990 | Uchiyama et al. |
| 4,983,165 | A | 1/1991 | Loiterman |

(Continued)

FOREIGN PATENT DOCUMENTS

| | | |
|---|---|---|
| CN | 101443069 | 5/2009 |
| CN | 100515347 | 7/2009 |

(Continued)

OTHER PUBLICATIONS

KR 2011057108 A machine translation (Year: 2011).*

(Continued)

*Primary Examiner* — Caitlin A Carreiro
(74) *Attorney, Agent, or Firm* — FBT GIBBONS LLP

(57) ABSTRACT

Certain aspects relate to systems and techniques for an assembly for draping two or more robotic arms of a robotic surgical system. In one aspect, the system includes a first tube including a first pocket for receiving a first robotic arm. The first tube can be configured to be downwardly draped over the first arm. The system may include a second tube including a second pocket for receiving a second robotic arm. The second tube can be configured to be downwardly draped over the second arm.

18 Claims, 51 Drawing Sheets

(56) References Cited

U.S. PATENT DOCUMENTS 5,029,574 A 7/1991 Shimamura et al.
5,085,659 A 2/1992 Rydell
5,150,452 A 9/1992 Pollack et al.
5,196,023 A 3/1993 Martin
5,217,465 A 6/1993 Steppe
5,308,323 A 5/1994 Sogawa et al.
5,318,589 A 6/1994 Lichtman
5,325,848 A 7/1994 Adams et al.
5,342,381 A 8/1994 Tidemand
5,344,395 A 9/1994 Whalen et al.
5,353,783 A 10/1994 Nakao et al.
5,370,609 A 12/1994 Drasler et al.
5,372,124 A 12/1994 Takayama et al.
5,411,016 A 5/1995 Kume
5,431,649 A 7/1995 Mulier et al.
5,441,485 A 8/1995 Peters
5,449,356 A 9/1995 Walbrink
5,450,843 A 9/1995 Moll et al.
5,472,426 A 12/1995 Bonati et al.
5,496,267 A 3/1996 Drasler
5,501,667 A 3/1996 Verduin, Jr.
5,520,684 A 5/1996 Imran
5,545,170 A 8/1996 Hart
5,562,239 A 10/1996 Boiarski et al.
5,562,648 A 10/1996 Peterson
5,562,678 A 10/1996 Booker
5,572,999 A 11/1996 Funda et al.
5,573,535 A 11/1996 Viklund
5,613,973 A 3/1997 Jackson et al.
5,645,083 A 7/1997 Essig et al.
5,653,374 A 8/1997 Young et al.
5,658,311 A 8/1997 Baden
5,695,500 A 12/1997 Taylor et al.
5,697,949 A 12/1997 Giurtino et al.
5,710,870 A 1/1998 Ohm
5,716,325 A 2/1998 Bonutti
5,737,500 A 4/1998 Seraji et al.
5,788,667 A 8/1998 Stoller
5,792,165 A 8/1998 Klieman
5,797,900 A 8/1998 Madhani
5,798,627 A 8/1998 Gilliland
5,810,770 A 9/1998 Chin et al.
5,893,869 A 4/1999 Barnhart
5,897,491 A 4/1999 Kastenbauer et al.
5,924,175 A 7/1999 Lippitt
5,943,056 A 8/1999 Sato
5,989,230 A 11/1999 Frassica
6,071,281 A 6/2000 Burnside et al.
6,093,157 A 7/2000 Chandrasekaran
6,110,171 A 8/2000 Rydell
6,120,476 A 9/2000 Fung et al.
6,120,498 A 9/2000 Jani et al.
6,156,030 A 12/2000 Neev
6,174,318 B1 1/2001 Bates et al.
6,183,435 B1 2/2001 Bumbalough et al.
6,206,903 B1 3/2001 Ramans
6,236,906 B1 5/2001 Muller
6,322,557 B1 11/2001 Nikolaevich
6,375,635 B1 4/2002 Moutafis
6,394,998 B1 5/2002 Wallace et al.
6,405,078 B1 6/2002 Moaddeb et al.
6,440,061 B1 8/2002 Wenner et al.
6,508,823 B1 1/2003 Gonon
6,522,906 B1 2/2003 Salisbury et al.
6,577,891 B1 6/2003 Jaross et al.
6,676,668 B2 1/2004 Mercereau et al.
6,685,698 B2 2/2004 Morley et al.
6,706,050 B1 3/2004 Giannadakis
6,718,994 B2 4/2004 Lewis
7,282,055 B2 10/2007 Tsuruta
7,559,934 B2 7/2009 Teague et al.
7,727,244 B2 6/2010 Orban, III et al.
7,736,356 B2 6/2010 Cooper et al.
7,963,911 B2 6/2011 Turliuc
7,987,046 B1 7/2011 Peterman
8,002,713 B2 8/2011 Heske
8,004,229 B2 8/2011 Nowlin et al.
8,038,598 B2 10/2011 Khachi
8,092,397 B2 1/2012 Wallace et al.
8,105,338 B2 1/2012 Anderson et al.
8,187,173 B2 5/2012 Miyoshi
8,202,278 B2 6/2012 Orban, III et al.
8,257,303 B2 9/2012 Moll et al.
8,480,595 B2 7/2013 Speeg
8,523,762 B2 9/2013 Miyamoto et al.
8,540,748 B2 9/2013 Murphy et al.
8,541,970 B2 9/2013 Nowlin
8,746,252 B2 6/2014 McGrogan et al.
8,749,190 B2 6/2014 Nowlin et al.
8,786,241 B2 7/2014 Nowlin et al.
8,820,603 B2 9/2014 Shelton et al.
8,821,480 B2 9/2014 Burbank
8,882,660 B2 11/2014 Phee et al.
8,945,163 B2 2/2015 Voegele et al.
8,956,280 B2 2/2015 Eversull et al.
9,096,033 B2 8/2015 Holop et al.
9,179,979 B2 11/2015 Jinno
9,259,282 B2 2/2016 Azizian
9,296,104 B2 3/2016 Swarup et al.
9,320,568 B2 4/2016 Orban, III et al.
9,345,456 B2 5/2016 Tsonton et al.
9,345,544 B2 5/2016 Hourtash et al.
9,375,284 B2 6/2016 Hourtash
9,415,510 B2 8/2016 Hourtash et al.
9,460,536 B2 10/2016 Hasegawa et al.
9,480,534 B2 11/2016 Bowling
9,504,604 B2 11/2016 Alvarez
9,510,911 B2 12/2016 Hourtash
9,517,106 B2 12/2016 Hourtash et al.
9,561,083 B2 2/2017 Yu et al.
9,566,125 B2 2/2017 Bowling
9,592,042 B2 3/2017 Titus
9,597,152 B2 3/2017 Schaeffer
9,622,827 B2 4/2017 Yu et al.
9,636,184 B2 5/2017 Lee et al.
9,675,422 B2 6/2017 Hourtash et al.
9,687,310 B2 6/2017 Nowlin et al.
9,713,509 B2 7/2017 Schuh et al.
9,727,963 B2 8/2017 Mintz et al.
9,730,757 B2 8/2017 Brudniok
9,737,371 B2 8/2017 Romo et al.
9,737,373 B2 8/2017 Schuh
9,744,335 B2 8/2017 Jiang
9,763,741 B2 9/2017 Alvarez et al.
9,788,910 B2 10/2017 Schuh
9,844,412 B2 12/2017 Bogusky et al.
9,867,635 B2 1/2018 Alvarez et al.
9,918,681 B2 3/2018 Wallace et al.
9,931,025 B1 4/2018 Graetzel et al.
9,943,962 B2 4/2018 Sattler et al.
9,949,749 B2 4/2018 Noonan et al.
9,955,986 B2 5/2018 Shah
9,962,228 B2 5/2018 Schuh et al.
9,980,785 B2 5/2018 Schuh
9,993,313 B2 6/2018 Schuh et al.
10,016,900 B1 7/2018 Meyer et al.
10,022,192 B1 7/2018 Ummalaneni
10,029,367 B2 7/2018 Hourtash
10,071,479 B2 9/2018 Swarup et al.
10,080,576 B2 9/2018 Romo et al.
10,117,713 B2 11/2018 Moctezuma de la Barrera
10,130,429 B1 11/2018 Weir
10,136,949 B2 11/2018 Felder et al.
10,136,959 B2 11/2018 Mintz et al.
10,145,747 B1 12/2018 Lin et al.
10,149,720 B2 12/2018 Romo
10,154,822 B2 12/2018 Henderson
10,159,532 B1 12/2018 Ummalaneni et al.
10,159,533 B2 12/2018 Moll et al.
10,169,875 B2 1/2019 Mintz et al.
10,219,868 B2 3/2019 Weir
10,219,874 B2 3/2019 Yu et al.
10,231,793 B2 3/2019 Romo
10,231,867 B2 3/2019 Alvarez et al.

(56) References Cited

U.S. PATENT DOCUMENTS 10,244,926 B2 4/2019 Noonan et al.
10,285,574 B2 5/2019 Landey et al.
10,299,870 B2 5/2019 Connolly et al.
10,314,463 B2 6/2019 Agrawal et al.
10,314,661 B2 6/2019 Bowling
10,327,855 B2 6/2019 Hourtash et al.
10,350,017 B2 7/2019 Bowling
10,350,390 B2 7/2019 Moll et al.
10,383,765 B2 8/2019 Alvarez et al.
10,398,518 B2 9/2019 Yu et al.
10,405,939 B2 9/2019 Romo et al.
10,405,940 B2 9/2019 Romo
10,426,559 B2 10/2019 Graetzel et al.
10,426,661 B2 10/2019 Kintz
10,434,660 B2 10/2019 Meyer
10,463,440 B2 11/2019 Bowling
10,464,209 B2 11/2019 Ho et al.
10,470,830 B2 11/2019 Hill
10,482,599 B2 11/2019 Mintz et al.
10,493,241 B2 12/2019 Jiang
10,500,001 B2 12/2019 Yu et al.
10,517,692 B2 12/2019 Eyre et al.
10,524,866 B2 1/2020 Srinivasan
10,539,478 B2 1/2020 Lin
10,543,048 B2 1/2020 Noonan et al.
10,555,778 B2 2/2020 Ummalaneni et al.
10,631,949 B2 4/2020 Schuh et al.
10,639,108 B2 5/2020 Romo et al.
10,639,109 B2 5/2020 Bovay et al.
10,639,114 B2 5/2020 Schuh
10,667,871 B2 6/2020 Romo et al.
10,667,875 B2 6/2020 DeFonzo
10,682,189 B2 6/2020 Schuh et al.
10,702,348 B2 7/2020 Moll et al.
10,716,461 B2 7/2020 Jenkins
10,743,751 B2 8/2020 Landey et al.
10,744,035 B2 8/2020 Alvarez et al.
10,751,140 B2 8/2020 Wallace et al.
10,765,303 B2 9/2020 Graetzel et al.
10,765,487 B2 9/2020 Ho
10,779,898 B2 9/2020 Hill
10,786,329 B2 9/2020 Schuh et al.
10,786,432 B2 9/2020 Jornitz et al.
10,792,464 B2 10/2020 Romo et al.
10,792,466 B2 10/2020 Landey et al.
10,813,539 B2 10/2020 Graetzel et al.
10,814,101 B2 10/2020 Jiang
10,820,947 B2 11/2020 Julian
10,820,954 B2 11/2020 Marsot et al.
10,827,913 B2 11/2020 Ummalaneni et al.
10,828,118 B2 11/2020 Schuh et al.
10,835,153 B2 11/2020 Rafii-Tari et al.
10,842,581 B2 11/2020 Bailey
10,850,013 B2 12/2020 Hsu
12,357,409 B2 7/2025 Lau et al.
2002/0019644 A1 2/2002 Hastings
2002/0111608 A1 8/2002 Baerveldt
2002/0111621 A1 8/2002 Wallace et al.
2003/0004455 A1 1/2003 Kadziauskas
2003/0040681 A1 2/2003 Ng et al.
2003/0065358 A1 4/2003 Frecker
2003/0100892 A1 5/2003 Morley et al.
2003/0109780 A1 6/2003 Coste-Maniere et al.
2003/0109877 A1 6/2003 Morley
2003/0109889 A1 6/2003 Mercereau
2003/0158545 A1 8/2003 Hovda et al.
2003/0208189 A1 11/2003 Payman
2004/0143253 A1 7/2004 Vanney
2004/0153093 A1 8/2004 Donovan
2004/0158261 A1 8/2004 Vu
2004/0186349 A1 9/2004 Ewers
2004/0193146 A1 9/2004 Lee et al.
2004/0210116 A1 10/2004 Nakao
2004/0253079 A1 12/2004 Sanchez
2005/0033270 A1 2/2005 Ramans et al.
2005/0054900 A1 3/2005 Mawn
2005/0159645 A1 7/2005 Bertolero
2005/0240178 A1 10/2005 Morley et al.
2005/0261705 A1 11/2005 Gist
2006/0015133 A1 1/2006 Grayzel
2006/0058813 A1 3/2006 Teague
2006/0116693 A1 6/2006 Weisenburgh
2006/0135963 A1 6/2006 Kick
2006/0150987 A1 7/2006 Dillon et al.
2006/0156875 A1 7/2006 McRury et al.
2006/0161137 A1 7/2006 Orban et al.
2006/0189891 A1 8/2006 Waxman et al.
2007/0016164 A1 1/2007 Dudney et al.
2007/0027443 A1 2/2007 Rose
2007/0027534 A1 2/2007 Bergheim
2007/0032906 A1 2/2007 Sutherland et al.
2007/0106304 A1 5/2007 Hammack
2007/0123855 A1 5/2007 Morley et al.
2007/0135803 A1 6/2007 Belson
2007/0208375 A1 9/2007 Nishizawa
2007/0213668 A1 9/2007 Spitz
2007/0239178 A1 10/2007 Weitzner et al.
2007/0250111 A1 10/2007 Lu
2007/0299427 A1 12/2007 Yeung et al.
2008/0015566 A1 1/2008 Livneh
2008/0021440 A1 1/2008 Solomon
2008/0033467 A1 2/2008 Miyamoto et al.
2008/0045981 A1 2/2008 Margolin et al.
2008/0046122 A1 2/2008 Manzo et al.
2008/0065111 A1 3/2008 Blumenkranz
2008/0065112 A1 3/2008 Tovey et al.
2008/0125698 A1 5/2008 Greg et al.
2008/0187101 A1 8/2008 Gertner
2008/0196533 A1 8/2008 Bergamasco
2008/0228104 A1 9/2008 Uber et al.
2009/0012507 A1 1/2009 Culbertson et al.
2009/0030446 A1 1/2009 Measamer
2009/0036900 A1 2/2009 Moll
2009/0043305 A1 2/2009 Brodbeck
2009/0082634 A1 3/2009 Kathrani et al.
2009/0088774 A1 4/2009 Swarup et al.
2009/0105723 A1 4/2009 Dillinger
2009/0131885 A1 5/2009 Akahoshi
2009/0161827 A1 6/2009 Gertner et al.
2009/0192524 A1 7/2009 Ltkowitz
2009/0227998 A1 9/2009 Aljuri
2009/0248041 A1 10/2009 Williams et al.
2009/0248043 A1 10/2009 Tierney et al.
2009/0264878 A1 10/2009 Carmel et al.
2009/0270760 A1 10/2009 Leimbach et al.
2009/0287188 A1 11/2009 Golden et al.
2009/0299352 A1 12/2009 Zerfas
2009/0312773 A1 12/2009 Cabrera et al.
2010/0004642 A1 1/2010 Lumpkin
2010/0010504 A1 1/2010 Simaan et al.
2010/0011900 A1 1/2010 Burbank
2010/0011901 A1 1/2010 Burbank
2010/0016852 A1 1/2010 Manzo et al.
2010/0016853 A1 1/2010 Burbank
2010/0081965 A1 4/2010 Mugan et al.
2010/0082017 A1 4/2010 Zickler
2010/0179632 A1 7/2010 Bruszewski et al.
2010/0204605 A1 8/2010 Blakley
2010/0204646 A1 8/2010 Plicchi et al.
2010/0217235 A1 8/2010 Thorstenson
2010/0225209 A1 9/2010 Goldberg
2010/0228249 A1 9/2010 Mohr
2010/0268211 A1 10/2010 Manwaring et al.
2010/0312141 A1 12/2010 Keast et al.
2010/0331858 A1 12/2010 Simaan et al.
2011/0015483 A1 1/2011 Barbagli
2011/0028790 A1 2/2011 Farr et al.
2011/0071541 A1 3/2011 Prisco et al.
2011/0071543 A1 3/2011 Prisco et al.
2011/0106146 A1 5/2011 Jeong
2011/0125165 A1 5/2011 Simaan et al.
2011/0152880 A1 6/2011 Alvarez et al.
2011/0160713 A1 6/2011 Neuberger
2011/0160745 A1 6/2011 Fielding

(56) References Cited

U.S. PATENT DOCUMENTS

2011/0167611 A1 7/2011 Williams
2011/0208211 A1 8/2011 Whitfield et al.
2011/0213362 A1 9/2011 Cunningham
2011/0224660 A1 9/2011 Neuberger et al.
2011/0238064 A1 9/2011 Williams et al.
2011/0257641 A1 10/2011 Hastings et al.
2011/0276085 A1 11/2011 Krzyzanowski
2011/0313343 A1 12/2011 Milutinovic et al.
2012/0048759 A1 3/2012 Disch et al.
2012/0069167 A1 3/2012 Llu et al.
2012/0138586 A1 6/2012 Webster et al.
2012/0138660 A1 6/2012 Shelton, IV et al.
2012/0209315 A1 8/2012 Amat
2012/0232342 A1 9/2012 Reydel
2012/0253277 A1 10/2012 Tah et al.
2012/0253332 A1 10/2012 Moll
2012/0259320 A1 10/2012 Loesel et al.
2012/0296318 A1 11/2012 Wellhofer et al.
2013/0006144 A1 1/2013 Clancy
2013/0035537 A1 2/2013 Wallace et al.
2013/0053877 A1 2/2013 BenMaamer
2013/0066136 A1 3/2013 Palese et al.
2013/0085442 A1 4/2013 Shtul et al.
2013/0085486 A1 4/2013 Boutoussov et al.
2013/0096422 A1 4/2013 Boctor
2013/0096574 A1 4/2013 Kang et al.
2013/0110042 A1 5/2013 Humphreys
2013/0110107 A1 5/2013 Smith et al.
2013/0116716 A1 5/2013 Bahls et al.
2013/0144274 A1 6/2013 Stefanchik et al.
2013/0144395 A1 6/2013 Stefanchik
2013/0190796 A1 7/2013 Tilson et al.
2013/0225997 A1 8/2013 Dillard et al.
2013/0226161 A1 8/2013 Hickenbotham
2013/0233908 A1 9/2013 Knodel
2013/0253267 A1 9/2013 Collins
2013/0303876 A1 11/2013 Gelfand et al.
2013/0310819 A1 11/2013 Neuberger et al.
2013/0317519 A1 11/2013 Romo et al.
2013/0329291 A1 12/2013 Federle
2013/0334281 A1 12/2013 Williams
2013/0345686 A1 12/2013 Brown
2014/0005681 A1 1/2014 Gee et al.
2014/0039517 A1 2/2014 Bowling
2014/0039681 A1 2/2014 Bowling
2014/0046308 A1 2/2014 Bischoff
2014/0051985 A1 2/2014 Fan et al.
2014/0058365 A1 2/2014 Bille
2014/0058404 A1 2/2014 Hammack
2014/0058428 A1 2/2014 Christopher
2014/0100445 A1 4/2014 Stenzel
2014/0142591 A1 5/2014 Alvarez et al.
2014/0163318 A1 6/2014 Swanstrom
2014/0163736 A1 6/2014 Azizian
2014/0194859 A1 7/2014 Lanchulev
2014/0194905 A1 7/2014 Kappel
2014/0222207 A1 8/2014 Bowling et al.
2014/0243849 A1 8/2014 Saglam et al.
2014/0246473 A1 9/2014 Auld
2014/0257333 A1 9/2014 Blumenkranz
2014/0275956 A1 9/2014 Fan
2014/0276723 A1 9/2014 Parihar
2014/0276956 A1 9/2014 Crainich
2014/0309655 A1 10/2014 Gal et al.
2014/0316203 A1 10/2014 Carroux et al.
2014/0338676 A1* 11/2014 Marinchak ............ A61B 46/10 128/855
2014/0357984 A1 12/2014 Wallace et al.
2015/0073439 A1 3/2015 Dannaher
2015/0080879 A1 3/2015 Trees
2015/0127045 A1 5/2015 Prestel
2015/0133960 A1 5/2015 Lohmeier
2015/0150635 A1 6/2015 Kilroy
2015/0164522 A1 6/2015 Budiman
2015/0190204 A1 7/2015 Popovi
2015/0201917 A1 7/2015 Snow
2015/0202085 A1 7/2015 Lemonis
2015/0314110 A1 11/2015 Park
2015/0366629 A1 12/2015 Bowling
2015/0374446 A1 12/2015 Malackowski
2016/0008073 A1 1/2016 Pecora
2016/0022289 A1 1/2016 Wan
2016/0022466 A1 1/2016 Pedtke
2016/0030073 A1 2/2016 Lsakov
2016/0045208 A1 2/2016 Ciulla
2016/0051318 A1 2/2016 Manzo et al.
2016/0066935 A1 3/2016 Nguyen et al.
2016/0158490 A1 6/2016 Leeflang
2016/0166348 A1* 6/2016 Adams .................. A61B 46/13 156/247
2016/0183841 A1 6/2016 Duindam et al.
2016/0199984 A1 7/2016 Lohmeier et al.
2016/0235495 A1 8/2016 Wallace et al.
2016/0242858 A1 8/2016 Moctezuma de la Barrera et al.
2016/0249932 A1 9/2016 Rogers et al.
2016/0270865 A1 9/2016 Landey et al.
2016/0287279 A1 10/2016 Bovay et al.
2016/0296294 A1 10/2016 Moll et al.
2016/0302871 A1 10/2016 Gregerson et al.
2016/0303743 A1 10/2016 Rockrohr
2016/0310146 A1 10/2016 Levy et al.
2016/0331358 A1 11/2016 Gordon
2016/0361129 A1 12/2016 Morrissette et al.
2016/0367324 A1 12/2016 Sato et al.
2017/0000577 A1 1/2017 Bowling
2017/0007337 A1 1/2017 Dan
2017/0049471 A1 2/2017 Gaffney et al.
2017/0055995 A1 3/2017 Weier
2017/0065227 A1 3/2017 Marrs
2017/0071584 A1 3/2017 Suigetsu et al.
2017/0086934 A1* 3/2017 Devengenzo .......... A61B 46/10
2017/0095234 A1 4/2017 Prisco et al.
2017/0095295 A1 4/2017 Overmyer
2017/0135706 A1 5/2017 Frey
2017/0151416 A1 6/2017 Kutikov
2017/0165009 A1 6/2017 Chaplin et al.
2017/0172553 A1 6/2017 Chaplin
2017/0172680 A1 6/2017 Bowling
2017/0202627 A1 7/2017 Sramek et al.
2017/0209073 A1 7/2017 Sramek et al.
2017/0252096 A1 9/2017 Felder
2017/0258534 A1 9/2017 Hourtash et al.
2017/0265923 A1 9/2017 Privitera
2017/0265954 A1 9/2017 Burbank
2017/0290631 A1 10/2017 Lee et al.
2017/0319289 A1 11/2017 Neff et al.
2017/0333137 A1 11/2017 Roessler
2017/0333147 A1 11/2017 Bernstein
2018/0000563 A1 1/2018 Shanjani et al.
2018/0025666 A1 1/2018 Ho et al.
2018/0049824 A1 2/2018 Harris
2018/0079090 A1 3/2018 Koenig et al.
2018/0080841 A1 3/2018 Cordoba
2018/0110573 A1* 4/2018 Kostrzewski ........ B25J 15/0019
2018/0140371 A1 5/2018 Hares et al.
2018/0193049 A1 7/2018 Heck et al.
2018/0206931 A1 7/2018 Scheib
2018/0221038 A1 8/2018 Noonan et al.
2018/0221039 A1 8/2018 Shar
2018/0250085 A1 9/2018 Simi
2018/0279852 A1 10/2018 Rafil-Tari et al.
2018/0289431 A1 10/2018 Draper et al.
2018/0296285 A1 10/2018 Simi et al.
2018/0325499 A1 11/2018 Landey et al.
2018/0360435 A1 12/2018 Romo
2019/0000559 A1 1/2019 Berman et al.
2019/0000560 A1 1/2019 Berman et al.
2019/0000576 A1 1/2019 Mintz et al.
2019/0015166 A1 1/2019 Mahoney
2019/0069962 A1 3/2019 Tabandeh et al.
2019/0099231 A1 4/2019 Bruehwiler
2019/0099232 A1 4/2019 Soto et al.
2019/0110839 A1 4/2019 Rafii-Tari et al.
2019/0117320 A1 4/2019 Shoham et al.

(56) References Cited

U.S. PATENT DOCUMENTS

2019/0117324 A1 4/2019 Hibner
2019/0142540 A1* 5/2019 Chow .................... A61B 34/35 428/174
2019/0151148 A1 5/2019 Alvarez et al.
2019/0167366 A1 6/2019 Ummalaneni
2019/0175009 A1 6/2019 Mintz
2019/0183585 A1 6/2019 Rafil-Tari et al.
2019/0183587 A1 6/2019 Rafii-Tari et al.
2019/0192249 A1 6/2019 Bowling
2019/0216548 A1 7/2019 Ummalaneni
2019/0216576 A1 7/2019 Eyre
2019/0223969 A1 7/2019 Ramstad et al.
2019/0223974 A1 7/2019 Romo
2019/0231460 A1 8/2019 DiMaio
2019/0239890 A1 8/2019 Stokes
2019/0262086 A1 8/2019 Connolly et al.
2019/0269468 A1 9/2019 Hsu et al.
2019/0274764 A1 9/2019 Romo
2019/0290109 A1 9/2019 Agrawal et al.
2019/0298460 A1 10/2019 Al-Jadda
2019/0298464 A1 10/2019 Abbott
2019/0298465 A1 10/2019 Chin
2019/0298469 A1 10/2019 Ramstad et al.
2019/0298470 A1 10/2019 Ramstad et al.
2019/0314096 A1 10/2019 Diolaiti et al.
2019/0314616 A1 10/2019 Moll et al.
2019/0336238 A1 11/2019 Yu
2019/0365201 A1 12/2019 Noonan et al.
2019/0365209 A1 12/2019 Ye et al.
2019/0365479 A1 12/2019 Rafii-Tari
2019/0365486 A1 12/2019 Srinivasan et al.
2019/0375383 A1 12/2019 Alvarez
2019/0380787 A1 12/2019 Ye
2019/0380797 A1 12/2019 Yu
2020/0000533 A1 1/2020 Schuh
2020/0030046 A1 1/2020 Bowling
2020/0038123 A1 2/2020 Graetzel
2020/0039086 A1 2/2020 Meyer
2020/0046434 A1 2/2020 Graetzel
2020/0060516 A1 2/2020 Baez
2020/0085516 A1 3/2020 DeFonzo
2020/0093549 A1 3/2020 Chin
2020/0093554 A1 3/2020 Schuh
2020/0100855 A1 4/2020 Leparmentier
2020/0107894 A1 4/2020 Wallace
2020/0121502 A1 4/2020 Kintz
2020/0138531 A1 5/2020 Chaplin
2020/0146769 A1 5/2020 Eyre
2020/0163726 A1 5/2020 Tanner
2020/0170720 A1 6/2020 Ummalaneni
2020/0171660 A1 6/2020 Ho
2020/0188043 A1 6/2020 Yu
2020/0197109 A1 6/2020 Chaplin
2020/0197112 A1 6/2020 Chin
2020/0206472 A1 7/2020 Ma
2020/0217733 A1 7/2020 Lin
2020/0222134 A1 7/2020 Schuh
2020/0237458 A1 7/2020 DeFonzo
2020/0261172 A1 8/2020 Romo
2020/0268459 A1 8/2020 Noonan et al.
2020/0268460 A1 8/2020 Tse
2020/0281787 A1 9/2020 Ruiz
2020/0297437 A1 9/2020 Schuh
2020/0297444 A1 9/2020 Camarillo
2020/0305983 A1 10/2020 Yampolsky
2020/0305989 A1 10/2020 Schuh
2020/0305992 A1 10/2020 Schuh
2020/0315717 A1 10/2020 Bovay
2020/0315723 A1 10/2020 Hassan
2020/0323596 A1 10/2020 Moll
2020/0330167 A1 10/2020 Romo
2020/0345216 A1 11/2020 Jenkins
2020/0352420 A1 11/2020 Graetzel
2020/0360183 A1 11/2020 Alvarez
2020/0367726 A1 11/2020 Landey et al.
2020/0367981 A1 11/2020 Ho et al.
2020/0375678 A1 12/2020 Wallace
2021/0153965 A1 5/2021 Lua et al.

FOREIGN PATENT DOCUMENTS

CN 103298414 9/2013
CN 104619281 5/2015
CN 205729413 11/2016
EP 1 321 106 6/2003
EP 1 849 423 10/2007
EP 3281752 A1 2/2018
EP 3325234 B1 9/2020
JP 2005-270464 10/2005
KR 2011057108 A * 5/2011
KR 20110057108 A * 5/2011 ............. A61B 46/23
WO 2011/143023 A1 11/2011
WO WO 11/161218 12/2011
WO WO 13/107468 7/2013
WO WO 15/153174 10/2015
WO WO 16/137612 9/2016
WO WO 17/114855 7/2017
WO 2017/158263 A1 9/2017
WO WO 18/069679 4/2018
WO 2018/183794 A1 10/2018
WO WO 18/189722 10/2018
WO 2019/036004 A1 2/2019
WO 2019/150111 A1 8/2019

OTHER PUBLICATIONS

KR 20110057108 A machine translation (Year: 2011).*

Hernansanz et al, 2015, A multi-robot cooperation strategy for dexterous task oriented teleoperation, 2015, Elsevier, Robotics and Autonomous Systems, 68(205):156-172.

Ramezanifard et al, 2007, A Novel Modeling Approach for Collision Avoidance in Robotic Surgery, 2007 Science Publications, American Journal of Applied Sciences 4(9):693-699.

International Search Report and Written Opinion dated Feb. 1, 2021, for International Application No. PCT/IB2020/060587, 11 pages.

Chinese First Office Action and Search Report dated Aug. 6, 2025, for Application No. 202080080501.9, 7 pages.

European Communication dated May 7, 2025, for Application No. 20808517.5, 6 pages.

* cited by examiner 47
49
53
48
52
51
54
50

DRAPE FOR ARMS OF A ROBOTIC SURGICAL SYSTEM

CROSS-REFERENCE TO RELATED APPLICATION(S)

This application claims the benefit of U.S. Provisional Application No. 62/938,648, filed Nov. 21, 2019, which is hereby incorporated by reference in its entirety.

TECHNICAL FIELD

The systems and methods disclosed herein are directed to robotic surgical systems, and more particularly, to drapes for covering robotic surgical systems.

BACKGROUND

Medical procedures, such as endoscopy, may involve accessing and visualizing the inside of a patient's anatomy for diagnostic and/or therapeutic purposes. For example, gastroenterology, urology, and bronchology involve medical procedures that allow a physician to examine patient lumens, such as the ureter, gastrointestinal tract, and airways (bronchi and bronchioles). During these procedures, a tubular tool or instrument, e.g., an endoscope, may be inserted into the patient through an orifice (such as, e.g., a natural orifice) and advanced towards a tissue site for subsequent diagnosis and/or treatment. The medical instrument can be controlled and articulated by a robotic arm to facilitate navigation of the medical instrument through the anatomy.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
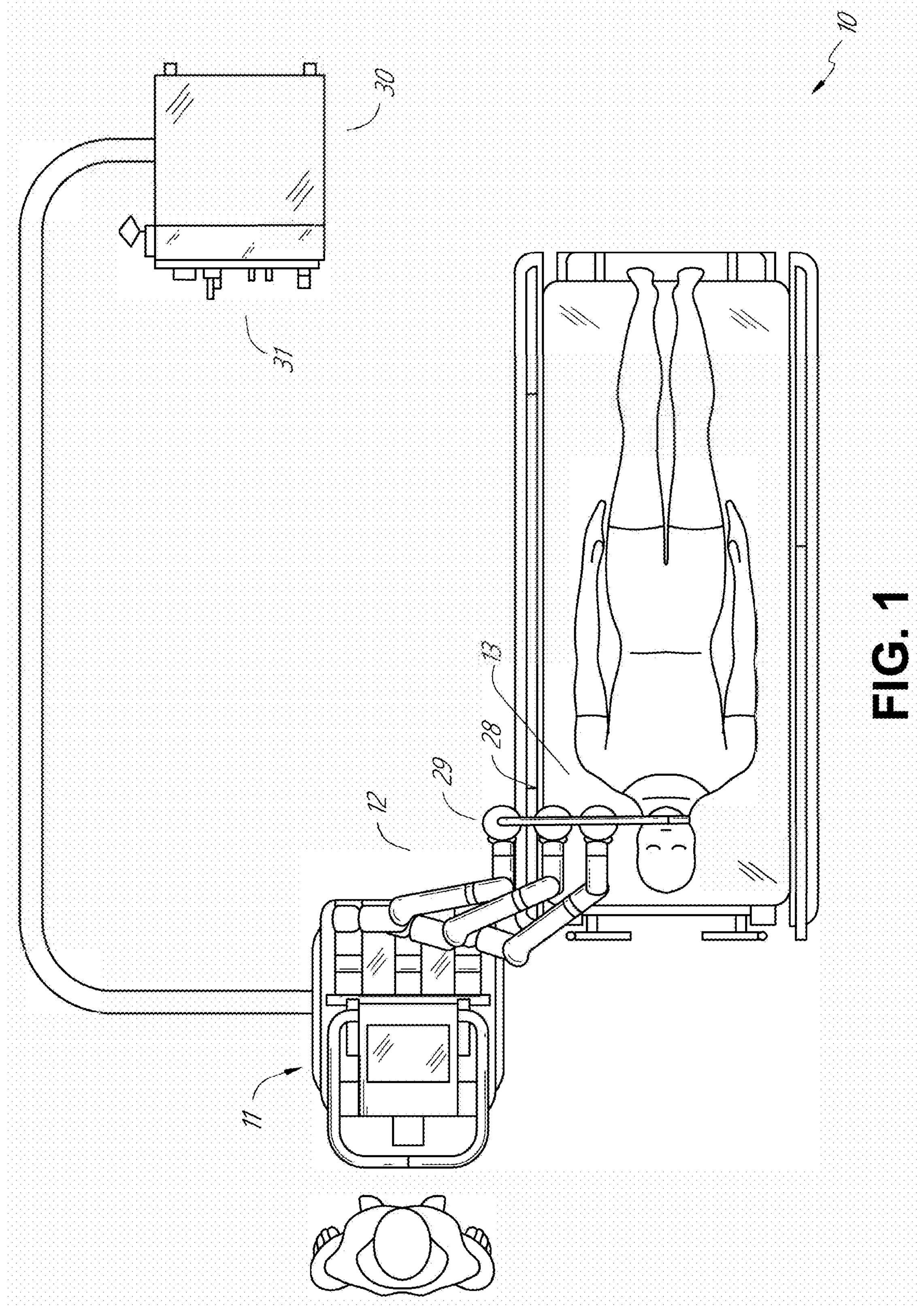
FIG. 1 illustrates an embodiment of a cart-based robotic system arranged for diagnostic and/or therapeutic bronchoscopy.
Figure 2:
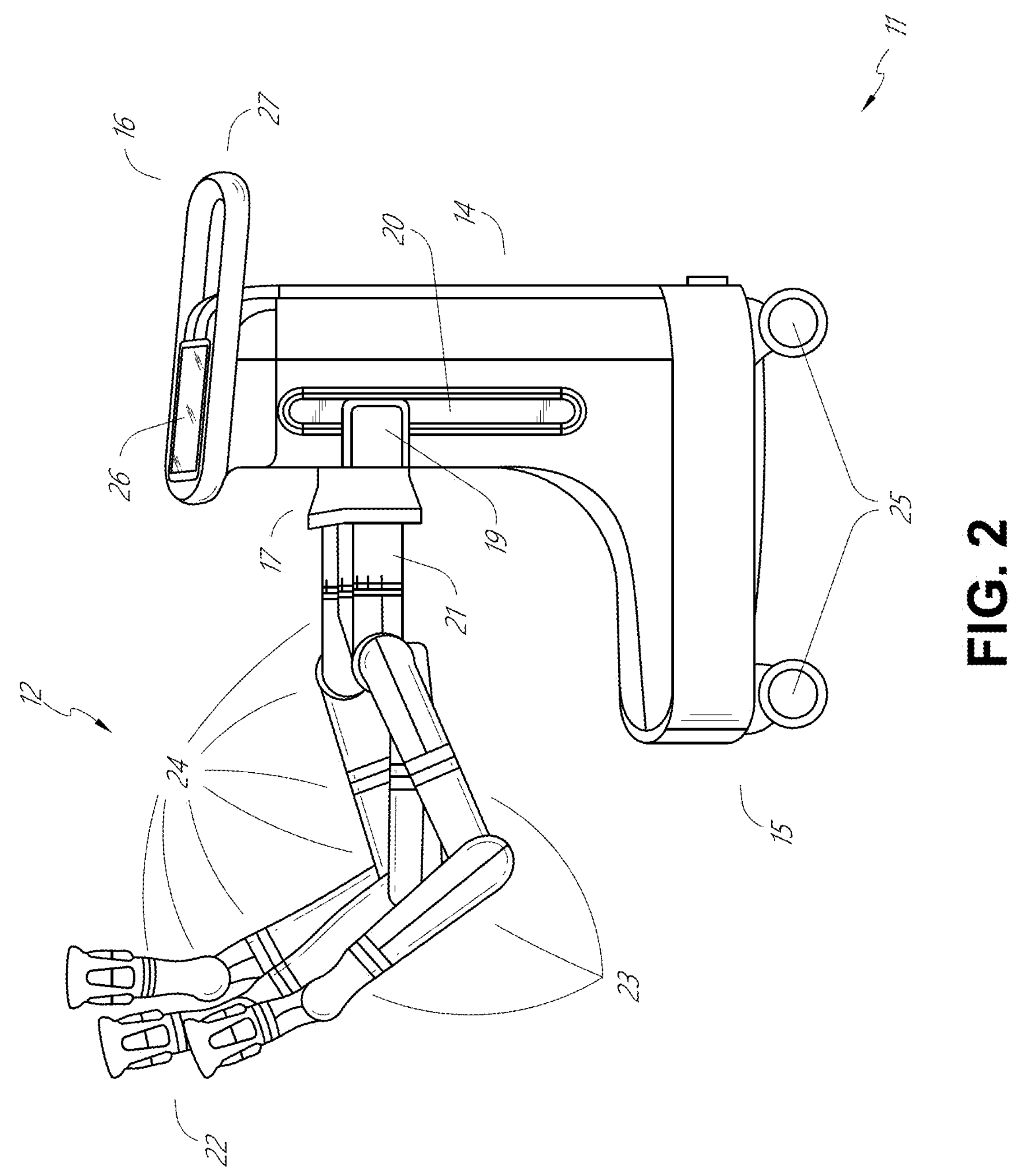
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
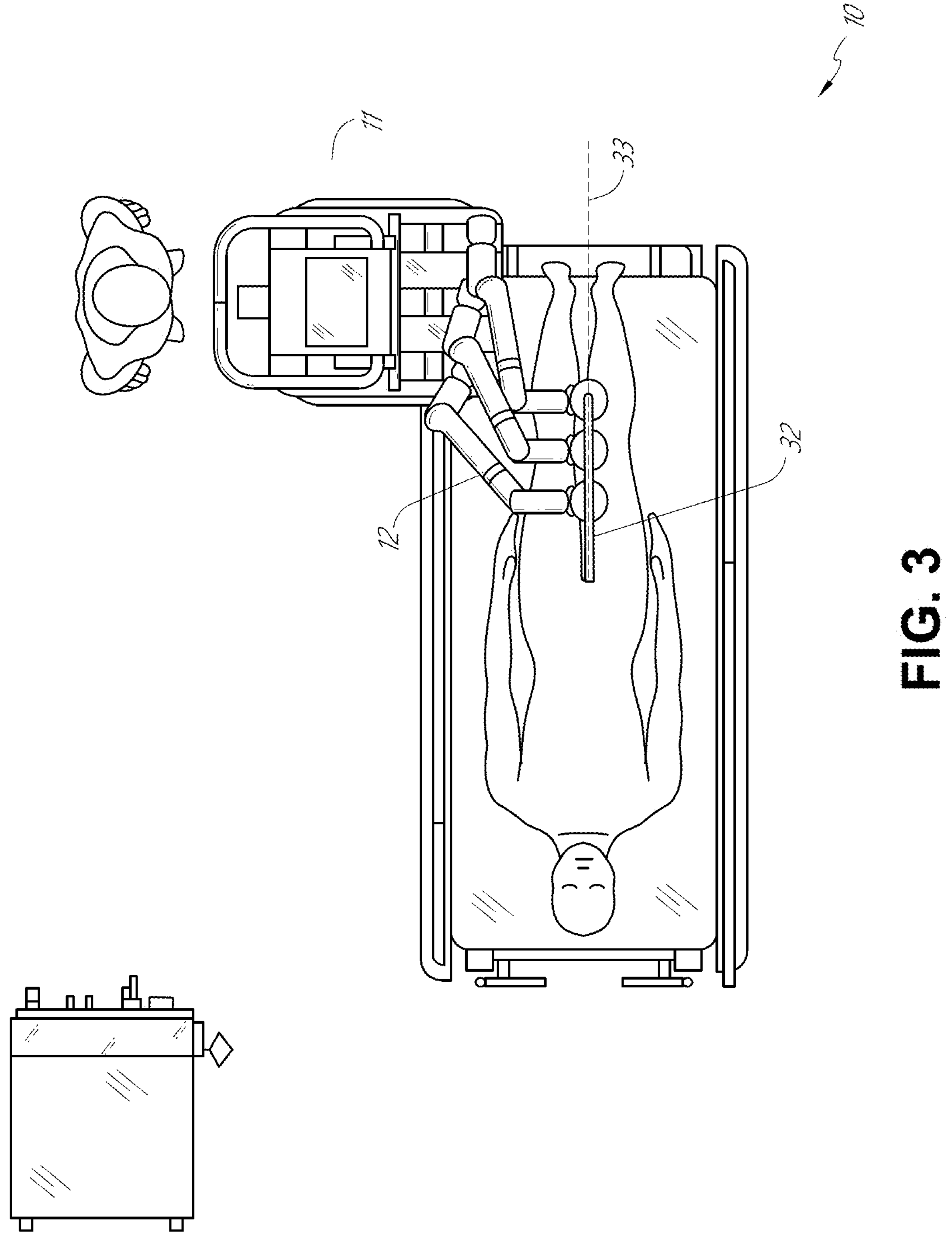
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
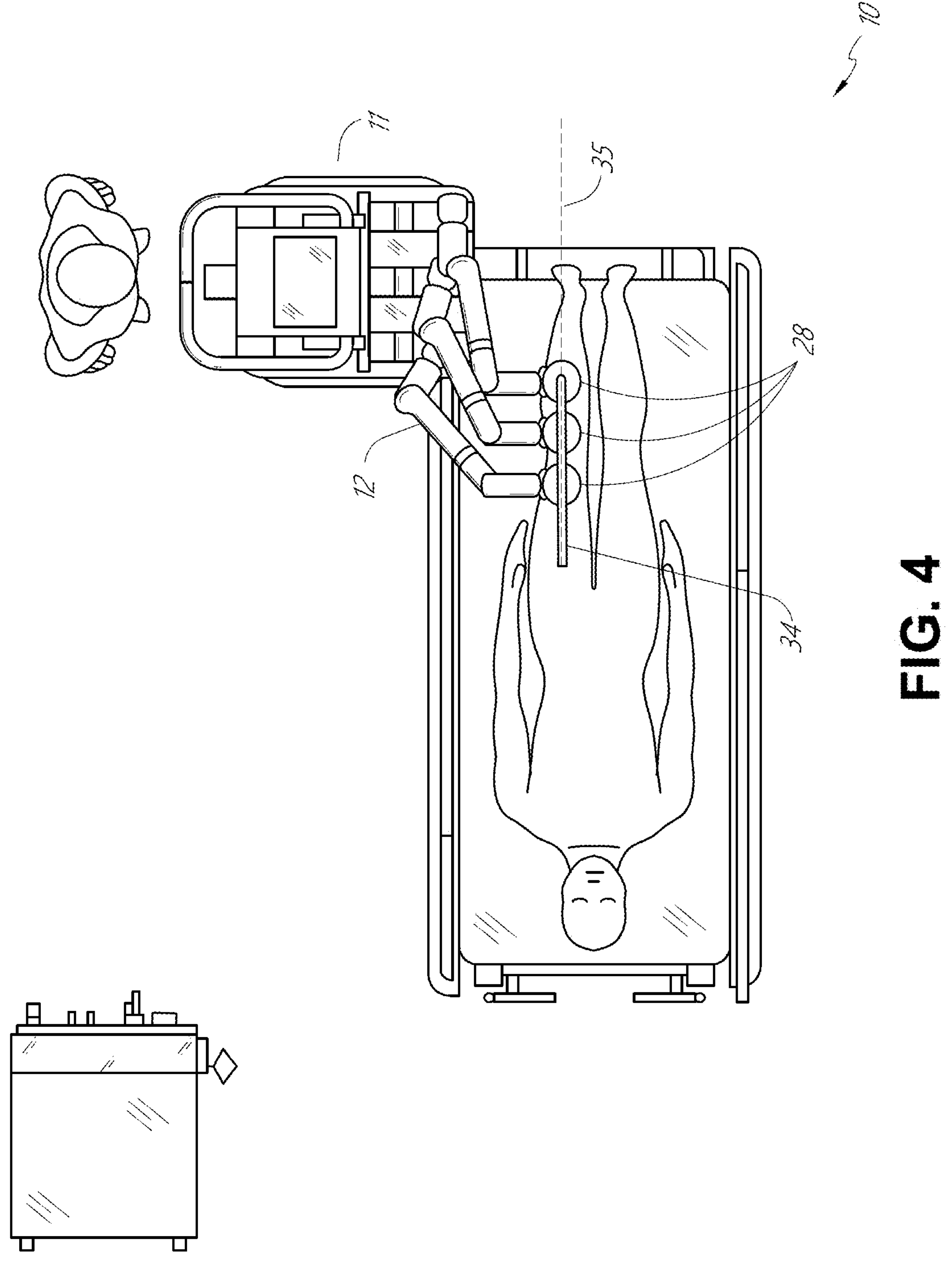
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
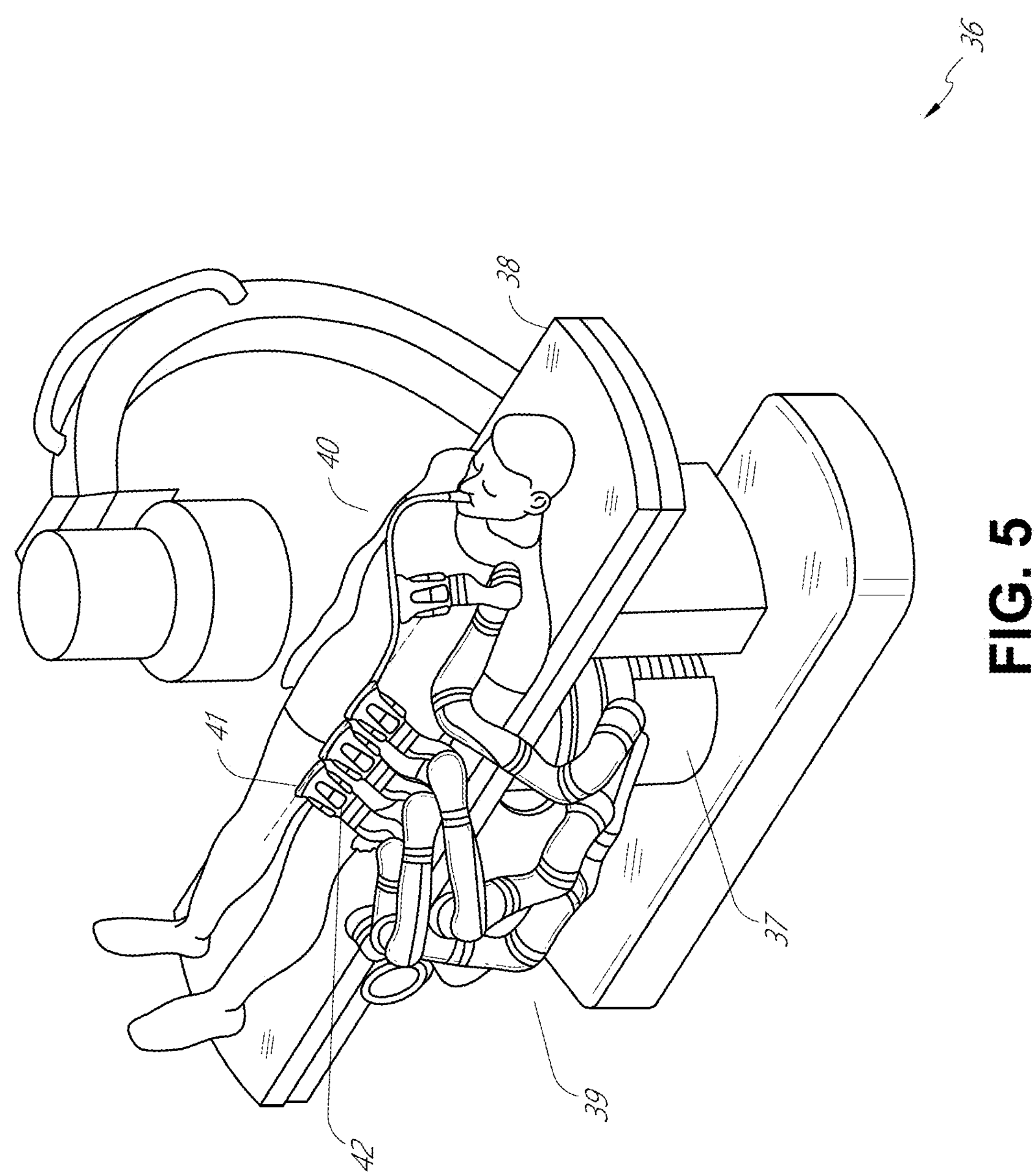
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
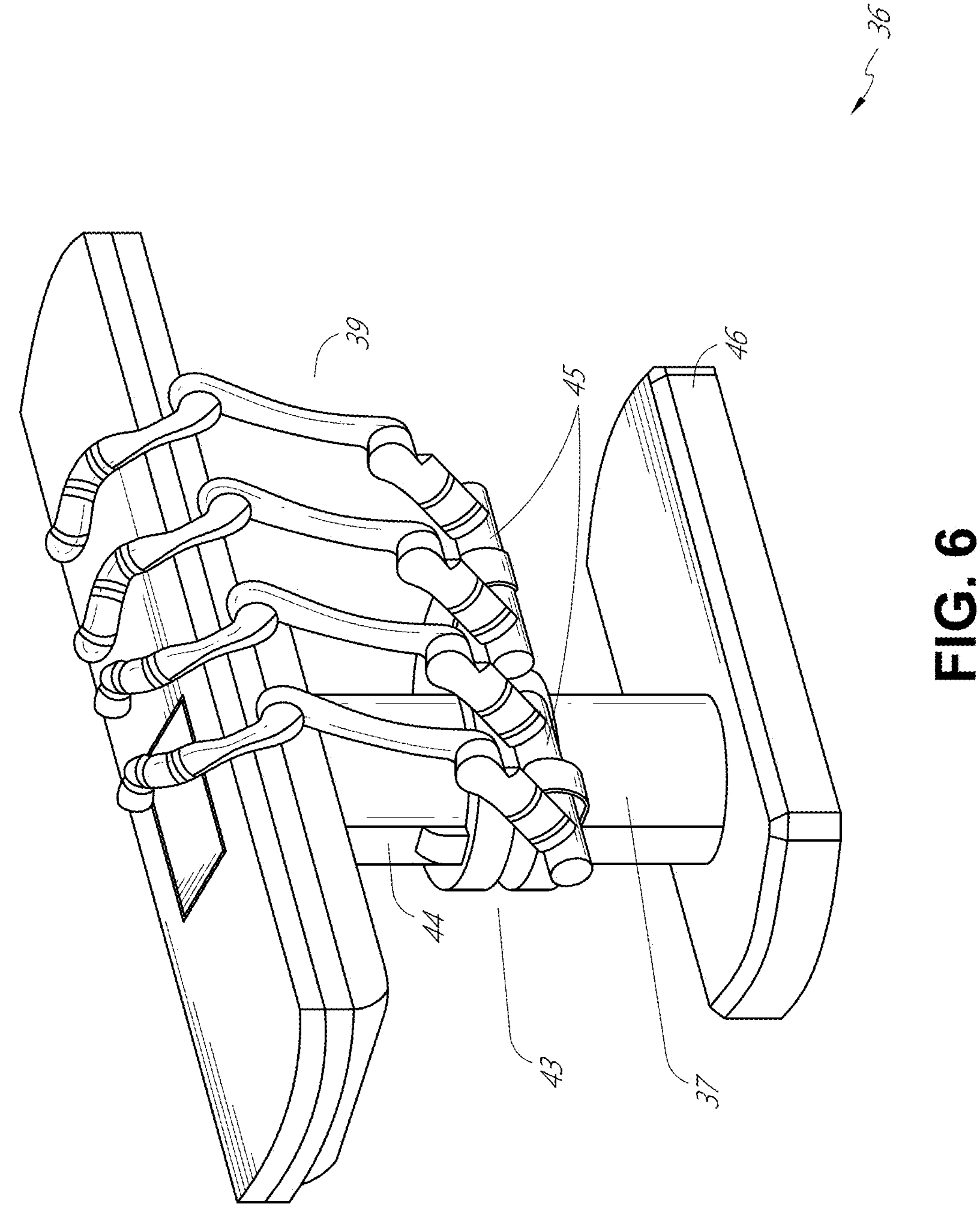
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
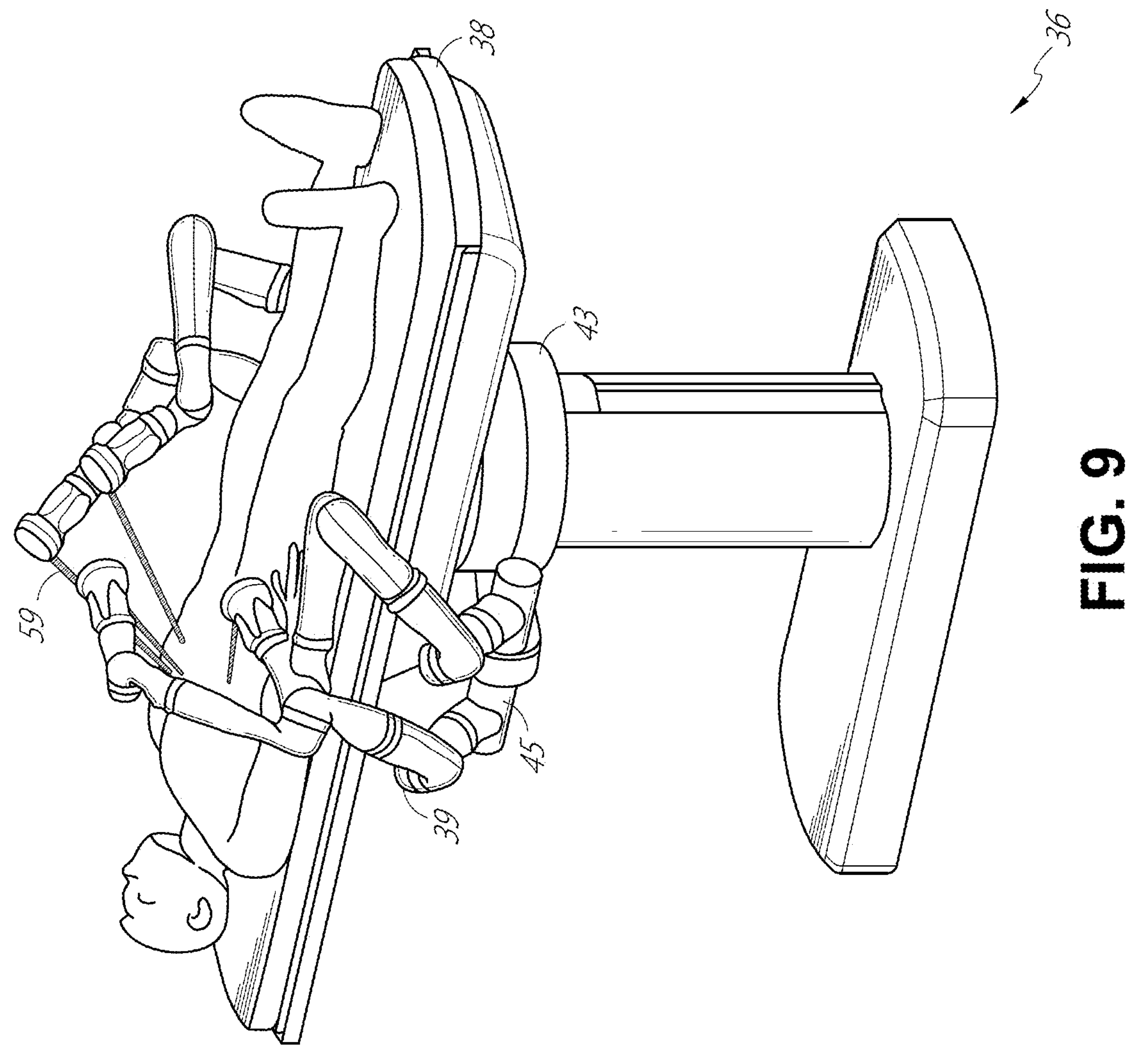
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
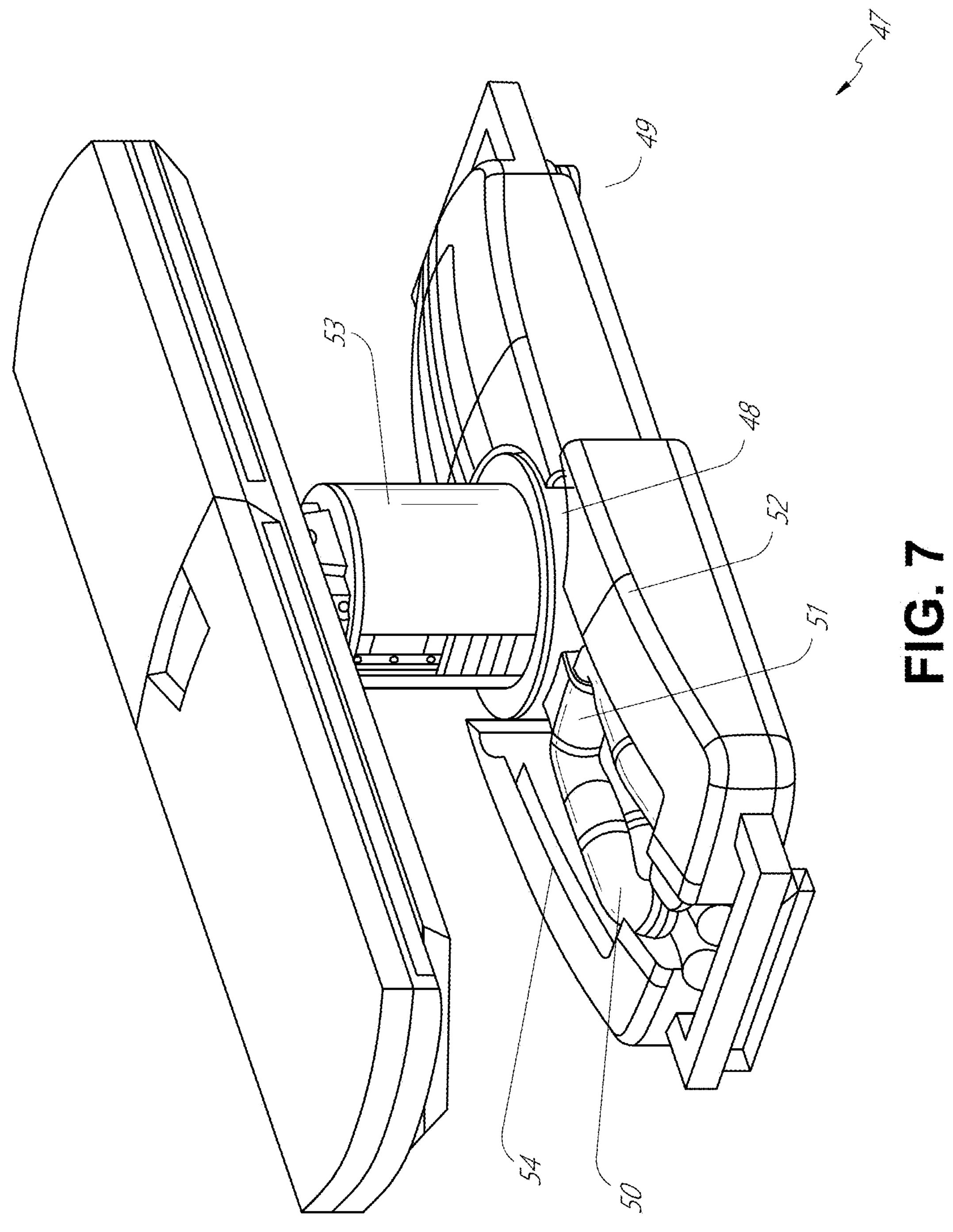
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
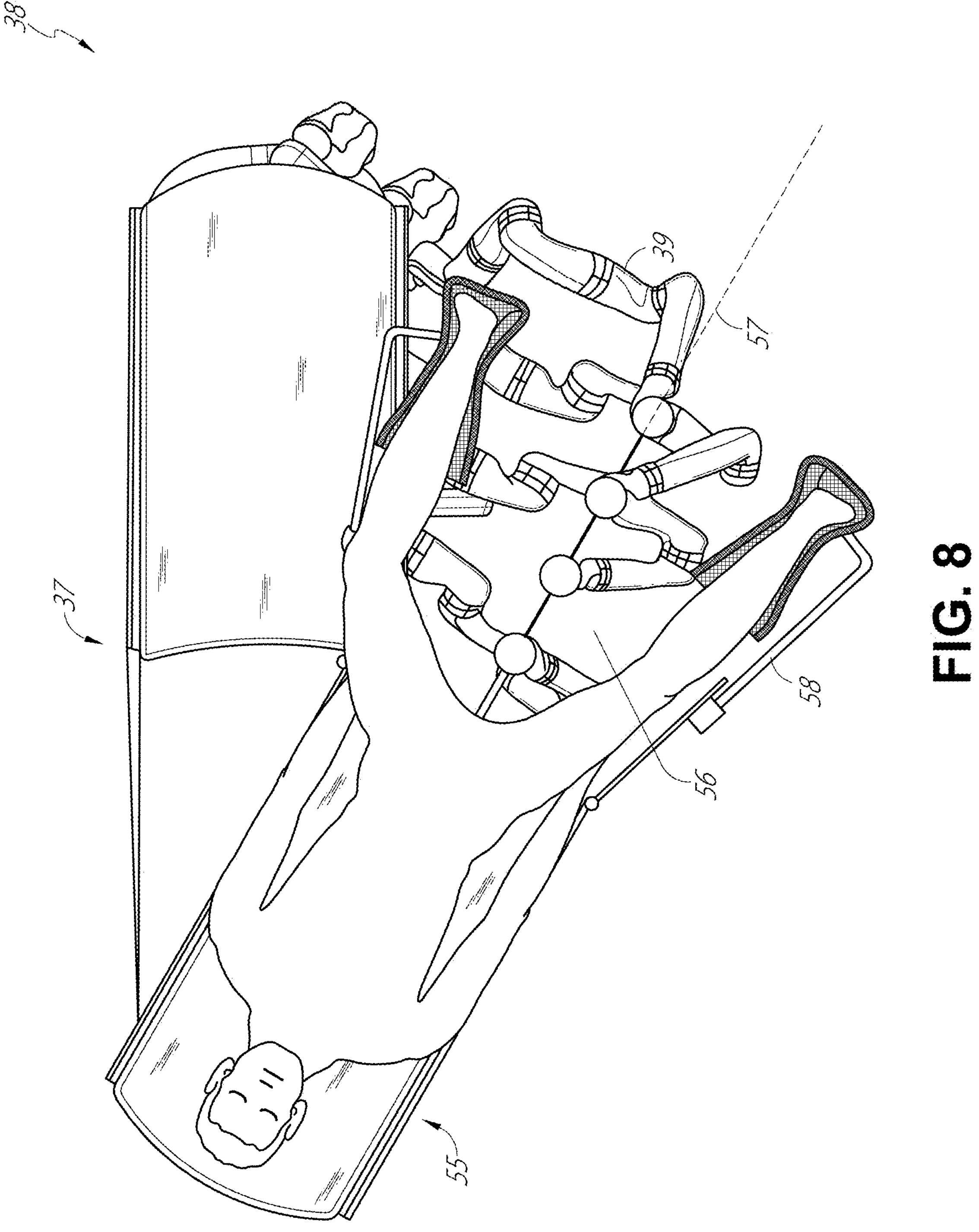
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
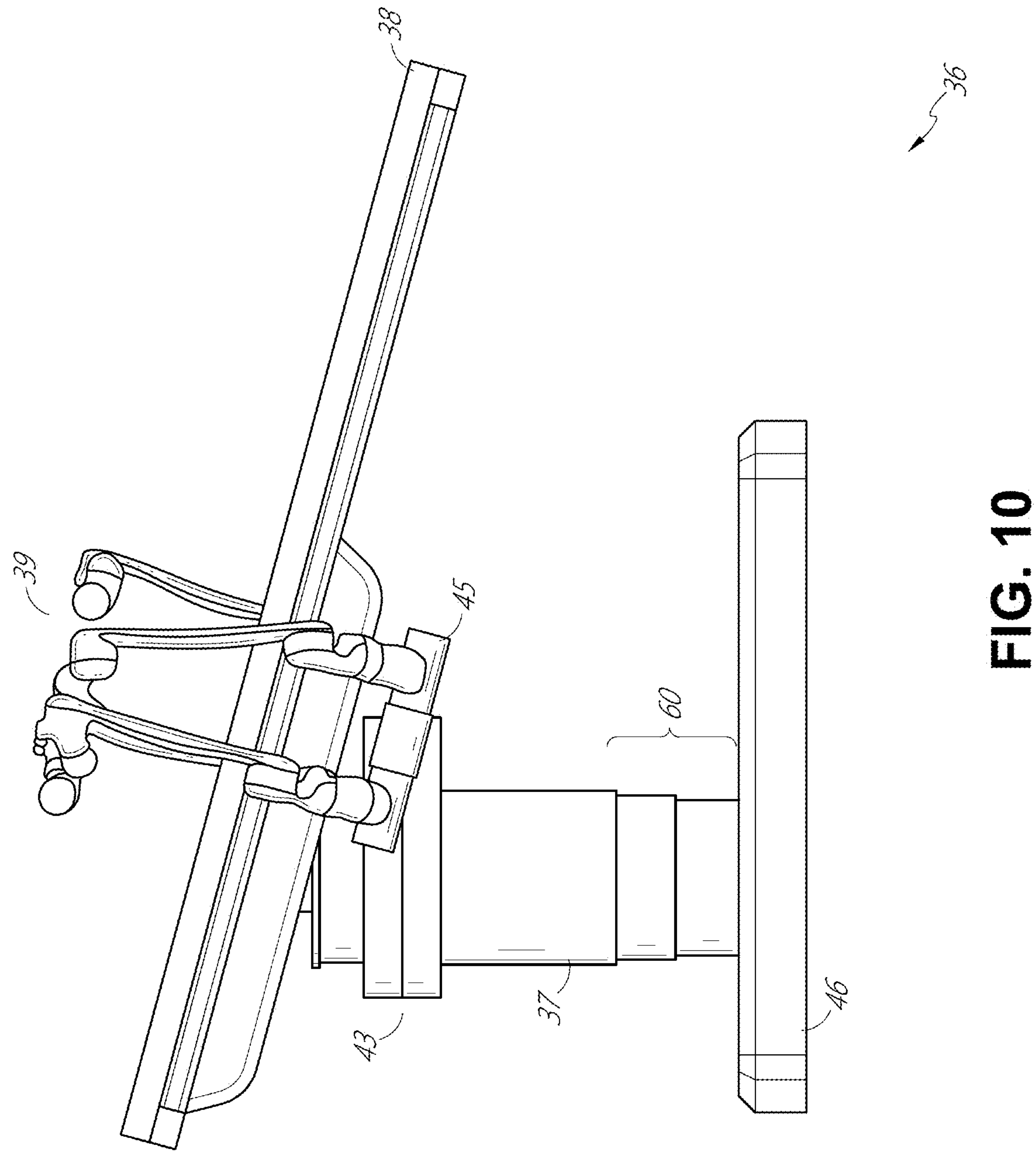
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
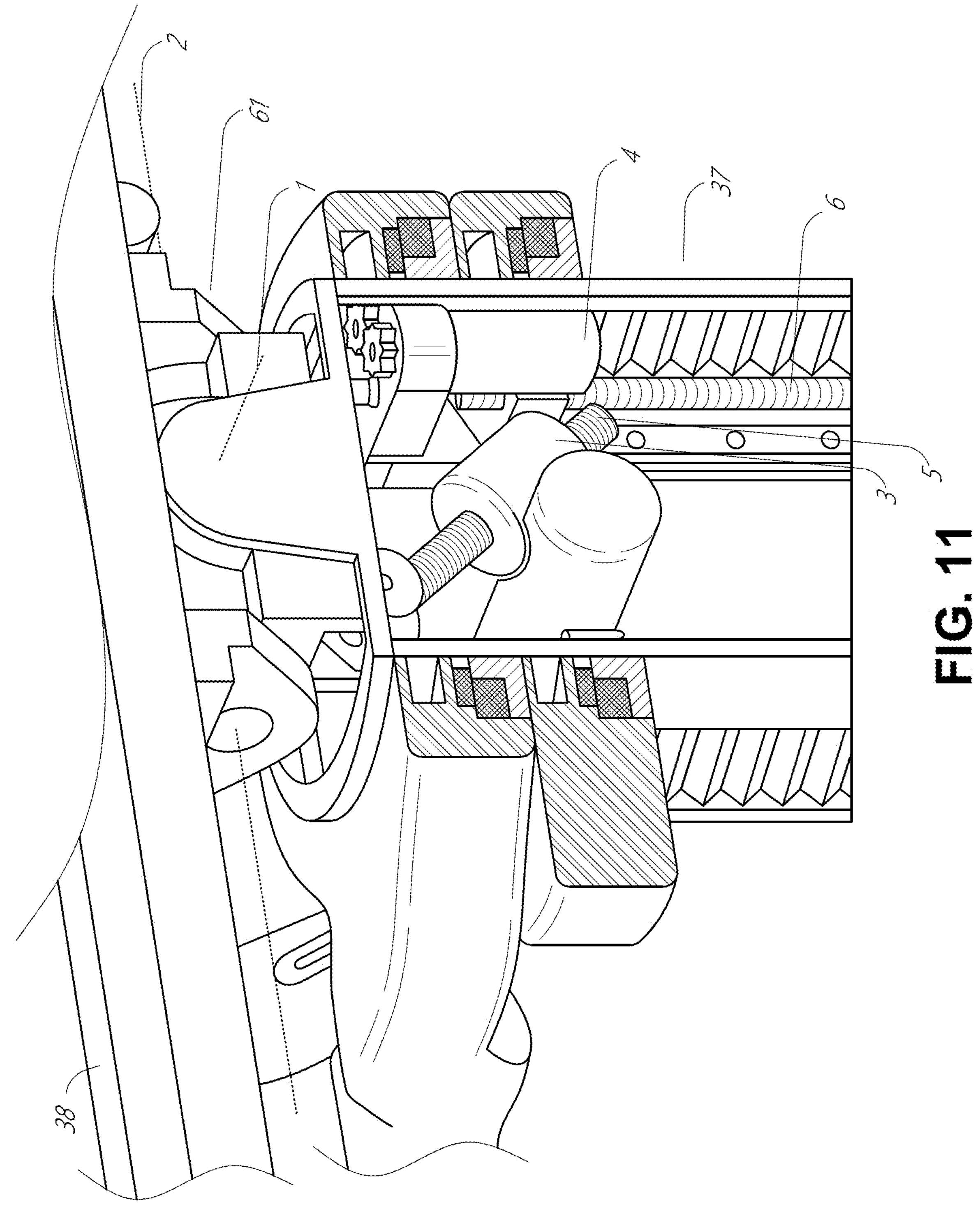
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
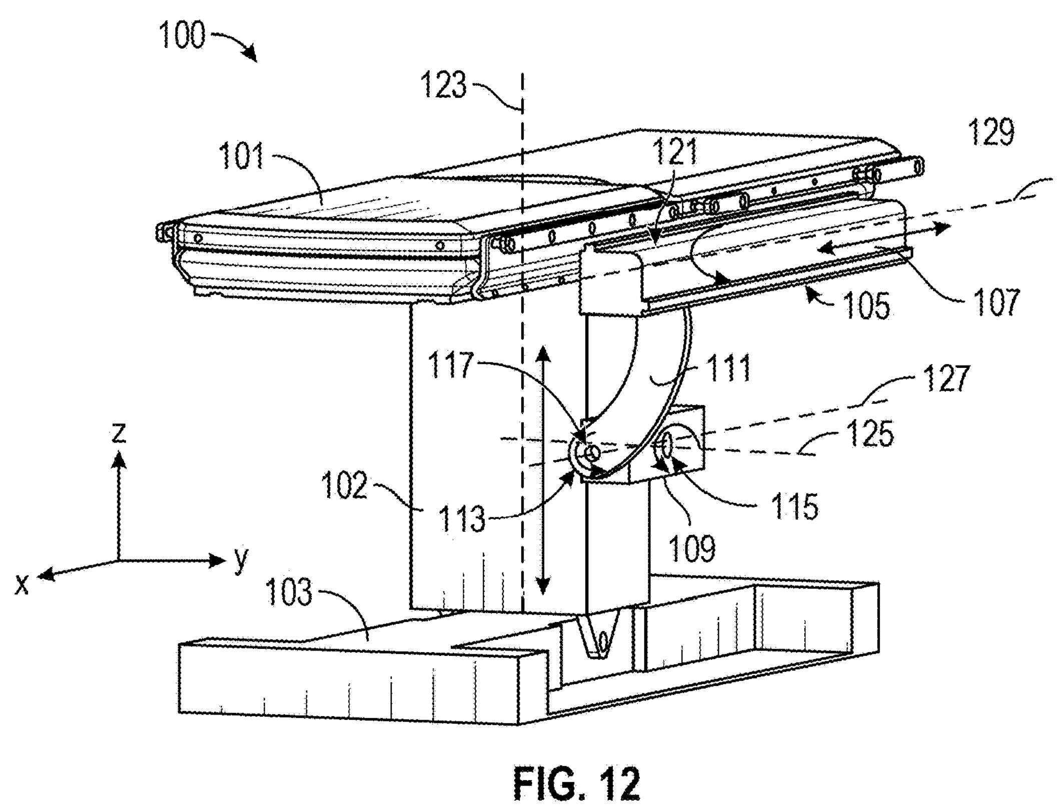
FIG. 12 illustrates an alternative embodiment of a table-based robotic system.
Figure 13:
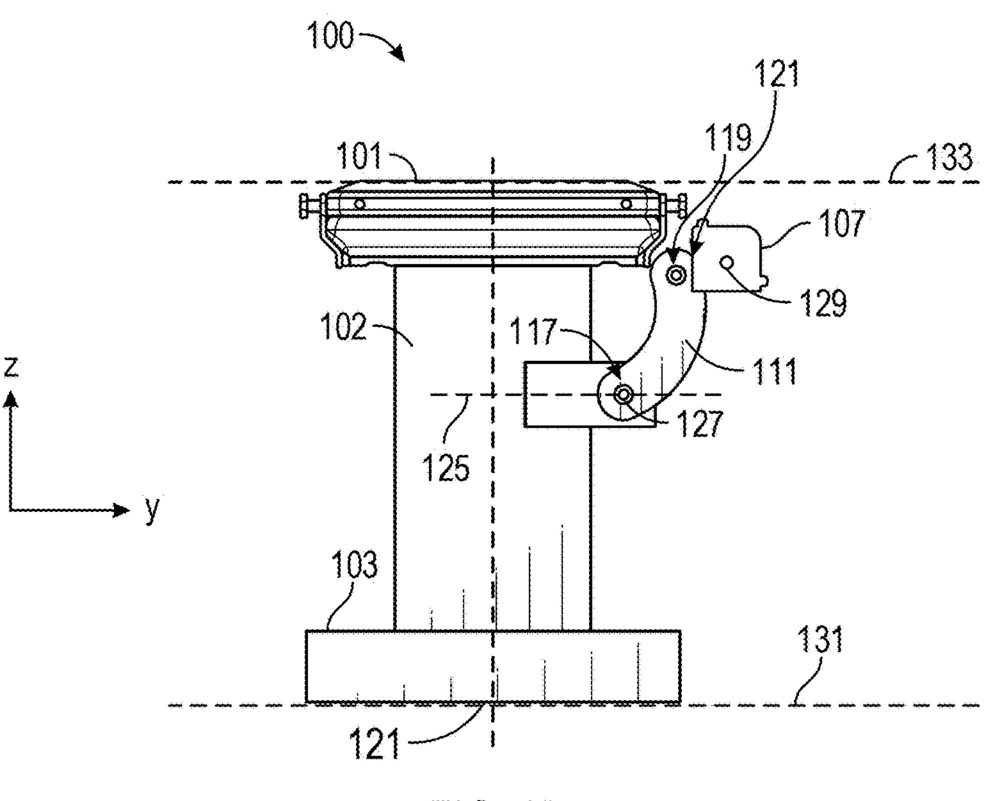
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
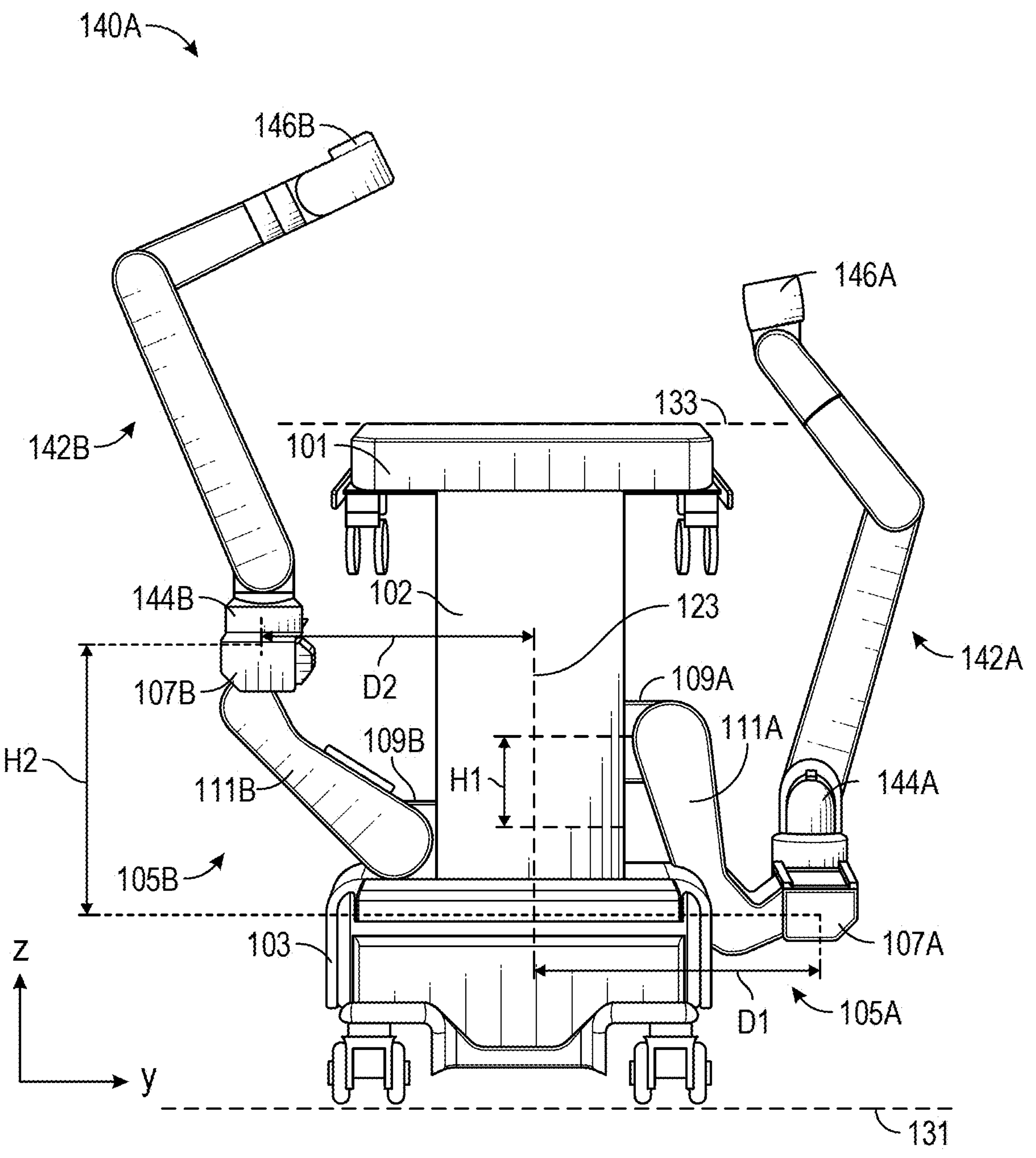
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
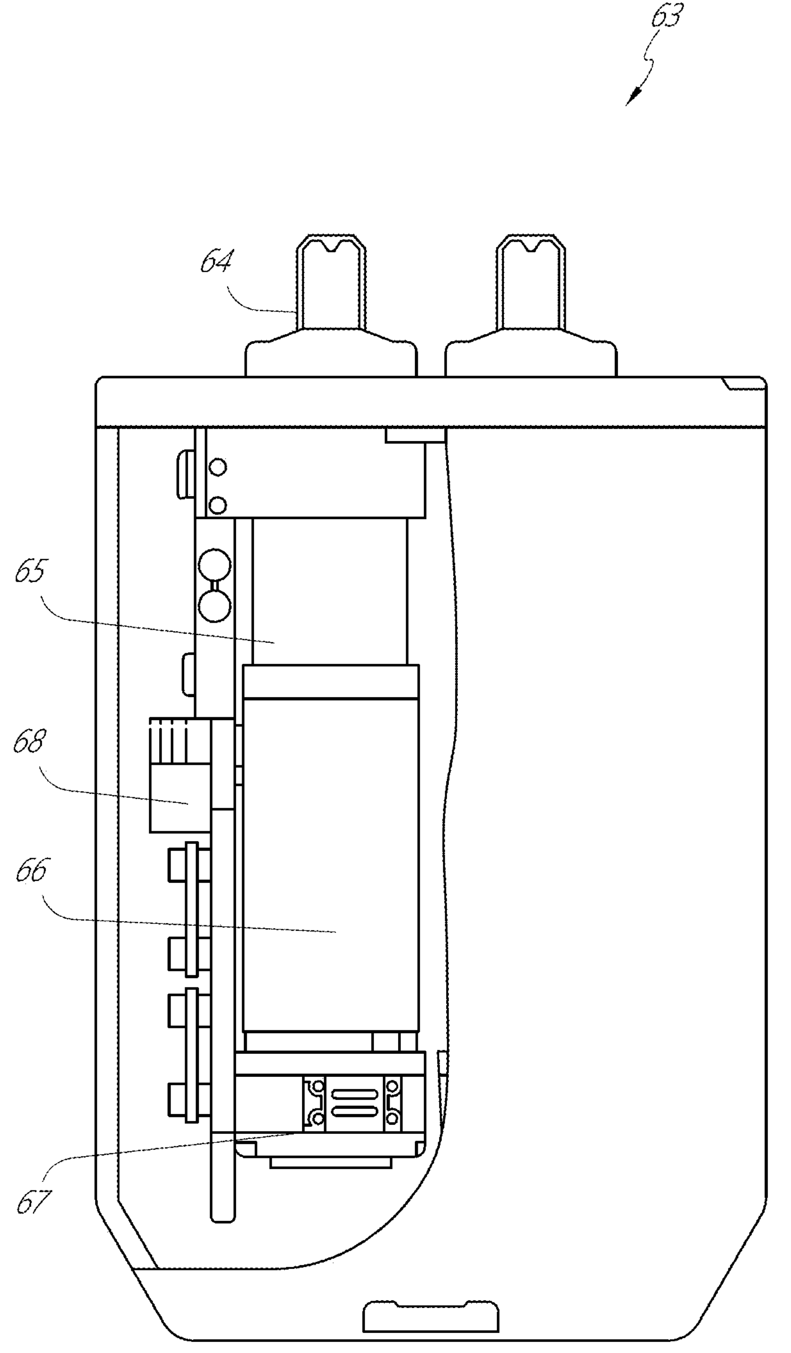
FIG. 15 illustrates an exemplary instrument driver.
Figure 15:

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
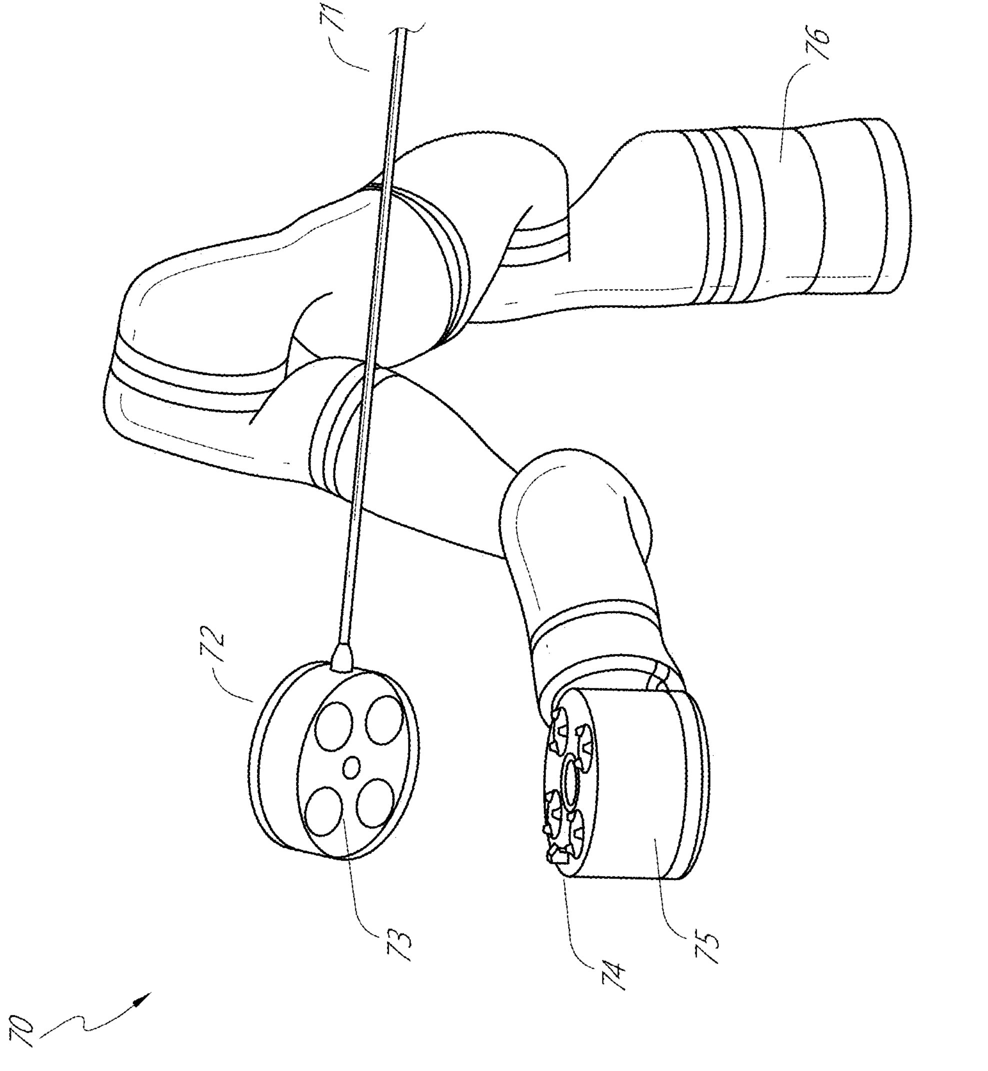
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
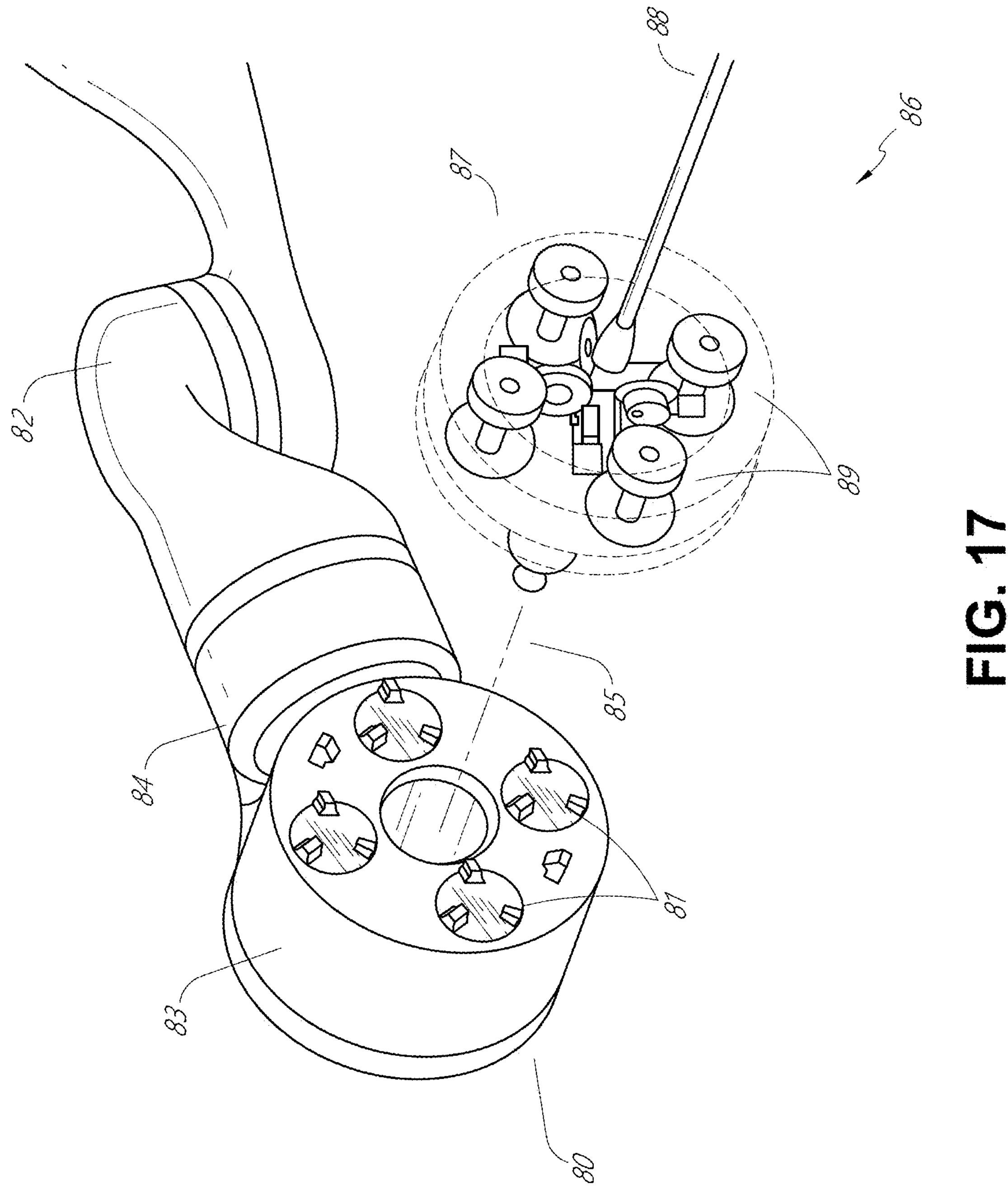
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
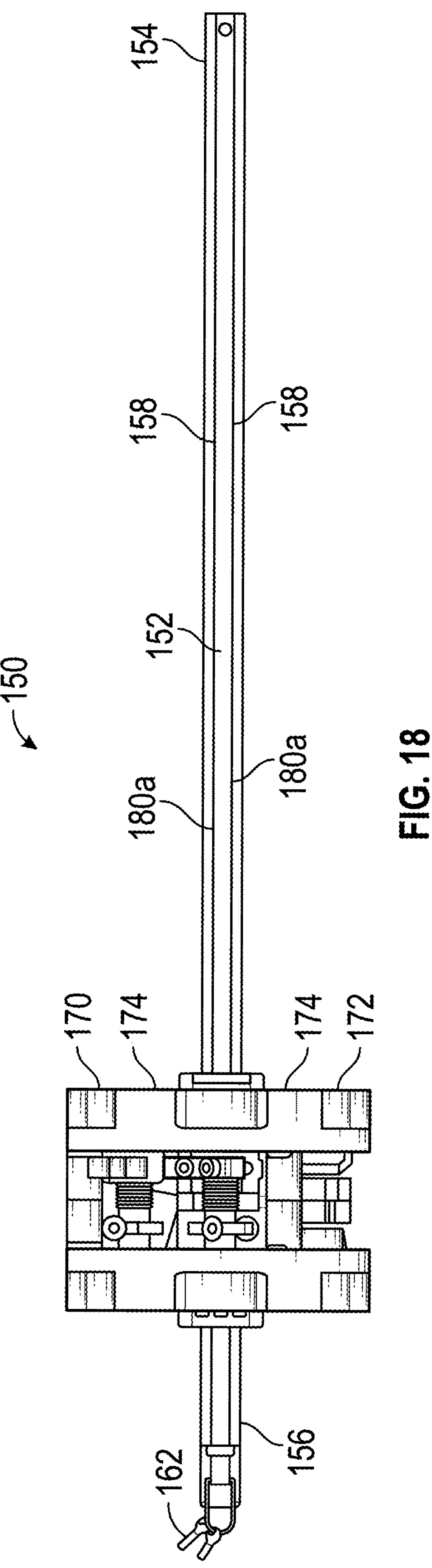
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
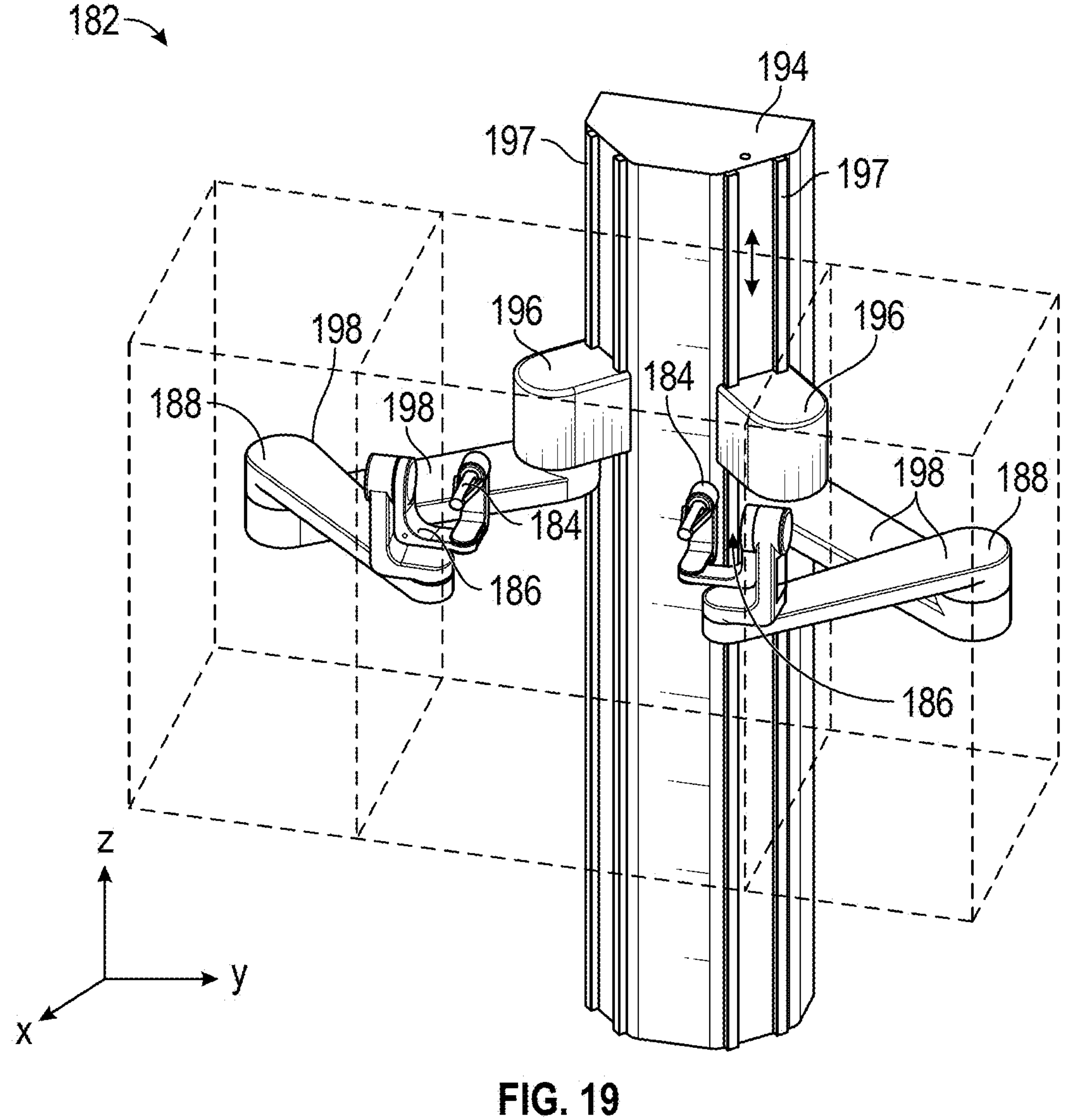
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
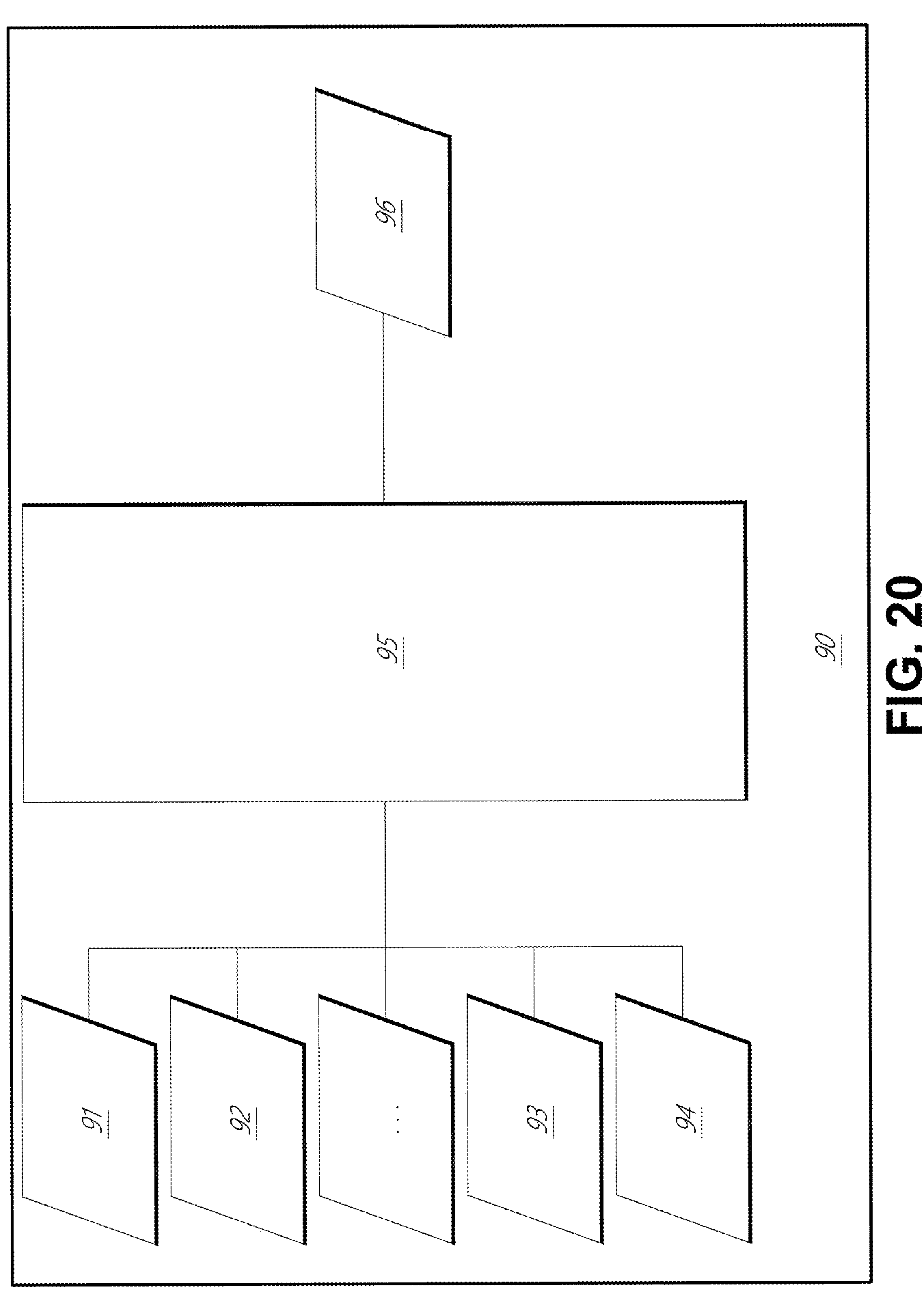
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as centerline geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Drape of Robotic System

Examples of the disclosure relate to systems and techniques for manual and/or robotically controllable medical instruments. The controllable medical instruments may be flexible or rigid, and can be used, in some aspects, with robotically-enabled medical systems, such as those described above with reference to FIGS. 1-20. In some aspects, the medical instruments can be configured for endoscopic procedures. For example, the medical instruments can be configured for uroscopy, ureteroscopy, gastroscopy, bronchoscopy, or other endoscopic procedures. In some examples, the medical instruments can be configured for laparoscopic procedures or other types of medical procedures (e.g., open procedures). The robotic arms (such as robotic arms 12 shown in FIGS. 1-4) may insert and steer the medical instruments into the patient robotically, manually, or a combination thereof. The system may include several robotic arms that may be used to control various medical instruments in coordination to execute various procedures.

Figure 21:
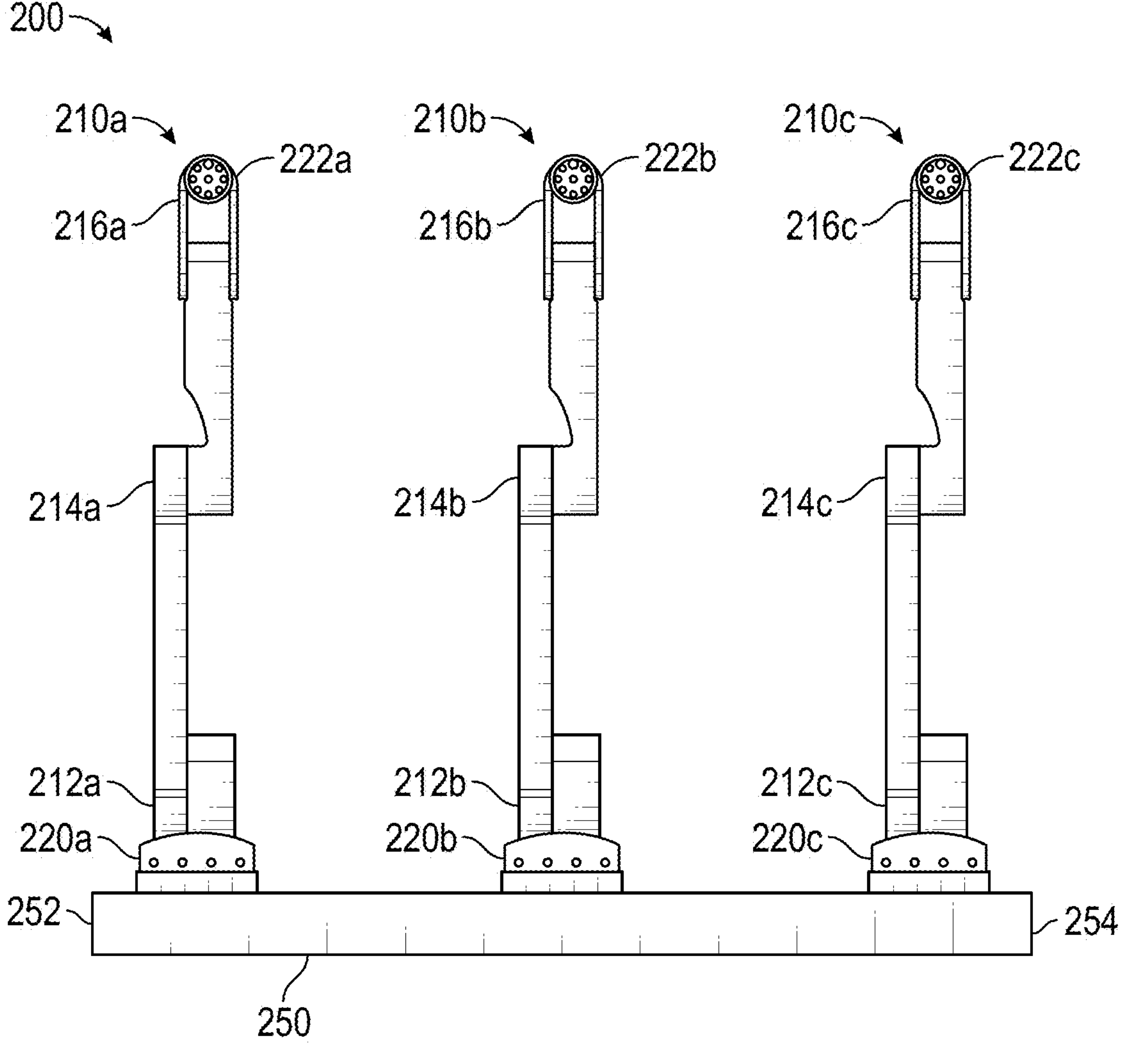
FIG. 21 illustrates a plurality of robotic arms and an adjustable arm support.

FIG. 21 illustrates a robotic system 200 comprising a one or more robotic arms 210 and an adjustable arm support 250. The one or more robotic arms 210 can include any number of robotic arms, such as one, two, three, four, five, or more arms. FIG. 21 illustrates three robotic arms 210*a*, 210*b*, 210*c*. Each robotic arm 210 can include a proximal end 212 and a distal end 216. Each robotic arm 210 can include a joint 214 to allow the proximal end 212 and distal end 216 of the robotic arm 210 to move and rotate relative to each other for increased range of motion. The distal end 216 can include an instrument drive mechanism 222, which can receive and actuate various medical instruments.

The present embodiment includes a plurality of robotic arms 210 that can be mounted on the adjustable arm support 250. The proximal end 212 of each robotic arm 210 can be received by a carriage 220. The carriage 220 may allow the robotic arms 210 to linearly translate along the length of the adjustable arm support 250, between the first end 252 of the adjustable arm support 250 and the second end 254 of the adjustable arm support 250. Each robotic arm can be moved independently of the other robotic arms. For example, the first robotic arm 210*a*, second robotic arm 210*b* and third robotic arm 210*c* may each be moved independently from each other. Any number of the robotic arms 210 can also be moved in coordination with each other. For example, all three robotic arms 210*a*, 210*b*, 210*c* can be moved simultaneously. In other examples, two robotic arms, such as the first and second robotic arms 210*a*, 210*b* can be moved simultaneously. Synchronized motion of the robotic arms 210 can include two or more robotic arms 210 moved in the same direction and/or by the same amount. In other examples, the robotic arms 210 can be moved simultaneously in different directions or by different amounts to achieve the desired positions of the robotic arms 210.

One or more adjustable arm supports 250 (each supporting one or more robotic arms 210) may be positioned near a patient platform or table (see, e.g., FIGS. 12-14). In some embodiments, two adjustable arm supports 250 can be attached to a column supporting the table, with an arm support 250 on each side of the table. Each arm support 250 can support one or more robotic arms 210. FIG. 21 illustrates the adjustable arm support 250 with three robotic arms 210*a*, 210*b*, 210*c*.

The adjustable arm support 250 can be adjustable to move relative to a table (not shown) to support and position the plurality of robotic arms 210. In some examples, the adjustable arm support 250 can move in at least one degree of freedom, such as vertically relative to the table. In addition to vertical movement, the adjustable arm support 250 can also be capable of additional degrees of freedom via tilt or horizontal translation. In some examples, the adjustable arm support 250 can move downward relative to the table to store the adjustable arm support 250 and the robotic arms 210 positioned thereon underneath the table when not in use. In some examples, during use, the adjustable arm support 250 can move upward relative to the table to allow the robotic arms 210 to position the robotic arms 210 to access to a patient positioned on the table. In some embodiments, the adjustable arm support 250 is capable of at least three or four degrees of freedom.

Figure 22A:
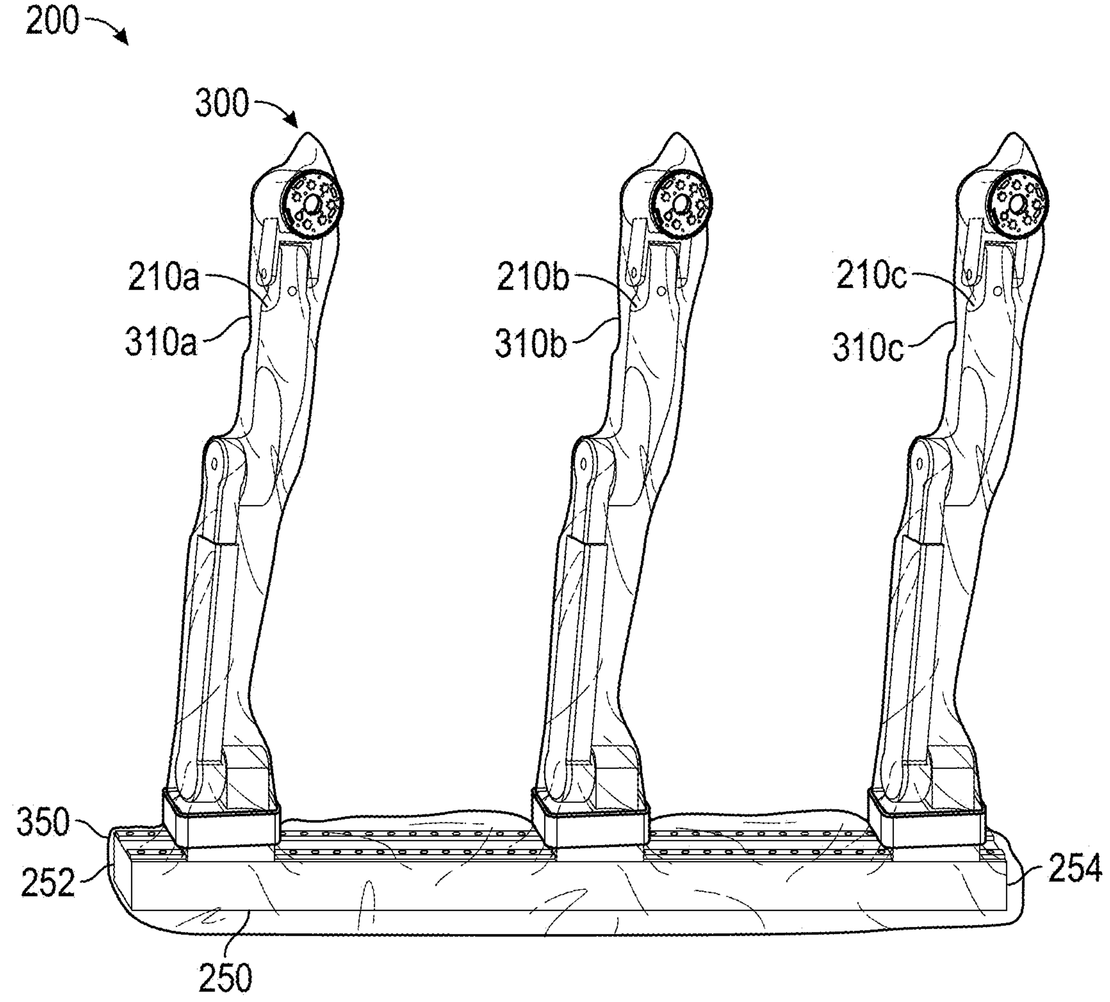
FIGS. 22A-B illustrate an example drape covering the plurality of robotic arms and the adjustable arm support.
Figure 22B:
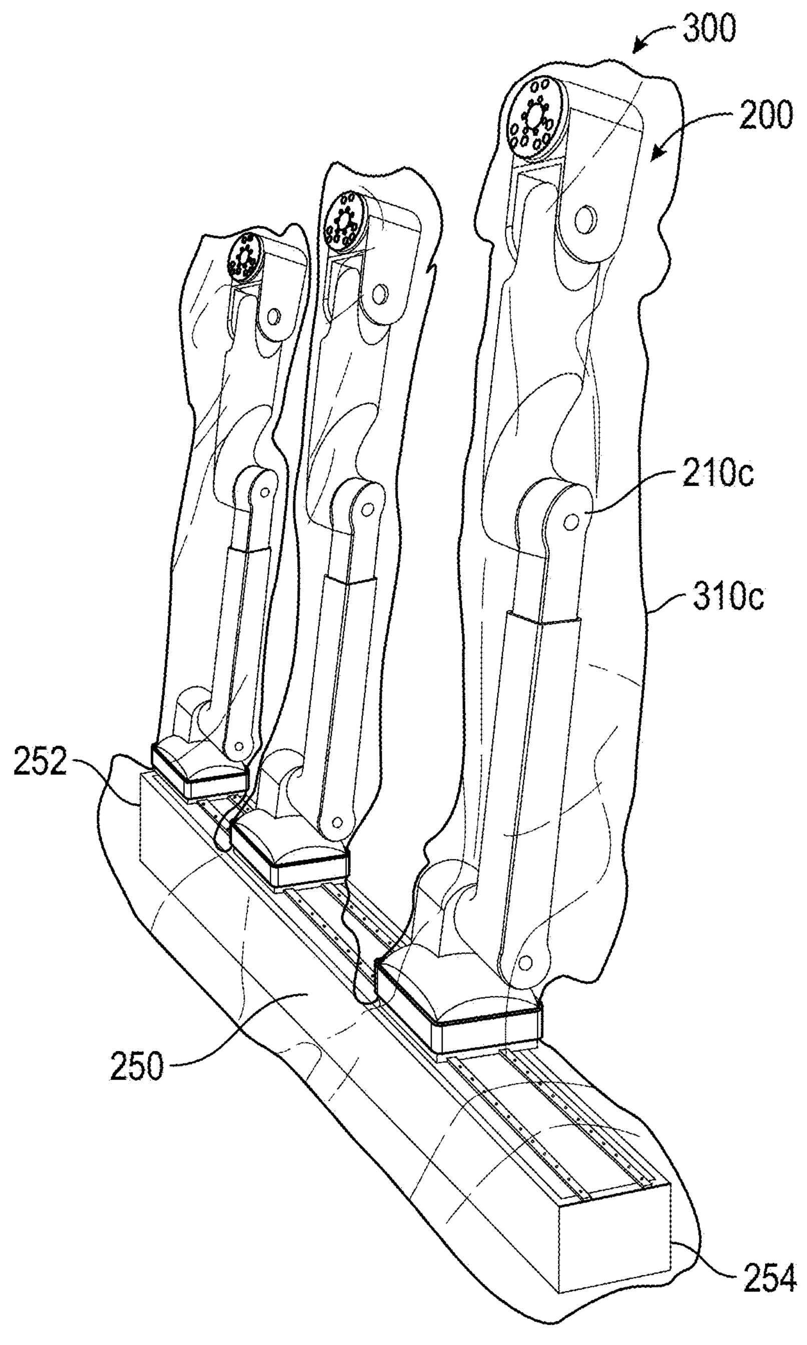

The robotic arms 210 and the adjustable arm support 250 can be positioned and used within a sterile field during medical procedures. Before, during, and after surgery, the robotic arms 210 and adjustable arm support 250 can be draped in a sterile fashion for use in medical procedures. FIGS. 22A-B illustrate a drape 300 covering the plurality of robotic arms 210 and the adjustable arm support 250.

With continued reference to FIGS. 22A-B, the drape 300 may be configured to cover a plurality robotic arms 210 as well as the adjustable arm support 250. The drape material can be comprised of a flexible and unstructured material that allows for flexibility and motion of the various parts of the robotic surgical system. There are a number of challenges when draping system components as part of a surgical procedure. For example, the flexible, unstructured material of the drape may be difficult to manage and control in a sterile fashion. Furthermore, as each robotic arm 210 can be long, the portion of the drape 300 covering each arm is expected to be just as long or longer. Due to this increased length, portions of the drape 300 can fold or flop in undesirable ways that can lead to undesired contamination. Additionally, the drape 300 can have several components attached (e.g. attachment components, sterile adapters, or other components). These additional components can add weight to portions of the drape 300, and can cause the portions of the drape to fall or unfold, thereby risking a contamination event, such as touching an unsterile, undraped portion of the robot.

To maintain sterility for the robotic system described herein, the drape 300 can be unfolded over the robotic arms 210 in a downward direction with the robotic arms 210 pointed upwards. The downward draping motion can advantageously allow for more control of the drape 300 during placement over the arms 210 (while using gravity to its advantage) and can also allow the drape 300 to remain within the sterile field during the draping process. One challenge with the downward draping motion is that the drape 300 can sometimes close or twist on itself, which can make it difficult to for the user to drape the arms 210. To make it easier to drape the arms, the drape 300 can be packaged and folded to easily position the drape 300 and to unfold the drape 300 in a controlled manner. As will be described more below, the drape 300 can also be designed to include a cuff of stiffer material, which the drape 300 can be folded over in a telescoping fashion to provide tension and hold an opening of the drape 300 for the draping process.

Additionally, the adjustable arm support 250 may also be draped. The adjustable arm support 250 can be particularly challenging as the adjustable arm support 250 can support a plurality of robotic arms 210 which can linearly translate relative to the length of the adjustable arm support 250. To maintain sterility, the robotic arms 210 and the adjustable arm support 250 can be draped simultaneously and with a single drape 300. However, draping both the plurality of robotic arms and the adjustable arm support adds complexity to the shape and design of the drape configuration, in particular in designing the drape to maintain sterility during the draping process. The drape 300 should be able to accommodate the motion of the plurality of robotic arms 210 linearly relative to the length of the adjustable arm support 250, as well motion of each robotic arm 210 in several degrees of motion. As will be described more below, the drape 300 can be multiple times longer (e.g., at least two, three, or four times longer) than the adjustable arm support 250 to accommodate the motion of the plurality of robotic arms 210 relative to the surface of the adjustable arm support 250.

Figure 23A:
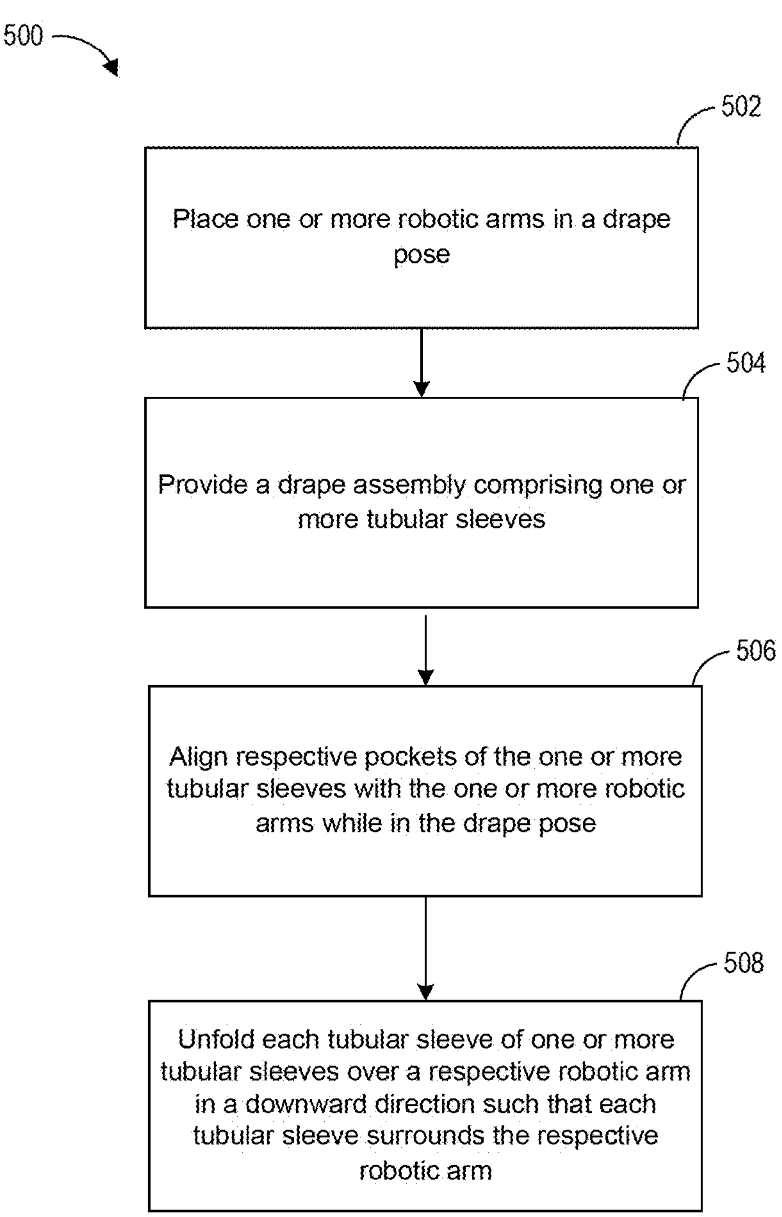
FIG. 23A-B is a flowchart that illustrates an example process for draping a robotic surgical system.
Figure 23B:
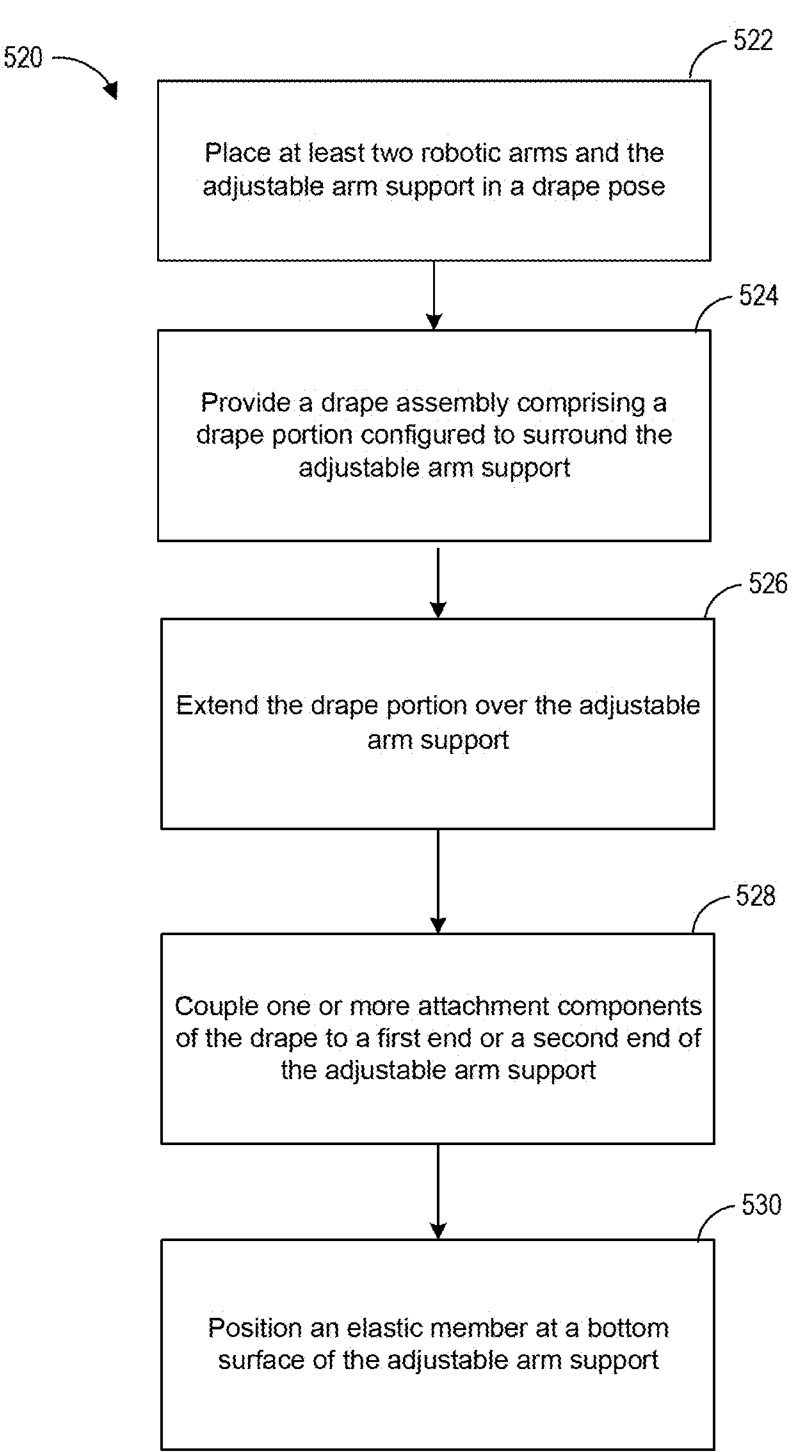

FIG. 23A-B is a flowchart that illustrates a process for draping a robotic surgical system. FIG. 23A is a flowchart that illustrates a process for draping one or more robotic arms, while FIG. 23B is a flowchart that illustrates a process for draping one or more adjustable arm, supports.

FIG. 23A is a flowchart that illustrates a process 500 of draping one or more robotic arms. As described above, the one or more robotic arms can include at least two robotic arms. The method 500 begins at block 502, at which one or more robotic arms are positioned or placed in a drape pose. In the drape pose, the one or more robotic arms may be directed generally upwards, though one skilled in the art will appreciate that the robotic arms may also be directed generally downwards in some embodiments.

Next, the method moves to block 504, to provide a drape assembly or drape including one or more tubular sleeves. In some examples, the drape assembly or drape can include a number of tubular sleeves that corresponds to the number of robotic arms. Each tubular sleeve can include one or more folds that forms a pocket to receive a respective robotic arm. The one or more tubular sleeves can be configured to surround the one or more robotic arms when unfolded.

The method 500 then moves to block 506, at which the respective pockets of the one or more tubular sleeves are aligned with the one or more robotic arms while in the drape pose.

Finally, the method moves to block 508, at which each tubular sleeve is unfolded over a respective robotic arm in a downward direction such that each tubular sleeve surrounds the respective robotic arm. The one or more tubular sleeves may be unfolded simultaneously or consecutively over the respective robotic arms.

FIG. 23B is a flowchart that illustrates a process 520 of draping the adjustable arm support. In some examples, the process 520 of draping the adjustable arm support can be performed after the process 500 of draping one or more robotic arms. In some examples, the process 520 of draping the adjustable arm support can be performed before or simultaneously with the process 500 of draping the robotic arms.

The method 520 begins at block 522, at which one or more robotic arms and the adjustable arm support in a drape pose. As described above, in the drape pose, the one or more robotic arms are generally upwards. In the drape pose, the adjustable arm support may be positioned within the sterile environment, which may include raising the height of the adjustable arm support.

Next, the method 520 moves to block 524, to provide a drape assembly or drape with a drape portion configured to surround the adjustable arm support. In some examples, the drape portion configured to surround the adjustable arm support is connected to the drape portion configured to surround the one or more robotic arms (e.g. the tubular sleeves as described in process 500). In some examples, the drape portion configured to surround the adjustable arm support is separate from the drape portion configured to surround the one or more robotic arms.

The method 520 then moves to block 526 to extend the drape portion over the adjustable arm support to cover the adjustable arm support.

Optionally, the method 520 can move to block 528, where one or more attachment components of the drape is coupled to the adjustable arm support, such as a first end and/or a second end of the adjustable arm support. The coupling of the attachment component of the drape to the adjustable arm support can include inserting a portion of a latch on the adjustable arm support into a slot of a card attached on the drape and rotating the card to position the card against the end of the adjustable arm support.

The method 520 then moves to block 530, where an elastic member is positioned at a bottom surface of the adjustable arm support. The drape portion configured to cover the adjustable arm support can include an elastic member. The elastic member can be inserted into a hem of the drape portion configured to cover the adjustable arm support. The elastic member can gather the drape portion and keep the drape portion in position covering the adjustable arm support.

A. Draping Robotic Arms

Figure 25:
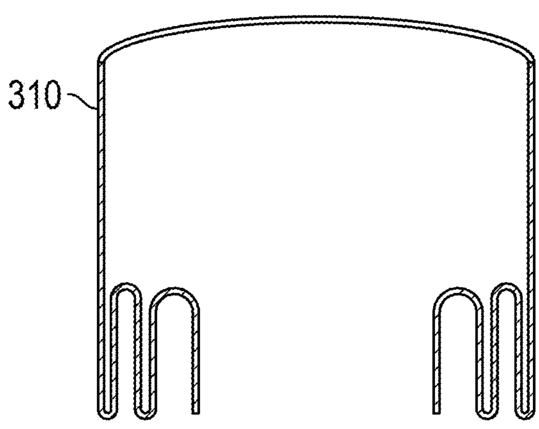
FIG. 25 illustrates an example tubular sleeve without a cuff.
Figure 26C:
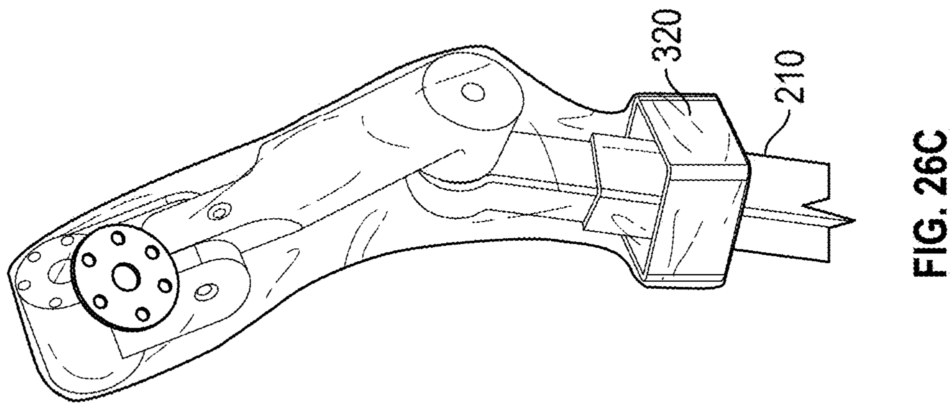
FIGS. 26A-26C illustrate draping a tubular sleeve over a robotic arm.
Figure 26B:
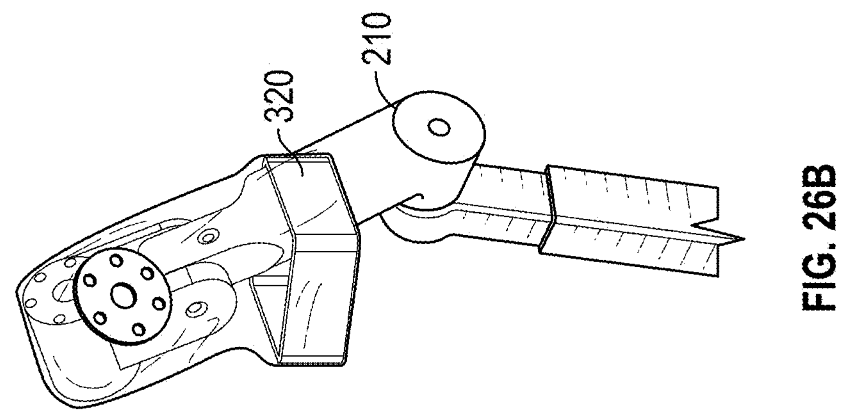
Figure 26A:
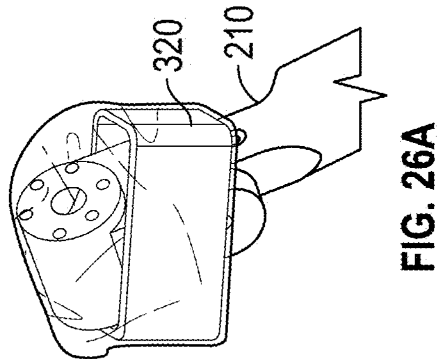

As described herein, the drape or drape assembly 300 can include one or more tubular sleeves 310 configured to surround and cover one or more robotic arms 210. Each tube-shaped drape or tubular sleeve 310 is designed to cover at least one robotic arm 210. FIGS. 26A-26C show the application of a drape of a robotic arm, while FIGS. 24A-25 illustrate the specific novel features of such a drape.

Figure 24A:
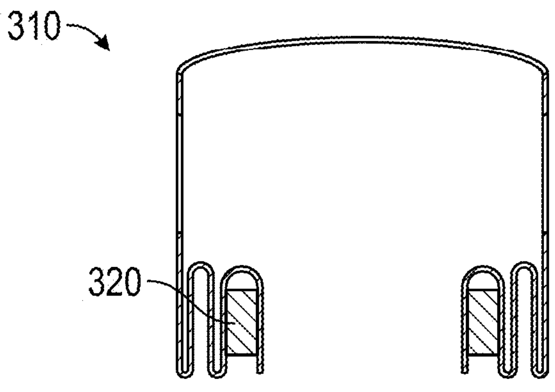
FIG. 24A illustrates a tubular sleeve in a folded configuration.

FIG. 24A illustrates a tubular sleeve 310 in a folded configuration. This folded configuration allows the tubular sleeve 310 to remain sterile, for ease of transport, and for ease of alignment with the robotic arm. In some examples, the tubular sleeve 310 (which may also be called a tube-shaped drape or tube) is coupled to a frame or cuff 320 that is positioned at a base or proximal end of each tubular sleeve 310. In some examples, the cuff 320 is formed of a material that is stiffer than the drape material of the tubular sleeve 310. In some examples, the cuff 320 can be formed of polyethylene or polystyrene, and additionally can have any number of shapes or change shape as force is applied to it. In some examples, the drape material can be formed of an elastomeric material. In some examples, the cuff 320 can be the same, substantially the same, or a similar diameter to the tubular sleeve 310. In some examples, the cuff 320 may have a slightly larger diameter than the diameter of the tubular sleeve 310. The tubular sleeve 310 is folded in a telescoping or accordion fashion about the outside of or over the cuff 320. The tubular sleeve 310 can be folded about an outside surface of a cuff 320 as pleated folds. The tubular sleeve 310 can be folded over the cuff 320 repeatedly in a telescoping or pleated manner, as shown in FIG. 24A.

During use, the tubular sleeve 310 can be configured to be stretched over its respective cuff 320 and have a tension against its respective cuff 320. The tension of the folded tubular sleeve 310 against its respective cuff 320 advantageously facilitates holding the respective tubular sleeve 310 open. The tension of the elastomeric material of the drape material stretching over the cuff 320 holds the folds of the tubular sleeve 310 in place and resists unfolding or unraveling forces. As the cuff 320 is substantially the same diameter as the tubular sleeve 310, this helps to keep the folded tubular sleeve 310 in tension and therefore open. In other words, the packaging or folding of the tubular sleeve 310 about the outside of the cuff 320 helps to keep the tubular sleeve 310 from unraveling and therefore prevents contamination.

Figure 24B:
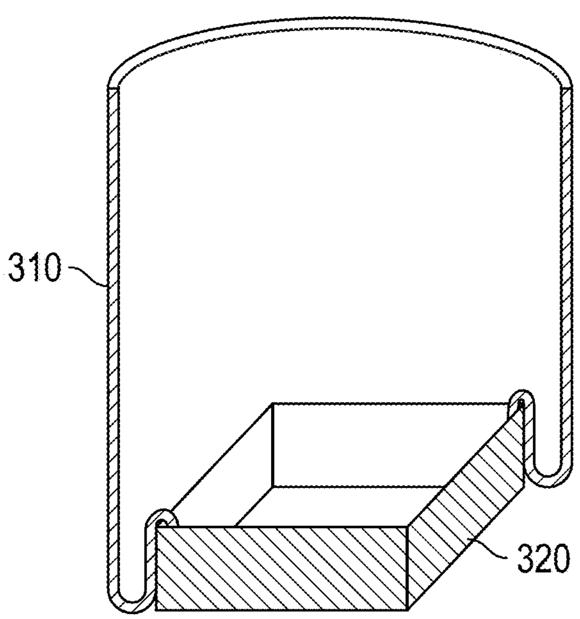
FIG. 24B illustrates a tubular sleeve in a partially folded configuration.
Figure 24C:
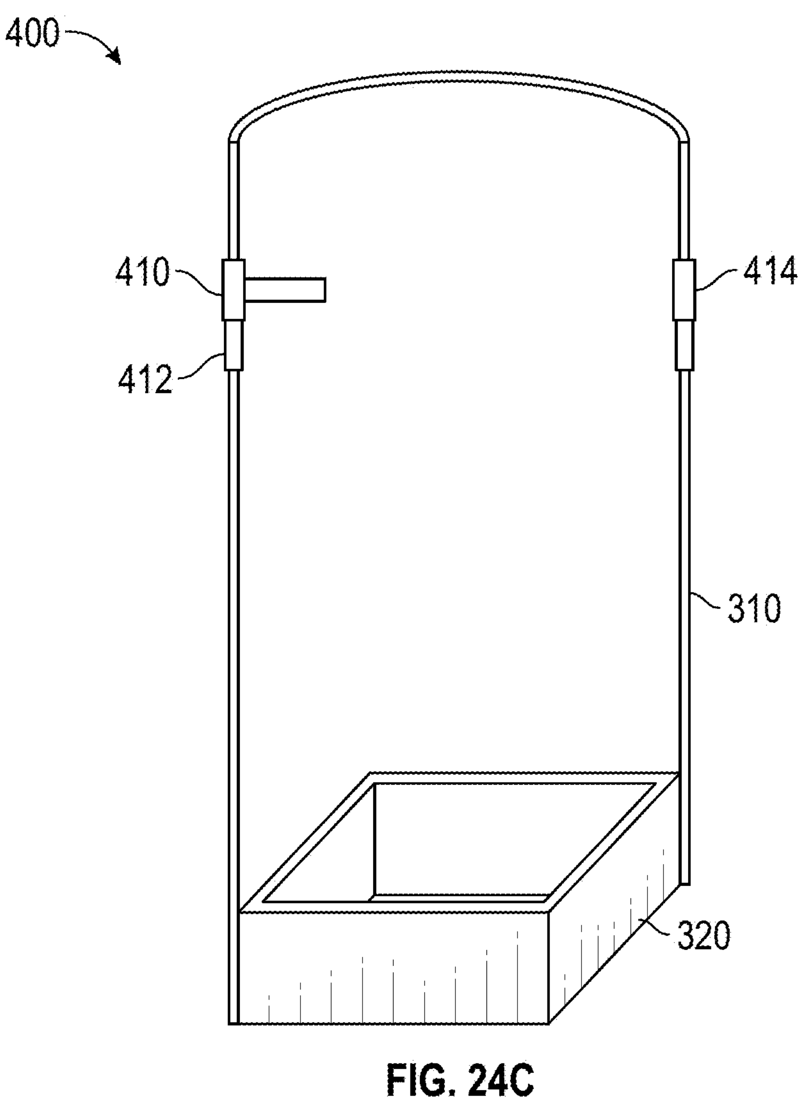
FIG. 24C illustrates a tubular sleeve in a fully expanded configuration with a sterile adapter.

FIG. 24B illustrates a tubular sleeve 310 in a partially folded configuration. The tubular sleeve 310 is partially unfolded from the cuff 320 while a portion is partially folded around the cuff 320. It is noted that the sleeve 310 and the cuff 320 can have any number of shapes or configurations. FIG. 24C illustrates a tubular sleeve 310 in a fully unfolded or expanded configuration with a distal attachment assembly including a first component 412 and second component 414 to receive and attach the sterile adapter 410 to the drape 300 (described in further detail below). The unfolding of the accordion or telescoping folds allows the tubular sleeve 310 to remain sterile. This folding pattern also allows the tubular sleeve 310 to be partially unfolded while the remainder of the tubular sleeve 310 remains folded on the cuff 320.

FIG. 25 illustrates an alternative tubular sleeve 310 without a cuff. The tubular sleeve 310 may be folded in an accordion or telescoping fashion over itself, similar to the tubular sleeve 310 of FIGS. 24A-C.

FIGS. 26A-26C illustrates draping a tubular sleeve 310 over a robotic arm 210.

FIG. 26A illustrates the tubular sleeve 310 in a folded configuration aligned with and positioned over a distal end of the robotic arm 210. The cuff 320 is configured to hold open the tubular sleeve 310, which allows the tubular sleeve 310 to be aligned to receive the robotic arm 210 in the folded configuration.

FIG. 26B illustrates the tubular sleeve 310 in a partially unfolded configuration, such that the tubular sleeve 310 is draped in a downward motion as the tubular sleeve 310 is partially unfolded in a proximal direction or downward direction over the robotic arm 210.

FIG. 26C illustrates the tubular sleeve 310 in a further unfolded configuration, where the tubular sleeve 310 is unfolded further to drape the robotic arm 210 in a downward or proximal direction over the robotic arm 210. As the tubular sleeve 310 is unfolded from the accordion or telescoping folds about the cuff 320, the cuff 320 moves downward towards the proximal end of the robotic arm 210 until the tubular sleeve 310 covers the robotic arm 210 and the cuff 320 is positioned at a proximal end of the robotic arm 210.

As shown, the unfolding of the tubular sleeve 310 in this manner allows the tubular sleeve 310 to drape the robotic arm 210 in a controlled manner, which prevents the distal end of the tubular sleeve 310 from folding or flopping in an undesired manner as the robotic arm 210 maintains the position of the tubular sleeve 310. Furthermore, the cuff 320 holds open the proximal end of the tubular sleeve 310 as the tubular sleeve 310 is unfolded over the robotic arm 210. The cuff 320 also holds the base or the proximal end of the tubular sleeve 310 open, thereby supporting the top of the tubular sleeve 310 and making it easier to guide the robot arm into the opening of the tubular sleeve 310. Advantageously, as the tubular sleeve 310 is being placed over a robotic arm 210, the tubular sleeve 310 will not be unnecessarily stretched out whereby it could fall into a contaminated zone. The shape, structure, and folded pattern helps control the tubular sleeve 310 even though the tubular sleeve 310 is very long relative to its width to accommodate the shape of the robotic arm 210.

Figure 27:
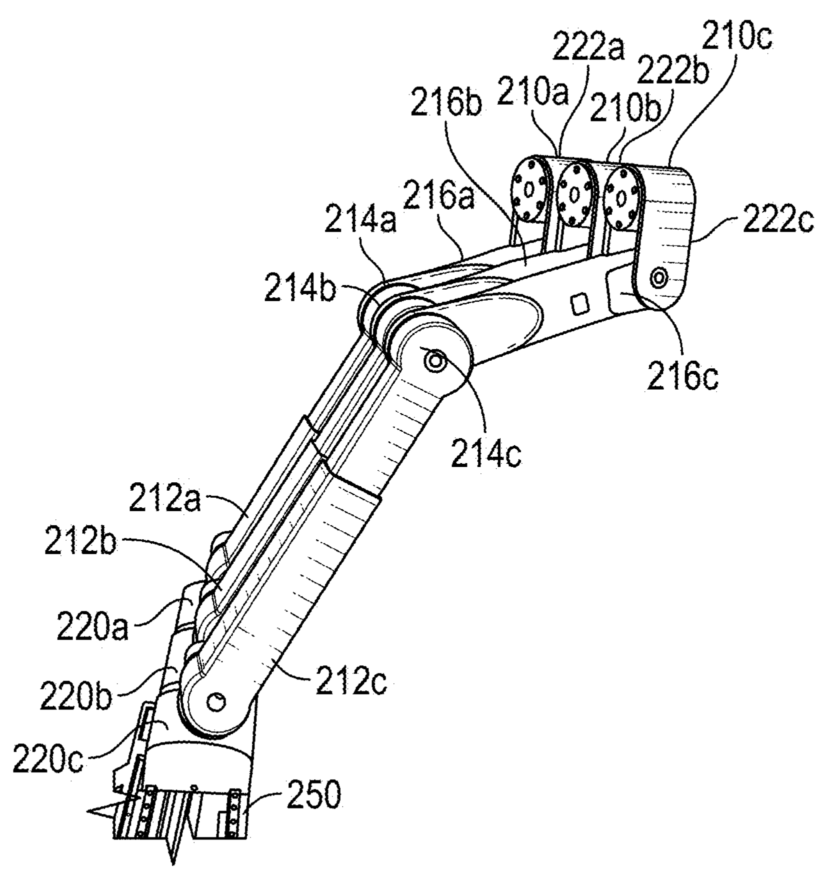
FIG. 27 illustrates a plurality of robotic arms in a draping pose.

FIG. 27 illustrates a plurality of robotic arms 210 in a draping pose. FIG. 27 includes a plurality of three robotic arms 210*a*, 210*b*, 210*c*. In the draping pose, the plurality of robotic arms 210*a*, 210*b*, 210*c* are directed generally upwards. As shown, the distal ends 216*a*, 216*b*, 216*c* of the plurality of robotic arms 210*a*, 210*b*, 210*c* can be positioned the farthest from the adjustable arm support 250. In the drape pose, each robotic arm 210 may be bent at each joint 214 at an angle, which can allow each robotic arm 210 to achieve a desired height to allow a user to reach the distal end 216 of the robotic arm 210 as well as the desired configuration and position for draping the robotic arm 210.

In some examples, a drape assembly 300 includes two, three, or more tubular sleeves 310 that are coupled together to go over two, three, or more robotic arms 210. The drape assembly 300 can include any number of pockets, which can correspond to a plurality of robotic arms 210. In this design, the open end of the tubular sleeves 310 can be connected to a drape for the remainder of the robotic system, such as the adjustable arm support 250.

Figure 28A:
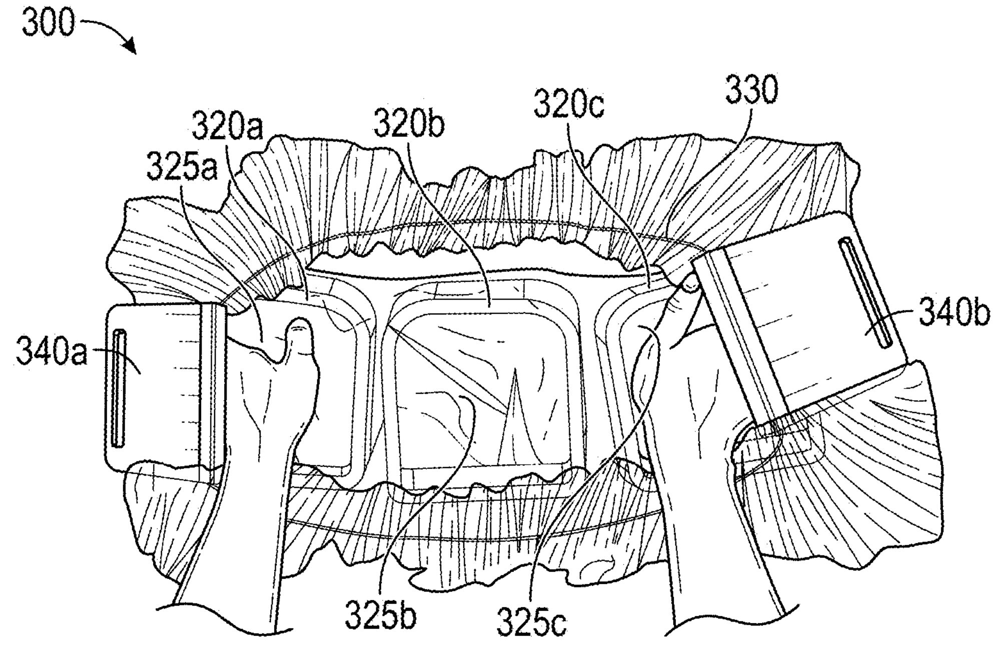
FIG. 28A illustrates a drape with a plurality of pockets.

FIG. 28A illustrates a drape or drape assembly 300 with a plurality of pockets including three pockets 325*a*, 325*b*, 325*c*. Each pocket 325 is formed by a tubular sleeve 310 that is folded in an accordion or telescoping fashion over a respective cuff 320 as described herein. Each tubular sleeve 310 can include one or more folds that form a pocket 325 to receive the respective robotic arm 210. The opening or pocket is 325 is further created by the cuff 320 holding open the proximal end of the tubular sleeve 310. Each tubular sleeve 310 can include or form a pocket 325 to receive a respective robotic arm 210.

The drape 300 further includes one or more coupling or attachment components and an elastic member 330 which will be described in more detail below. FIG. 28A illustrates the drape assembly 300 with an elastic member 330 and two attachment components 340*a*, 340*b*.

Figure 28B:
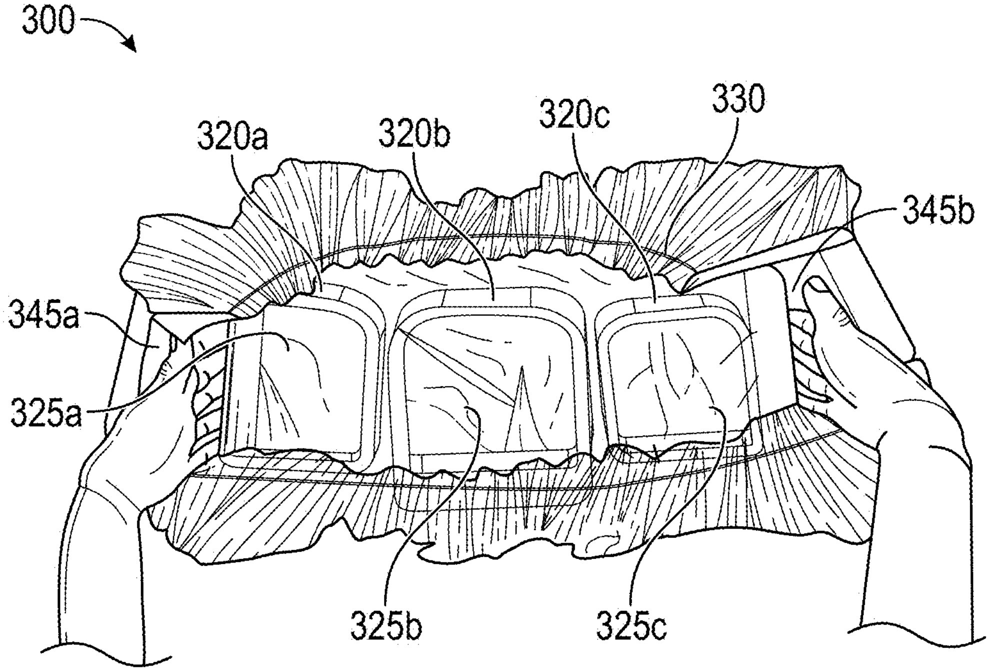
FIG. 28B illustrates a drape with handholds.

The drape assembly 300 can further include one or more hand pockets or handholds. The pockets may be configured to receive a user's hand to enable the user to grip the drape assembly 300 in a designated area. The hand pocket may be defined or formed by a handhold, which may be made of a material stiffer than the drape material. FIG. 28B illustrates a drape 300 with two hand pockets formed by two handholds 345*a*, 345*b*. In other examples, the drape 300 can include any number of handholds, such as zero, one, two or more handholds 345. The handholds 345*a*, 345*b* allow a user to grip the drape 300 at a designated portion to prevent contamination of the remainder of the drape 300. The handholds 345*a*, 345*b* also allow the user to grip and carry the drape 300 to transport the drape 300 to the robotic arms 210 for draping. The handholds 345*a*, 345*b* may be positioned at either end of the drape 300 to allow a user to hold the drape 300 at positions for better control of the entire drape 300, ease of transport of the drape 300, and to avoid contamination of the drape 300. The handholds 345*a*, 345*b* may be positioned away on either side of the pockets 325*a*, 325*b*, 325*c*. The user can place his or her hands in the pocket to grip the handholds 345 on each side of the drape 300 to enable easily transfer the drape 300 into position.

Figure 29A:
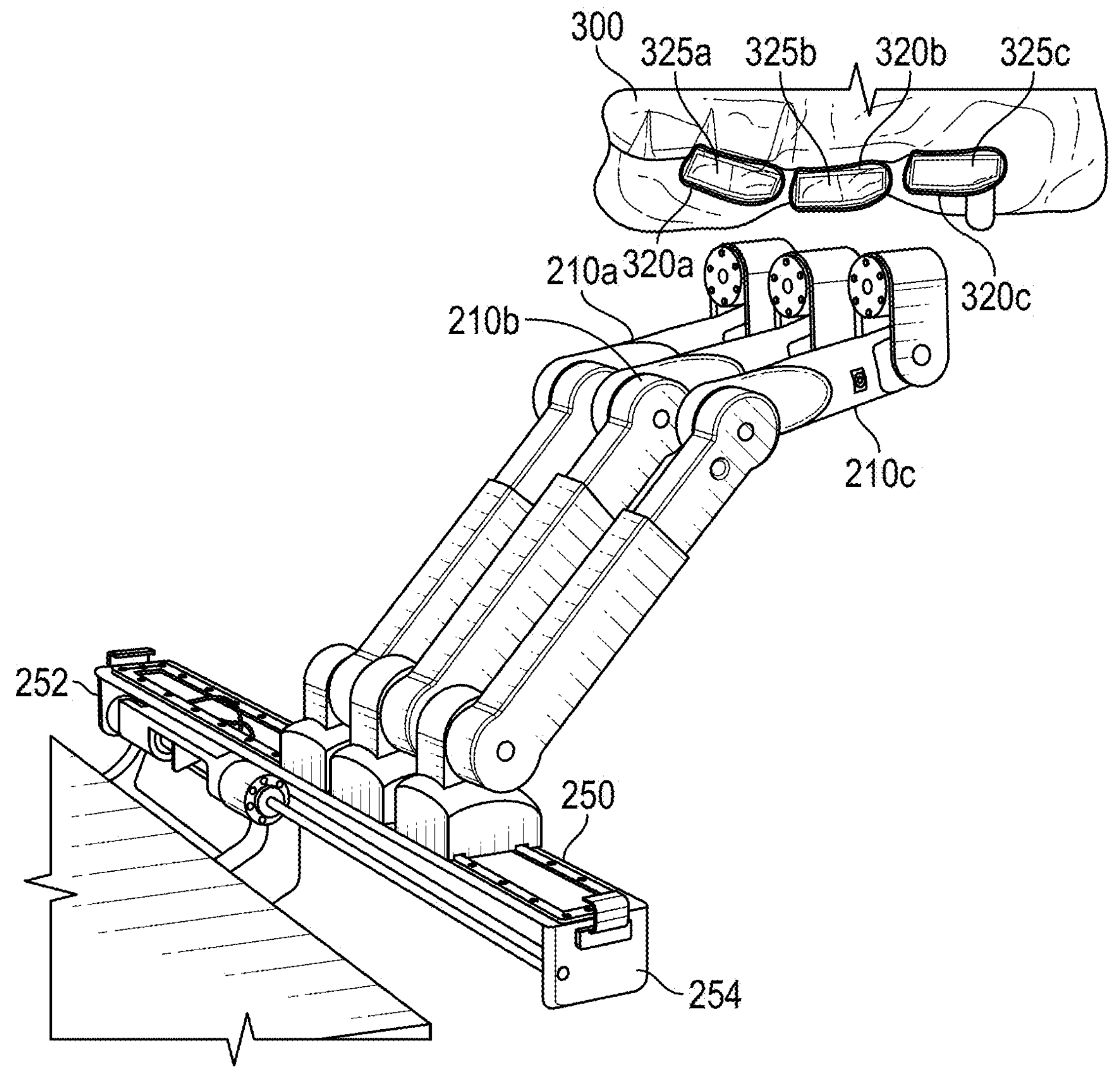
FIG. 29A illustrates a drape aligned over the plurality of arms.

FIG. 29A illustrates the drape 300 aligned with and positioned over the plurality of arms 210*a*, 210*b*, 210*c*. The drape 300 can include any number of pockets 325, such as the three pockets 325*a*, 325*b*, 325*c* shown in FIG. 29A. The drape 300 can be positioned to align the respective pockets 325 of the plurality of tubular sleeves 310 with the corresponding robotic arms 210 while in the drape pose. The drape 300 may be aligned over the plurality of arms 210*a*, 210*b*, 210*c* such that the first pocket 325*a* is positioned over the first robotic arm 210*a*, the second pocket 325*b* is positioned over the second robotic arm 210*b*, the third pocket 325*c* is positioned over the third robotic arm 210*c*. Each robotic arm 210 can be configured to be inserted upwardly into the pocket 345 of each tubular sleeve 310.

Figure 29B:
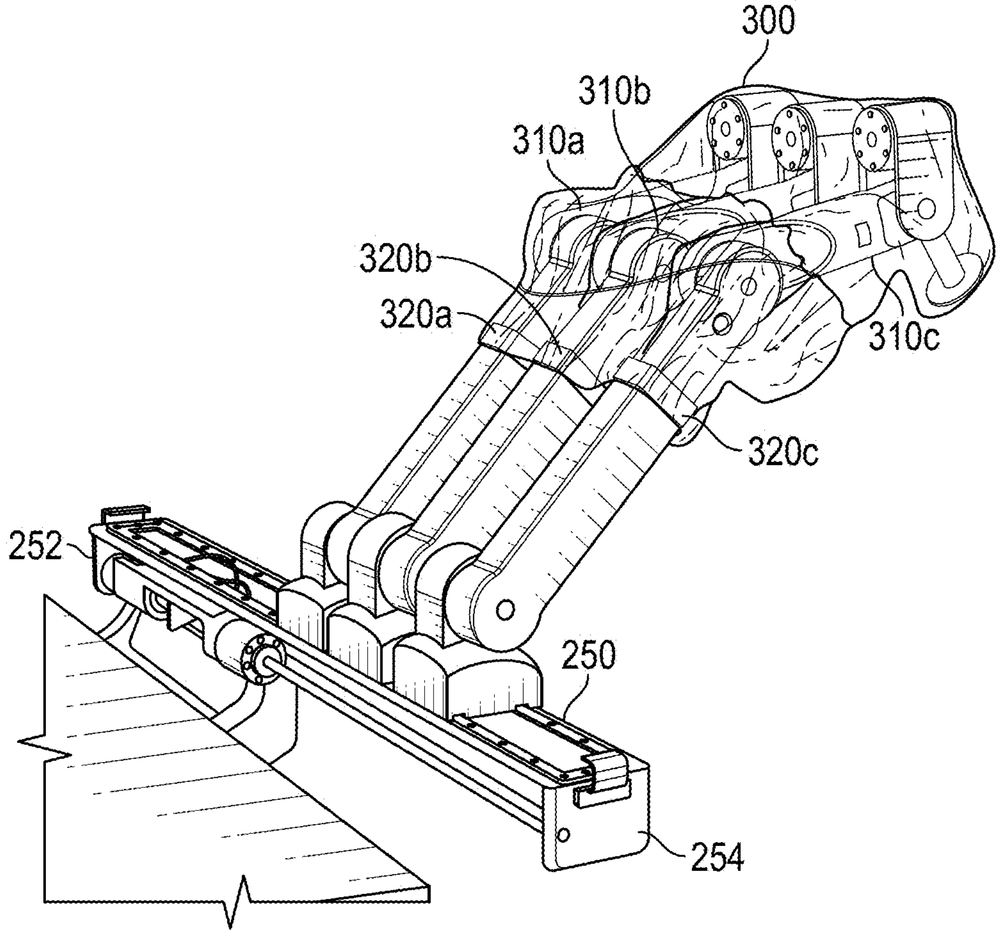
FIG. 29B illustrates the drape partially covering the plurality of arms.
Figure 29C:
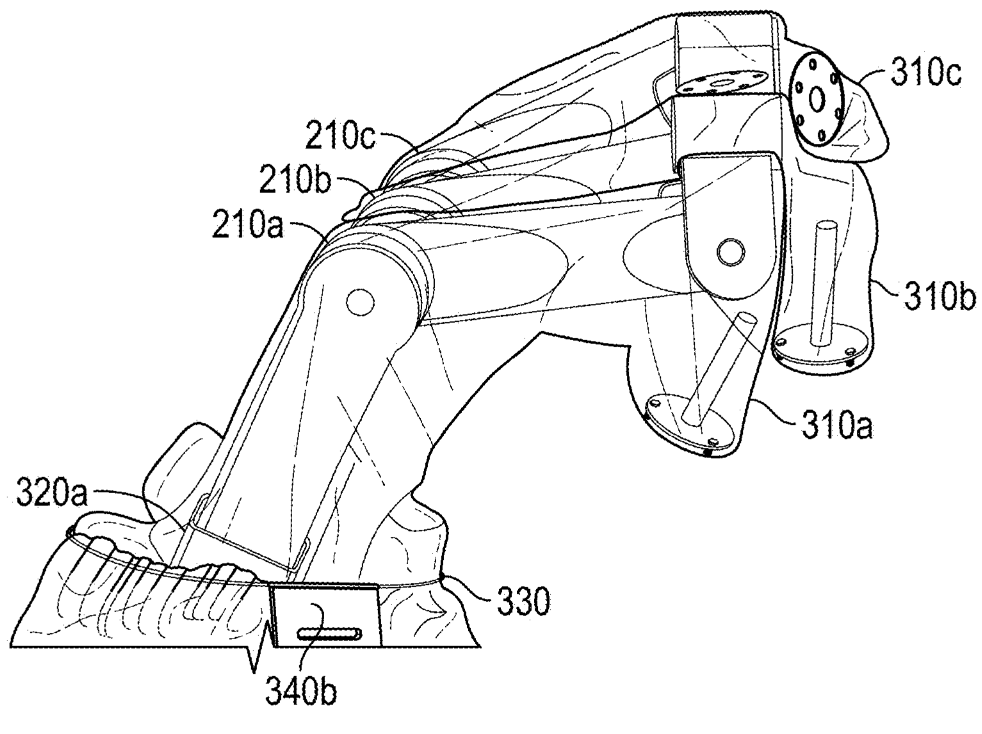
FIG. 29C illustrates the drape completely covering the plurality of arms.

FIG. 29B illustrates the drape 300 partially unfolded to cover a portion of the plurality of robotic arms 210*a*, 210*b*, 210*c*. FIG. 29C illustrates the drape 300 unfolded to cover the entirety of the plurality of robotic arms 210*a*, 210*b*, 210*c*.

As shown, the pockets 345*a*, 345*b*, 345*c* are unfolded as tubular sleeves 310*a*, 310*b*, 310*c* over each robotic arm 210*a*, 210*b*, 210*c*. Each tubular sleeve 310*a*, 310*b*, 310*c* is configured to be, in use, unfolded downwardly over the respective robotic arm 210*a*, 210*b*, 210*c*. Each tubular sleeve 310*a*, 310*b*, 310*c* is configured to be downwardly draped over the respective robotic arms 210*a*, 210*b*, 210*c*.

At the end of the process of draping the plurality of robotic arms 210 (such as the method 500 described herein), each robotic arm 210 will be surrounded and draped by a tubular sleeve 310. In addition to being used to drape the plurality of robotic arms 210, the drape assembly 300 can also be used to drape one or more adjustable arm supports, as described below.

B. Draping Adjustable Arm Support

The adjustable arm support 250 (which may also be called a rail, bar, or base) supports one or more robotic arms 210. The adjustable arm support 250 can be draped or covered, which may be useful such that the adjustable arm support 250 can be kept sterile. For example, the adjustable arm support 250 can be positioned in a sterile field when used in a procedure or may be covered during transport.

The drape assembly 300 can include the one or more tubular sleeves 310 to cover the one or more robotic arms 210. The drape assembly 300 can further include a rail/bar drape or drape portion 350 to cover or surround the adjustable arm support 250. The tubular sleeves 310 and drape portion 350 can be integral or separate portions. The drape portion 350 can be connected to the distal open ends of the tubular sleeves 310.

i. Length

It is noted that the rail drape or drape portion 350 can accommodate the movement of the robotic arms 210 along the adjustable arm support 250. Therefore, the drape portion 350 can be a much greater length than the length of the adjustable arm support 250.

Figure 30:
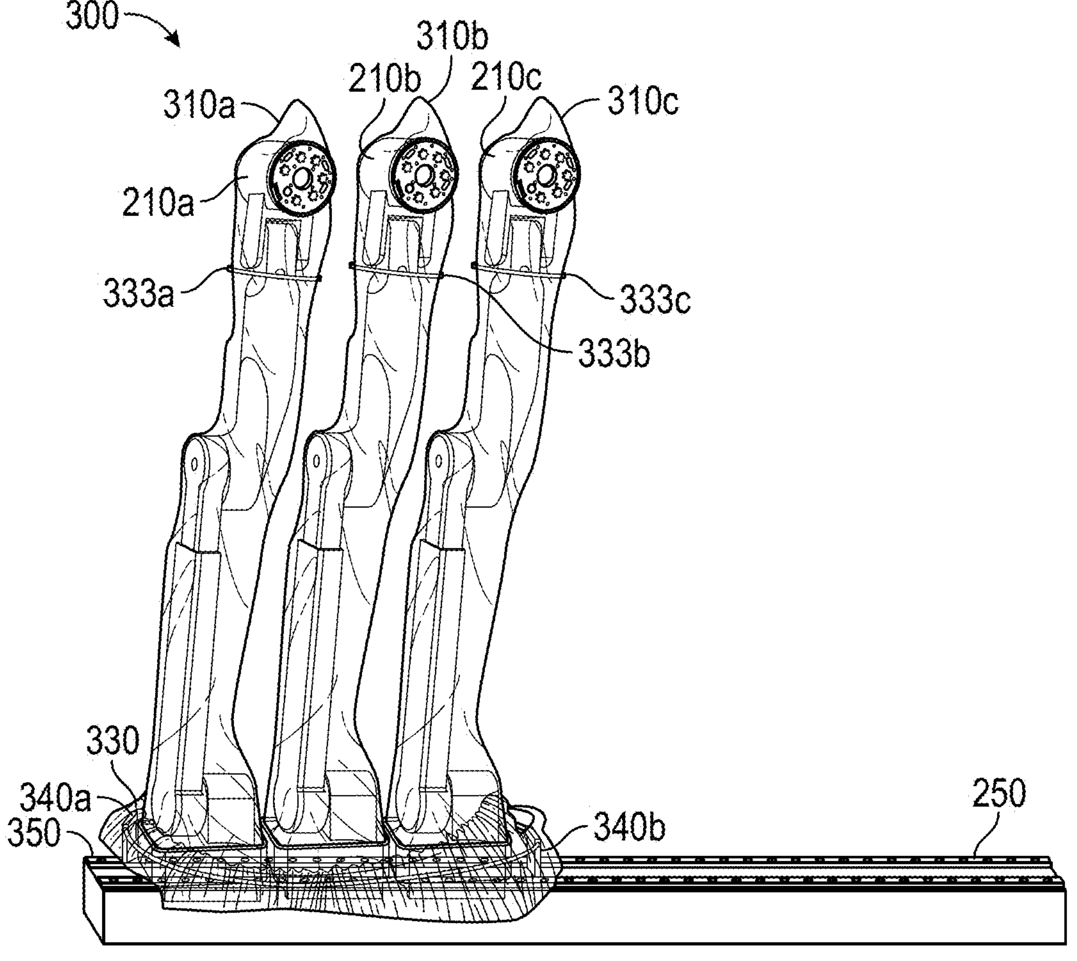
FIG. 30 illustrates a drape covering the plurality of arms and the adjustable arm support undraped.

FIG. 30 illustrates the drape 300 covering the plurality of robotic arms 210 and the adjustable arm support 250 undraped. The drape 300 can be configured to cover one or more robotic arms 210, such as at least two robotic arms 210 or the three robotic arms 210*a*, 210*b*, 210*c*, as shown in FIG. 30. The at least two robotic arms 210 can be configured to translate relative to one another.

Figure 31A:
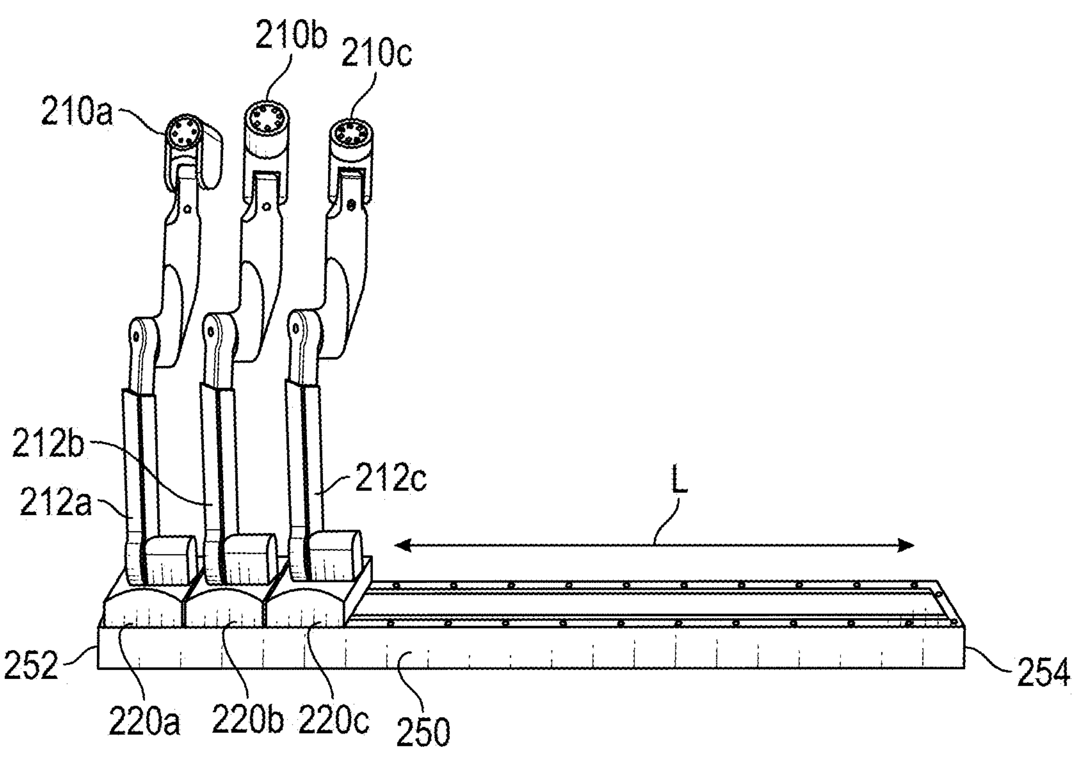
FIG. 31A illustrates three robotic arms positioned on a first end of the adjustable arm support.
Figure 31B:
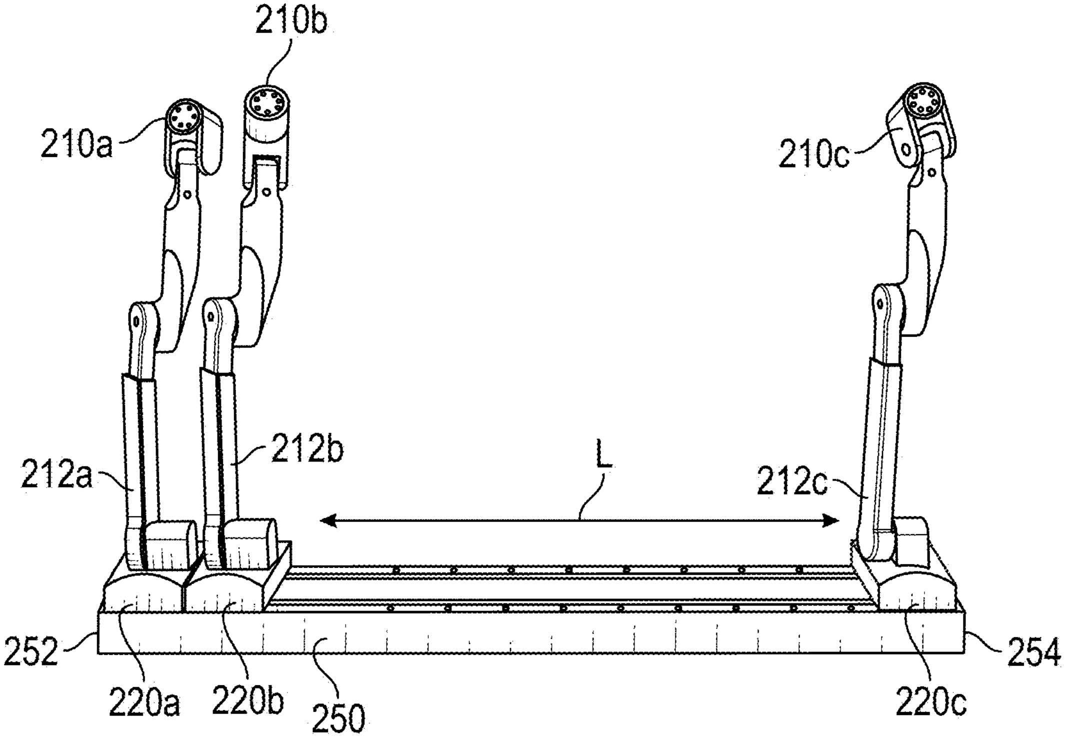
FIG. 31B illustrates two robotic arms positioned on the first end of the adjustable arm support and one robotic arm positioned on the second end of the adjustable arm support.
Figure 31C:
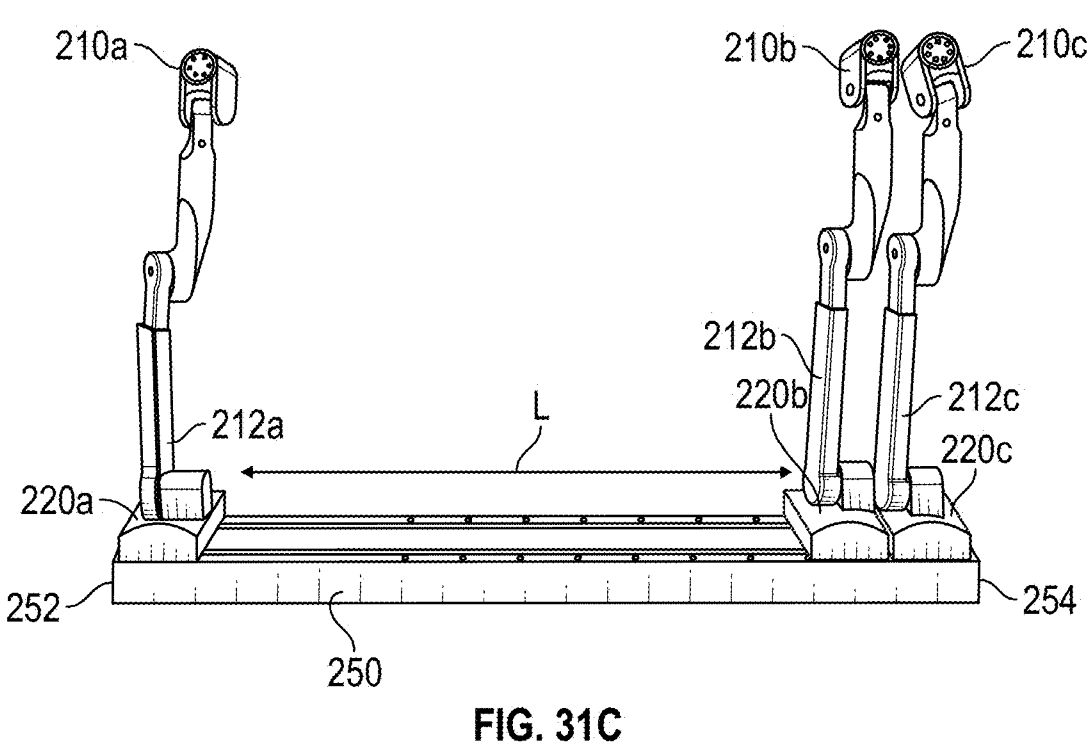
FIG. 31C illustrates one robotic arm positioned on the first end of the adjustable arm support and two arms positioned on the second end of the adjustable arm support.

FIGS. 31A-31C show various positions of the plurality of robotic arms 210 along the length of the adjustable arm support 250. FIGS. 31A-31C show the maximum range of the plurality of robotic arms 210 along the length of the adjustable arm support 250 that the drape portion 350 accommodates. As shown, the maximum distances between the possible positions of the arms 210 are a length "L." The plurality of robotic arms 210 may be positioned in other positions along the length of the adjustable arm support. For example, FIGS. 21 and 22A-22B show the plurality of robotic arms 210 in a different configuration.

FIG. 31A illustrates three robotic arms 210*a*, 210*b*, 210*c* positioned on a first end 252 of the adjustable arm support 250. As shown, with the three robotic arms 210*a*, 210*b*, 210*c* positioned on one end of the adjustable arm support 250, the remainder of the adjustable arm support 250 that can be draped (length "L") is approximately the length of the adjustable arm support 250. Therefore, the end of the drape portion 350 extending from where the tubular sleeves 310 connect to the drape portion 350 to the second end 254 should have a length of approximately "L."

Figure 31D:
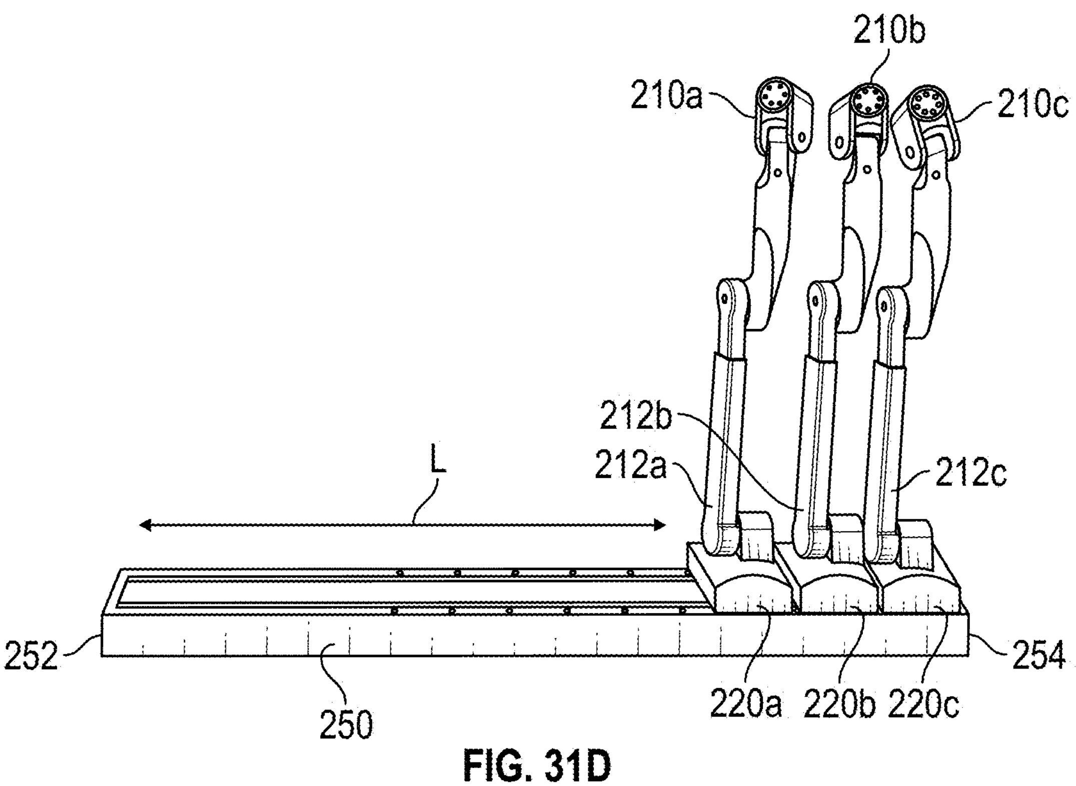
FIG. 31D illustrates three arms positioned on the second end of the adjustable arm support.

FIG. 31D illustrates three arms 210*a*, 210*b*, 210*c* positioned on the second end 254 of the adjustable arm support 250. Similar to FIG. 31A, as the three robotic arms 210*a*, 210*b*, 210*c* are positioned on the opposite end 254 of the adjustable arm support 250, the remainder of the adjustable arm support 250 that can be draped (length "L") is approximately the length of the adjustable arm support 250. Therefore, the end of the drape portion 350 extending from where the tubular sleeves 310 connect to the drape portion 350 to the first end 252 can also have a length of approximately "L." Therefore, each end of the drape portion 350 can have a length of approximately "L" at both ends, which extend on either side from the portion where the tubular sleeves 310 connect to the drape portion 350.

FIG. 31B illustrates two robotic arms 210*a*, 210*b* positioned on the first end 252 of the adjustable arm support 250 and one robotic arm 210*c* positioned on the second end 254 of the adjustable arm support 250. As shown, with the two robotic arms 210*a*, 210*b* positioned on one end of the adjustable arm support 250 and one robotic arm 210*c* positioned on the opposite end of the adjustable arm support, the area of the adjustable arm support 250 between the second robotic arm 210*b* and the third robotic arm 210*c* which can be draped (length "L") is approximately the length of the adjustable arm support 250. Therefore, the area of the drape portion 350 between the second robotic arm 210*b* and the third robotic arm 210*c* can have a length of approximately "L."

FIG. 31C illustrates one robotic arm 210*a* positioned on the first end 252 of the adjustable arm support 250 and two arms 210*b*, 210*c* positioned on the second end 254 of the adjustable arm support 250. As shown, with the one robotic arm 210*a* positioned on one end of the adjustable arm support 250 and two robotic arms 210*b*, 210*c* positioned on the opposite end of the adjustable arm support, the area of the adjustable arm support 250 between the first robotic arm 210*a* and the second robotic arm 210*b* which can be draped (length "L") is approximately the length of the adjustable arm support 250. Therefore, the area of the drape portion 350 between the first robotic arm 210*a* and the second robotic arm 210*b* can have a length of approximately "L."

As the at least two robotic arms 210 are slidable relative to each other along the adjustable arm support 250, the drape 300 can include a drape portion 350 to cover the adjustable arm support 250 to drape an area between the at least two tubular sleeves 310, as well as the ends of the adjustable arm support 250. The area between the at least two tubular sleeves 310 can approximately correspond to a length of the adjustable arm support 250. The drape portion 350 can have a length between tubular sleeves 310 that is approximately the length of the adjustable arm support 250. When there are more than two robotic arms 210, the drape portion 350 can cover each area between each of the robotic arms 210.

Figure 32A:
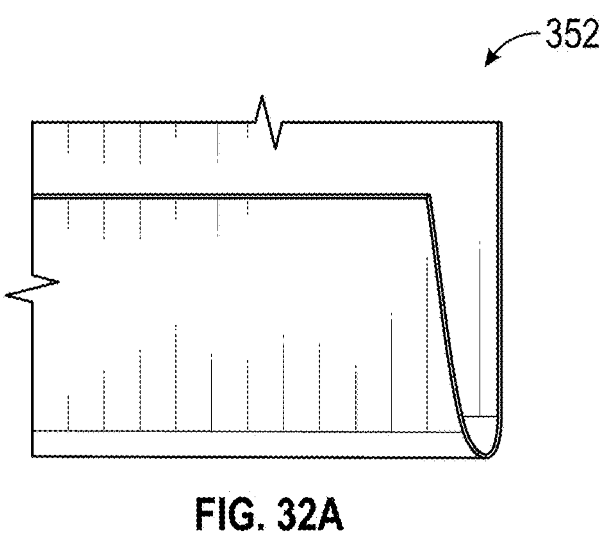
FIG. 32A illustrates an example folded hem of the drape.
Figure 32B:
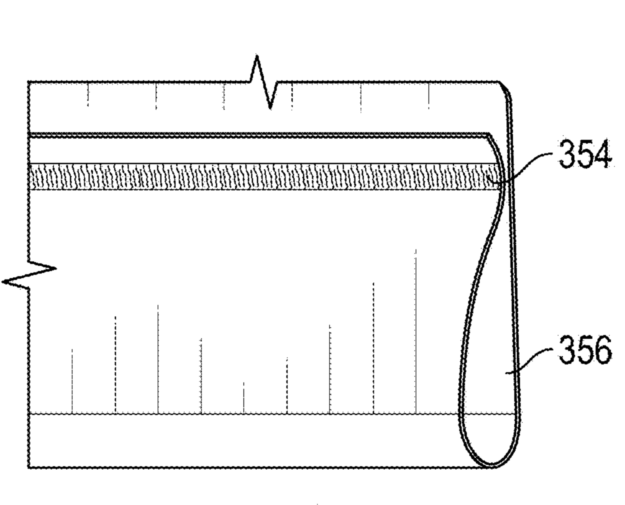
FIG. 32B illustrates the folded hem of the drape heat sealed.
Figure 32C:
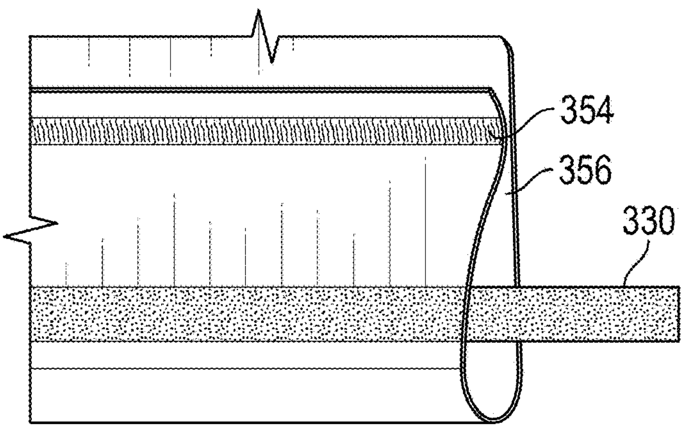
FIG. 32C illustrates the elastic member inserted into the folded hem.

The drape portion 350 can be long enough to cover the adjustable arm support 250 in its entirety or along its entire length, as well as accommodate movement of the slidable robotic arms 210 along the adjustable arm support 250. In some examples, the drape portion 350 is approximately a multiple of a longitudinal length of the adjustable arm support 250. The drape portion 350 can have a length of at least two, three, four, five, or more times a length of the adjustable arm support 250. For example, for the adjustable arm support 250 with three robotic arms 210*a*, 210*b*, 210*c* as shown in FIGS. 32A-D, the drape portion 350 can be at least four times the length of the adjustable arm support 250. The drape portion 350 covering the adjustable arm support 250 can cover: (1) a maximum length between the third robotic arm 210*c* and the second end 254 (as shown in FIG. 32A), (2) a maximum length between the second robotic arm 210*b* and the third robotic arm 210*c* (as shown in FIG. 32B), (3) a maximum length between the first robotic arm 210*a* and the second robotic arm 210*b* (as shown in FIG. 32C), and (4) a maximum length between the first end 252 and the first robotic arm (as shown in FIG. 32D). Therefore, the drape portion 350 having a length that is multiple times (and in some cases, several times) the length of the adjustable arm support 250 as described can accommodate the full range of motion of the robotic arms 210.

The multiple of the longitudinal length of the adjustable arm support 250 can be based on the number of arms 210 mounted on the adjustable arm support 250. The entire length required for the drape portion 350 to cover the adjustable arm support 250 can be (n+1)(L) where n is the number of robotic arms and L is the length of the adjustable arm support 250. This equation is used to approximate the length of the drape portion 350 to cover the adjustable arm support 250 for simplicity.

However, while the (n+1)(L) equation is used for simplicity, the length of the drape portion 350 can be more exactly calculated. More precisely, the length of the adjustable arm support 250 to be draped beyond the robotic arms 210 is not same length of the adjustable arm support 250 as estimated above. Rather, the required length of the adjustable arm support 250 draped beyond the robotic arms 210 is the entire length of the adjustable arm support 250 minus the length of the carriage 220 of each of the robotic arms 210.

For example, as shown in FIG. 32A, the length of the adjustable arm support to be draped from the third robotic arm 210*c* to the second end 254 of the adjustable arm support 250 is not the entire length of the adjustable arm support 250 as approximated, rather the length of the adjustable arm support to be draped is the length of the adjustable arm support 250 minus the length of the carriage 220 of each of the robotic arms 210*a*, 210*b*, 210*c*. The length of the drape portion 350 can also cover each arm base, which is located at the proximal end 212 of each robotic arm 210. The length of each arm base may be substantially the same as the length (or diameter) of each tubular sleeve opening. Therefore, the exact formula for the entire length of the drape portion 350 is:

$$(n+1)\times(\text{length of adjustable arm support}-(n\times\text{length of carriages}))+(n\times\text{length of arm base})$$

where n is the number of robotic arms.

ii. Elastic Member and Hem

The material on the adjustable arm support 250 can be gathered in a manner that allows full movement of the robotic arms 210 without the drape portion 350 lifting off the adjustable arm support or falling and touching unsterile surfaces.

To prevent the drape 300 from lifting off the adjustable arm support 250, during use, the adjustable arm support 250 is covered using a drape with a drape portion 350 with dimensions greater than the dimensions of the adjustable arm support 250. Furthermore, the drape portion 350 may have a length significantly longer than the adjustable arm support 250 to accommodate the motion of the robotic arms along the adjustable arm support, as described above. However, with larger dimensions of the drape 350, there is an increased risk of contamination of the drape 350. Therefore, the drape 300 can be designed to avoid contamination but also prevent the drape 300 from lifting off the adjustable arm support 250. The drape portion 350 may be gathered at the bottom of the drape portion 350 with an elastic member.

The drape portion 350 can have an elastic member that can be located in a hem of the drape. The hem can be positioned at a bottom edge or end of the drape portion 350 and can receive the elastic member. FIG. 32A illustrates a folded hem 352 of the drape 300. As shown, the drape material may be folded over itself. FIG. 32B illustrates the folded hem 352 of the drape 300 with a heat seal 354. To form the folded hem 352, the drape material is folded over and heat sealed to form a pocket 356 of the hem 352. The hem 352 is formed by folding a bottom portion of the drape 300.

FIG. 32C illustrates the elastic member 330 inserted into or threaded into the pocket 356 of the hem 352. The elastic member 330 is threaded through the hem 352 at the bottom portion of the drape portion 350 to form an elastic cuff 330, whereby drape material slides over or relative to the elastic member 330 during use, rather than pulling upward off the adjustable arm support 250. Furthermore, particular materials may be used to further enable the sliding motion of the drape material relative to the elastic member 330. In some examples, the material of the drape is polyurethane (PU) and the type of elastic may be fabric covered. The material of the drape and type of elastic can be selected to minimize friction, such that the drape slides over the elastic in a shower-curtain or sliding fashion to prevent the drape material from lifting off the adjustable arm support 250.

Figure 33:
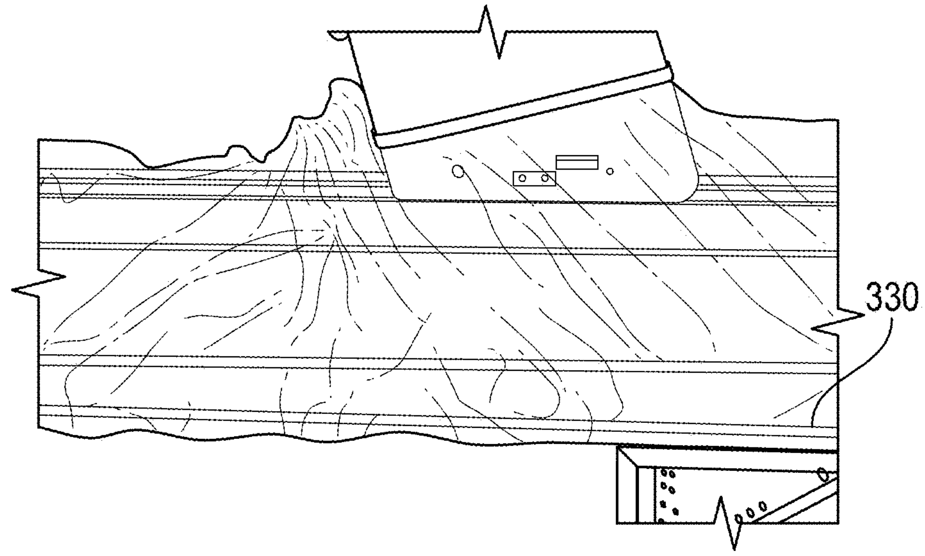
FIG. 33 illustrates the elastic member and hem positioned at the bottom surface of the adjustable arm support.

FIG. 33 illustrates the elastic member 330 within the hem 352, positioned at the bottom surface of the adjustable arm support 250. The bottom portion of the drape 300 can be positioned on a bottom surface of the adjustable arm support 250. The elastic member 330 further also allows the drape portion 350 to be held in place to cover the adjustable arm support 250. The elastic member 330 can extend about or surround the adjustable arm support 250. When draping the adjustable arm support 250, the drape portion 350 can be extended over the adjustable arm support 250 and the elastic member 330 can be positioned at the bottom surface of the adjustable arm support 250.

Figure 34:
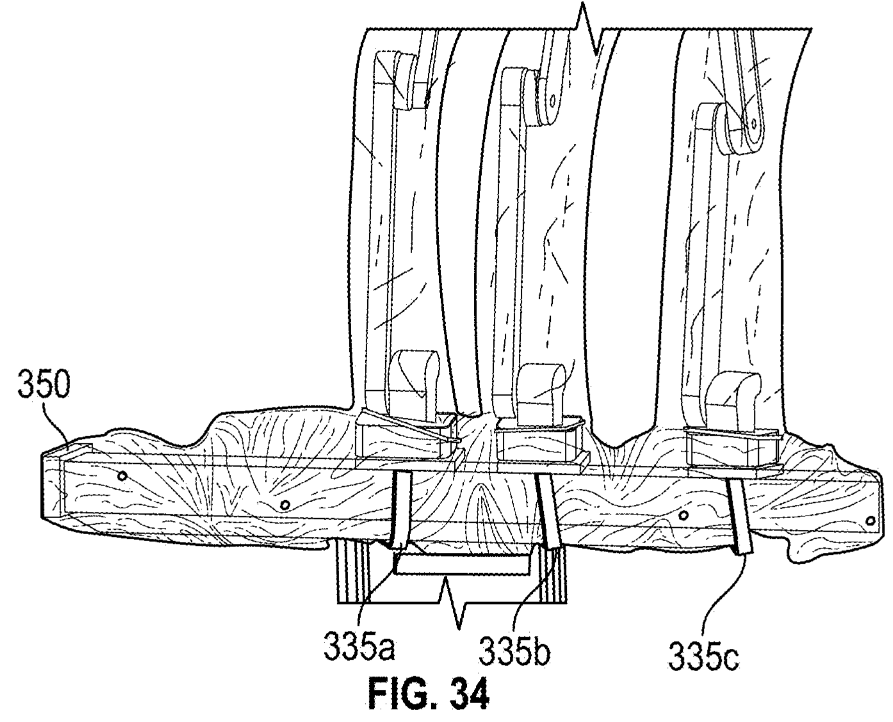
FIG. 34 illustrates another example drape for the adjustable arm support.

FIG. 34 illustrates an alternative of the drape portion 350 of the adjustable arm support 250. As shown, the drape portion 350 may be held in place by one or more extensions or clamps 335*a*, 335*b*, 335*c*. The one or more extensions or clamps 335*a*, 335*b*, 335*c* may be used in addition to or instead of elastic members 330 (as shown in FIG. 33). The extensions 335 may be positioned anywhere along the length of the adjustable arm support 250. The extensions 335 may be positioned around the sides of the adjustable arm support 250. For example, the extensions 335 may be positioned around at least a portion of the bottom surface and the side surfaces of the adjustable arm support. The extensions 335 may not be positioned on the top surface of the adjustable arm support 250 or only positioned on an edge portion of the top surface of the adjustable arm support 250, to thereby allow motion of the carriage 220 of the robotic arms 210 to linearly translate along the top surface of the adjustable arm support 250.

iii. Attachment Coupling

The drape portion 350 can be configured to be placed on the adjustable arm support 250 in a manner that is quick, easy and ensures that the user and draped components of the system remain sterile. The doctor, nurse, or any individual draping the adjustable arm support 250 can avoid touching any portion of the undraped robotic arms 210, the adjustable arm support 250 or the unsterile side of the drape 300 with their gloved, sterile hands.

The drape 300 can include one or more attachment coupling components or members that allows the drape 300 to easily and cost-effectively attach to the adjustable arm support 250, such as an end or side of the adjustable arm support 250. The drape 300 can include two attachment components for coupling to the ends of the adjustable arm support 250.

Figures 35A, 35B:
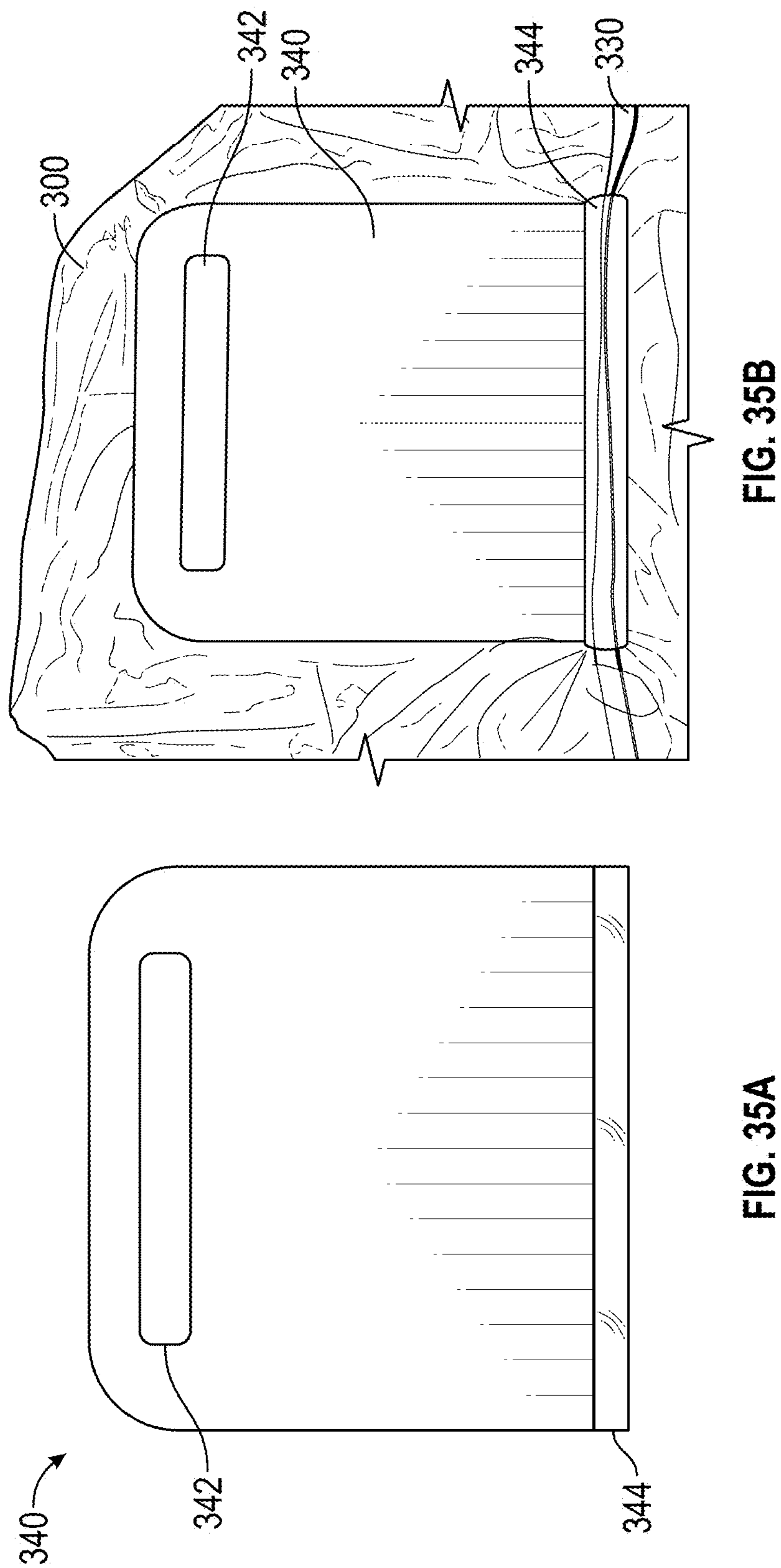
FIG. 35A illustrates an example attachment component.
FIG. 35B illustrates the attachment component connected to a drape.

FIG. 35A illustrates an attachment component 340. FIG. 35B illustrates an attachment component 340 connected to the drape 300. Specifically, the attachment component 340 can be attached to the drape portion 350 which is configured to cover the adjustable arm base 250. The attachment component 340 may be a card as shown in FIGS. 35A-35B. The card may be thin to allow the drape assembly 300 to remain flexible. The attachment component 340 may be approximately the same shape and dimensions as the ends 252, 254 of the adjustable arm support 250. The attachment component 340 may also have a portion 344 that engages with an elastic member 330. The portion 344 may be a tube that receives the elastic member 330. The attachment component 340 may also have a slot 342 that is configured to attach to the adjustable arm support 250.

Figure 36A:
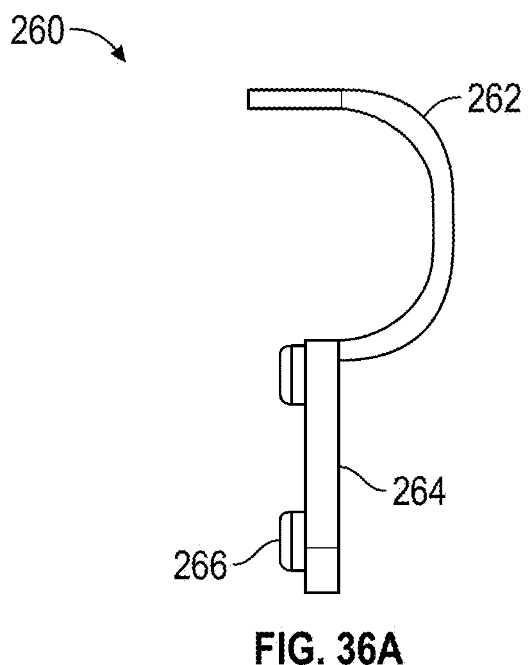
FIGS. 36A-36B illustrate a latch.
Figure 36B:
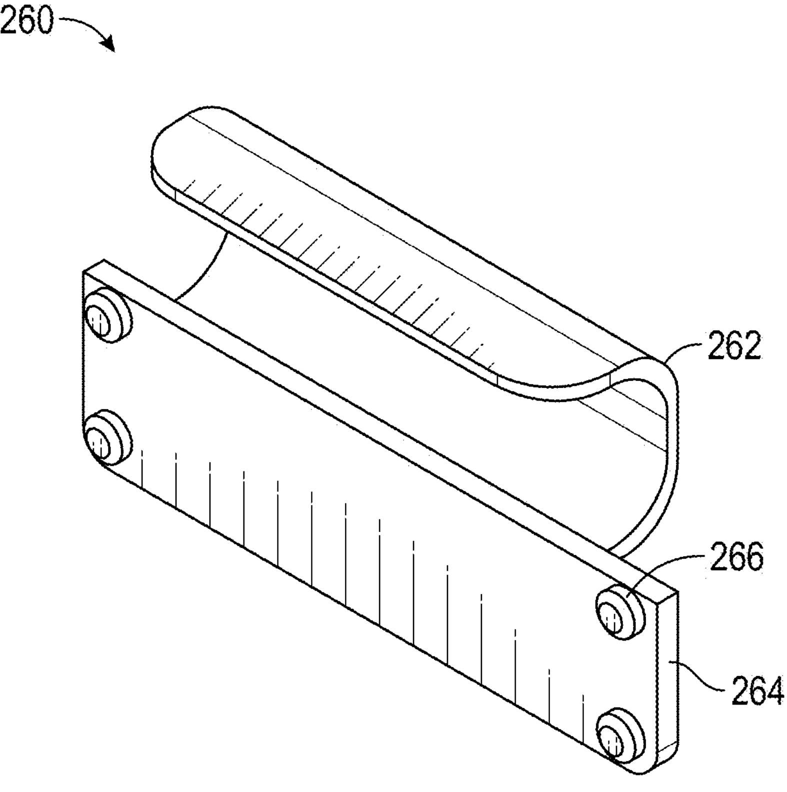

FIGS. 36A-36B illustrates a latch 260. The latch 260 can include a top portion 262 and a bottom portion 264. The top portion 262 may be curved. The bottom portion 264 may be straight and receive one or more fasteners.

Figure 36C:
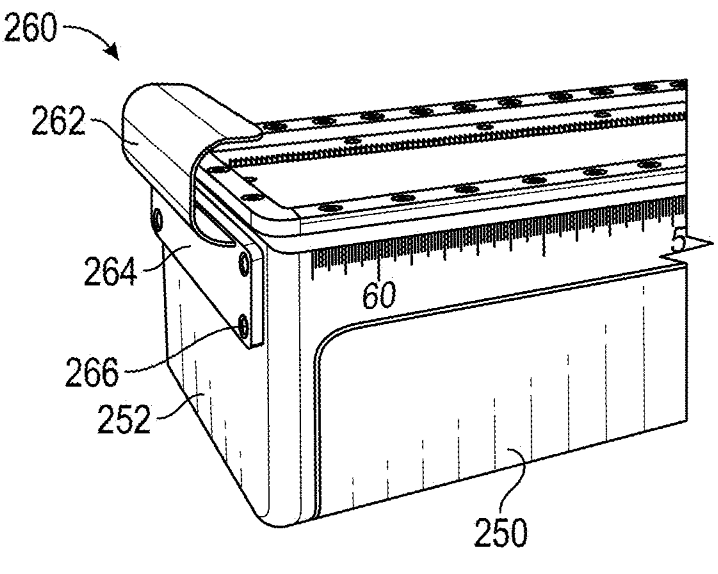
FIGS. 36C-36D illustrate the latch on an end of an adjustable arm support.
Figure 36D:
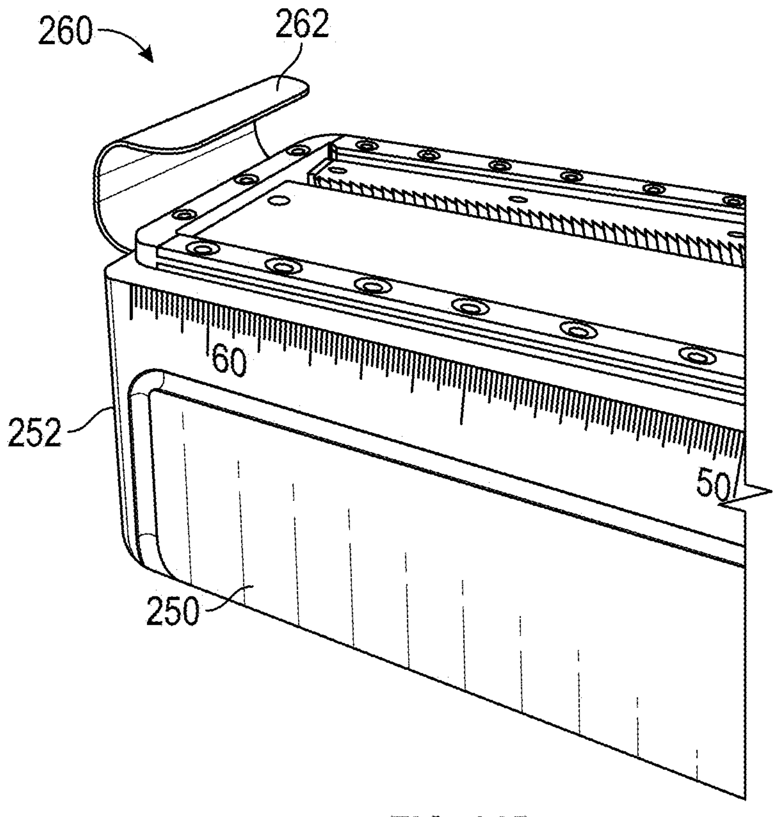

The adjustable arm support 250 can include one or more latches 260 anywhere on the adjustable arm support 250, such as at the ends or the sides of the adjustable arm support 250. In some examples, the adjustable arm support 250 can include a latch 260 on a first end 252 and/or a second end 254 of the adjustable arm support 250. FIGS. 36C-36D illustrates the latch 260 on a first end 252 of the adjustable arm support 250. The latch 260 may be attached to the first end 252 of the adjustable arm support 250 with a plurality of fasteners 266. The latch 260 may be attached such that the bottom portion 264 of the latch 260 is attached to the first end 252 and the curved portion 262 is positioned above the top surface of the adjustable arm support 250. The latch 260 can also be considered a curved bumper or a bumper with the curved portion 262 is positioned above the top surface of the adjustable arm support 250. The latch 260 can be attached to the adjustable arm support 250 with one or more fasteners 266. In some examples, the one or more latches 260 can be integral with the adjustable arm support 250.

The latch 260 of the adjustable arm support 250 and the card 340 of the drape 300 can act as a hook and loop that can easily couple the adjustable arm support 250 and the drape 300.

The attachment component 340 of the drape 300 can be configured to be attached to the latch 260 on the adjustable arm support 250. The slot 342 of the card 340 can receive a portion of the latch 260 on the adjustable arm support 250. The card 340 can include a slot or loop 342 that can receive the curved portion 262 of the latch 260.

Figure 37A:
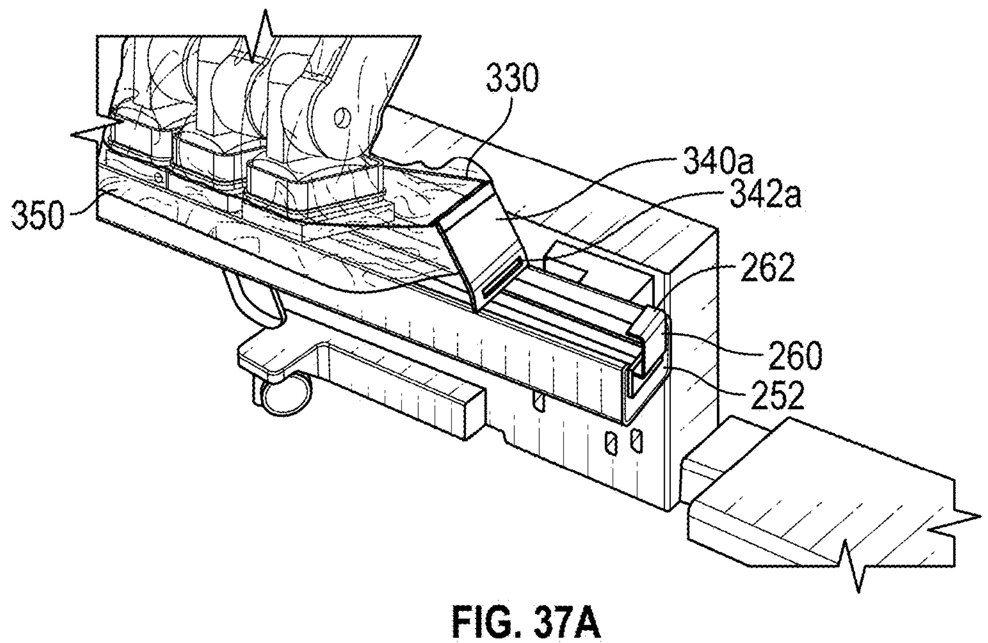
FIGS. 37A-37D illustrate an example process of attaching the attachment component to the latch of the adjustable arm support.
Figure 37B:
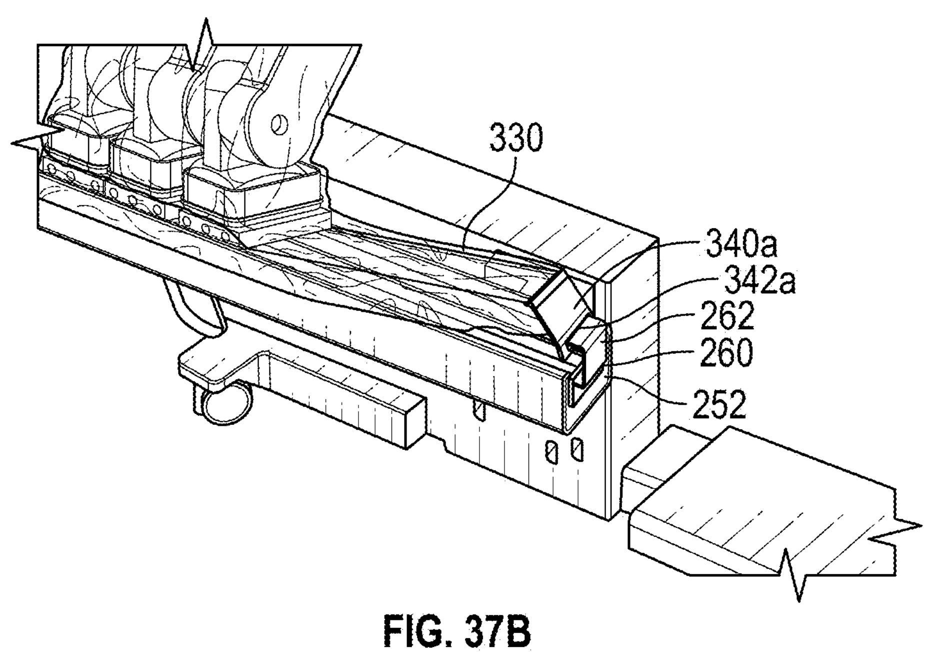
Figure 37C:
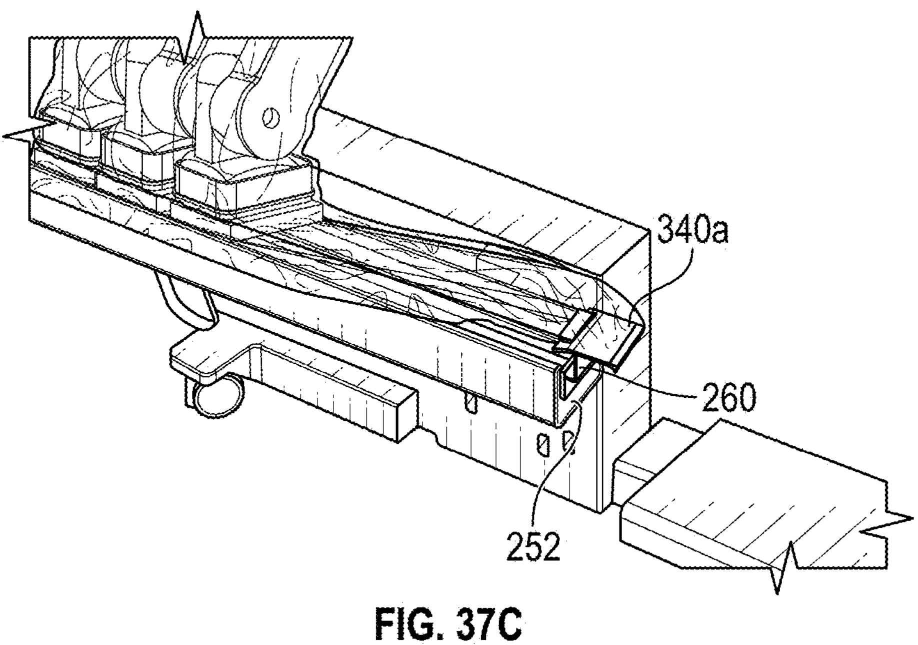
Figure 37D:
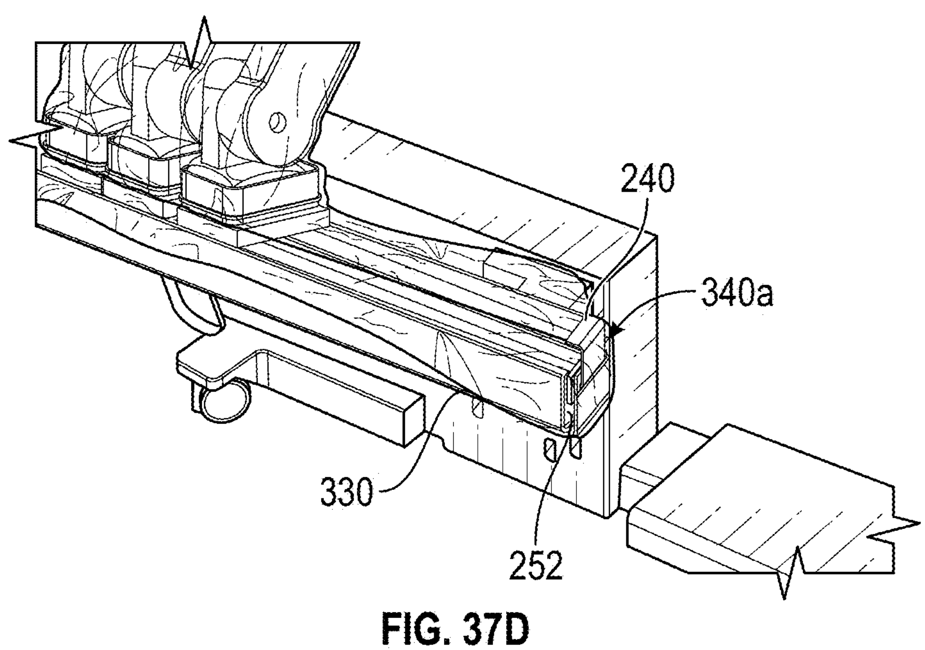

The attachment component 340 can be configured to attach to the adjustable arm support 250. FIG. 37A-37D illustrates the process of attaching the attachment component to the latch of the adjustable arm support. As shown in FIG. 37A, once the robotic arms 210 are draped with the tubular sleeves 310, the card 340*a* of the drape portion 350 is pulled towards the first end 252 of the adjustable arm support 250 to position the card 340*a* near the first end 252 of the adjustable arm support 250. As shown in 37B, once the card 340*a* reaches the first end 252 of the adjustable arm support, the slot 342 of the card or attachment component 340 is aligned with and positioned over the curved portion 262 of the latch 260. A portion of the latch 260, such as the curved portion 262, can be inserted into the slot 342 of the card 340 attached to the drape 300. As shown in 37C, the end of the card 340*a* (opposite the end with the slot 342) is rotated around the curved portion 262 of the latch 260, such that the card 340*a* is stacked on or is positioned side by side with the bottom portion 264 of the latch 260 and the first end 252 of the adjustable arm support 250. The card 340 can be rotated to position the card 340 against the first end 252 of the adjustable arm support 250.

Once in position, the card 340 is attached to the latch 260, such that the drape 300 connected to the card 340 is coupled to the adjustable arm support 250 connected to the latch 260. When the card 340 is rotated into place, the elastic member 330 of the drape portion 350 is positioned at the bottom surface of the adjustable arm support 250 and thus provides tension to keep the attachment component 340 against the end 252 of the adjustable arm support 250. During the draping of the adjustable arm support 250, the user may use the handholds (such as handholds 345 in FIG. 28B) to maneuver the drape assembly 350 in a sterile fashion during draping.

The user is able to advantageously drape the ends 252, 254 of the adjustable arm support 250 quickly, easily, and while keeping their hands isolated from the unsterile adjustable arm support 250. Draping can be considered quick and easy because it can be achieved in a matter of seconds (including 1-second). The ability for a user to keep their hands isolated from the unsterile adjustable arm support begins even when removing the drape 300 from packaging.

This process can be repeated for a second attachment component to drape the second end 254 of the adjustable arm support 250. The process can also be performed to attach one or more cards to one or more latches positioned anywhere on the adjustable arm support 250.

Figure 38A:
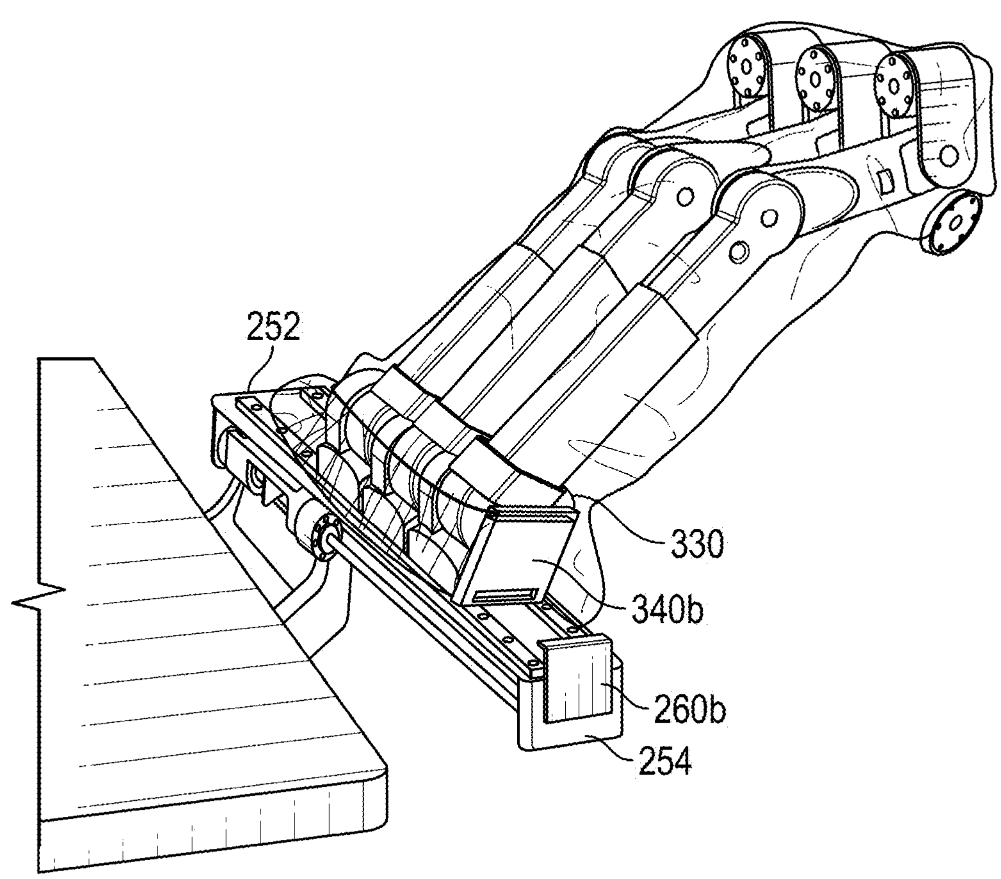
FIG. 38A illustrates both ends of the adjustable arm support undraped.
Figure 38B:
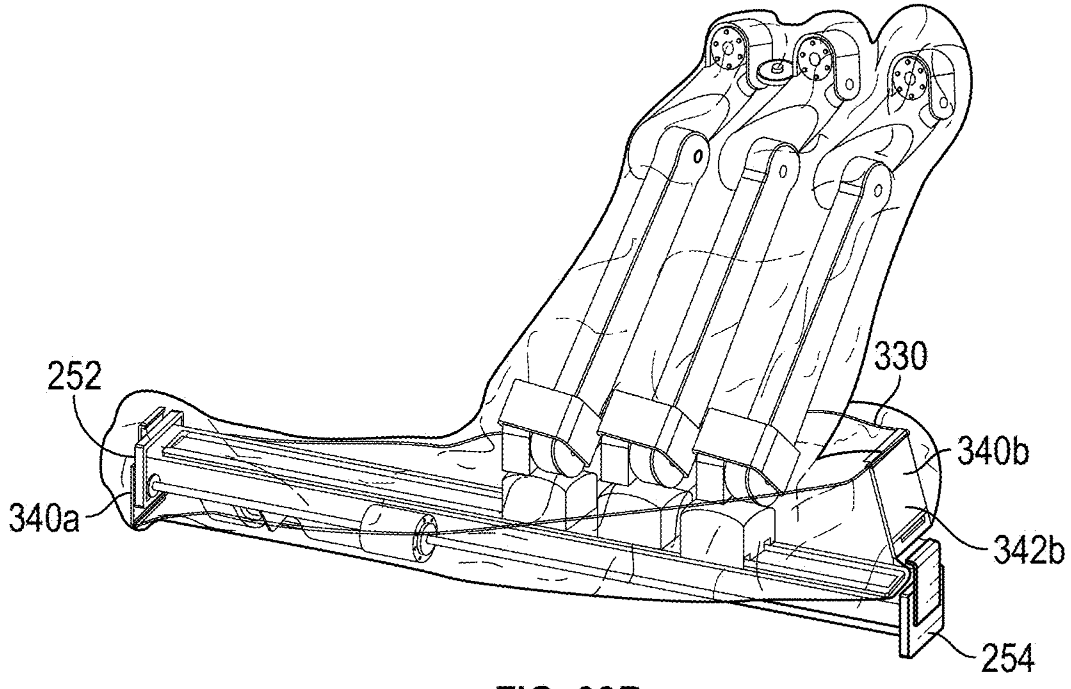
FIG. 38B illustrates the first end of the adjustable arm support draped.
Figure 38C:
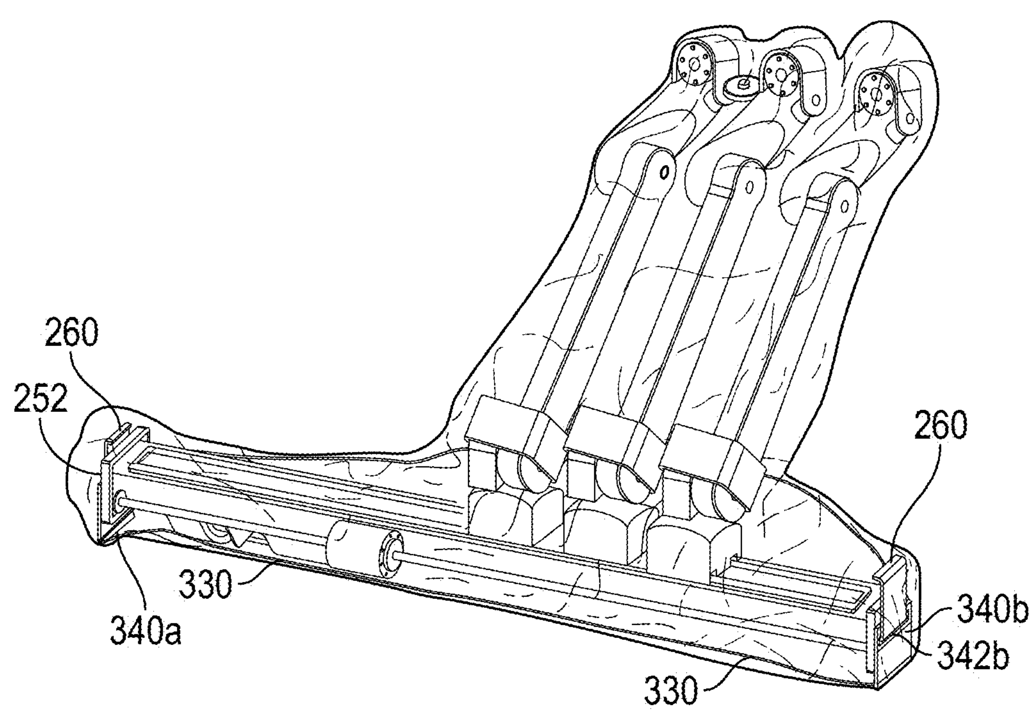
FIG. 38C illustrates the first and second ends of the adjustable arm support draped.

FIG. 38A illustrates both ends 252, 254 of the adjustable arm support 250 undraped. FIG. 38B illustrates the first end 252 of the adjustable arm support 250 draped. The first attachment component 340*a* is attached to the first latch 260*a* on the first end 252 of the adjustable arm support 250. FIG. 38C illustrates the first and second ends 252, 254 of the adjustable arm support 250 draped. The first attachment 340*a* is attached to the first latch 260*a* of the first end 252 of the adjustable arm support 250 and the second attachment 340*b* is attached to the second latch 260*b* on the second end 254 of the adjustable arm support 250.

Figure 39A:
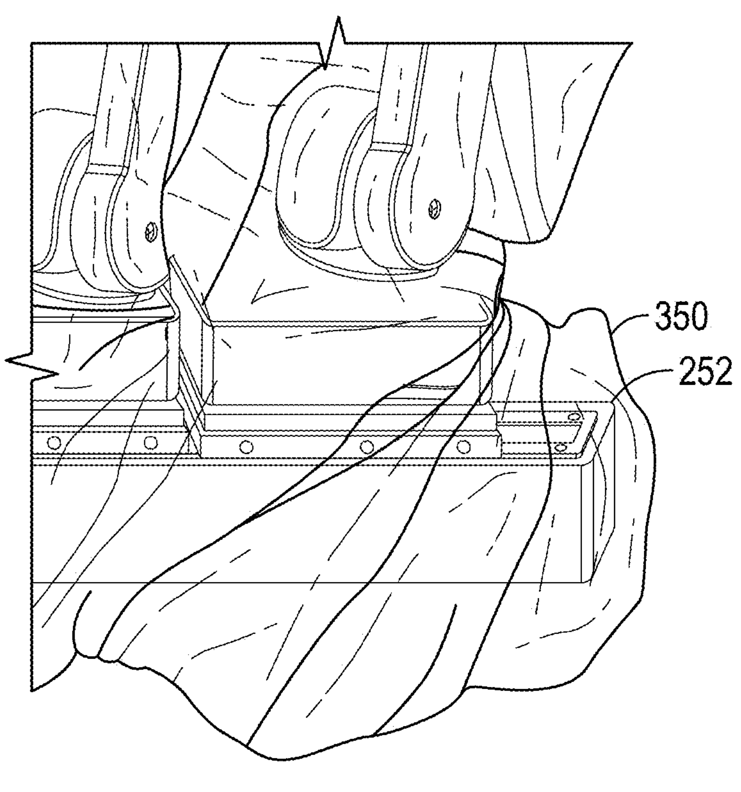
FIG. 39A illustrates a draped adjustable arm support without a latch.
Figure 39B:
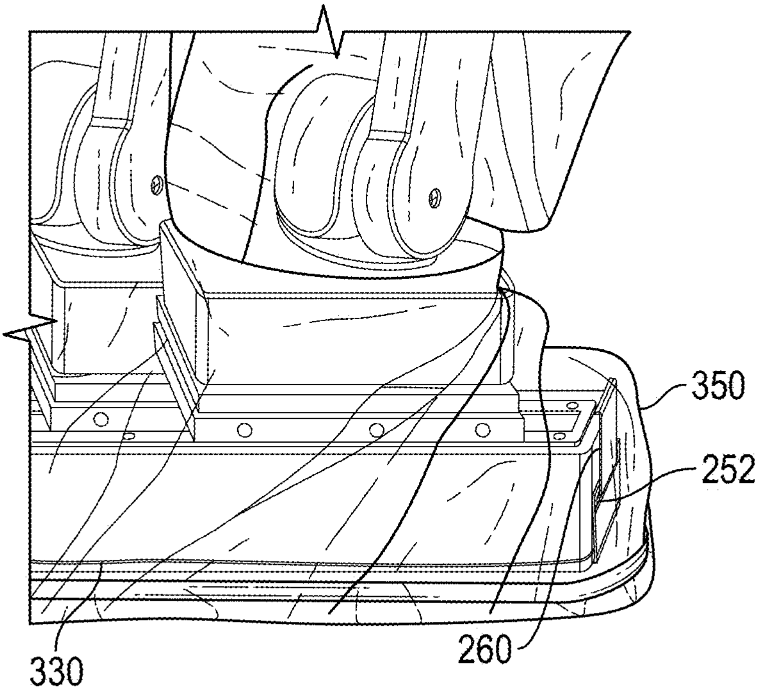
FIG. 39B illustrates the drape gathered on the latch of the adjustable arm support.

Additionally, another benefit of the latch or bumper 260 is that the drape material of the drape portion 350 can be gathered and collected, such that it is prevented from sliding off the end of the adjustable arm support 250. FIG. 39A illustrates a draped adjustable arm support 250 without a latch 260. FIG. 39B illustrates the drape 300 gathered on the latch 260 of the adjustable arm support 250. In addition, another advantage of adding a latch or bumper 260 to the adjustable arm support 250 is that the drape material is collected and prevented from sliding off the end of the adjustable arm support 250.

Figure 40A:
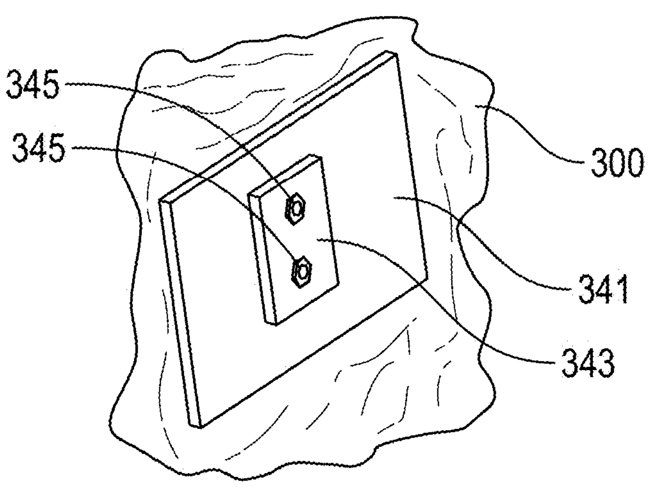
FIG. 40A illustrates another example attachment component.

FIG. 40A illustrates an alternative attachment component 341. The alternative attachment component 341 can be a card with a portion 343 which includes one or more magnets 345. The drape 300 can be attached to the alternative attachment component 341. In some examples, the drape 300 can be positioned between the card and the portion 343 including the one or more magnets 345. In some examples, the drape 300 can be attached to the card 341 on the opposite surface from the portion 343 including one or more magnets 345.

Figure 40B:
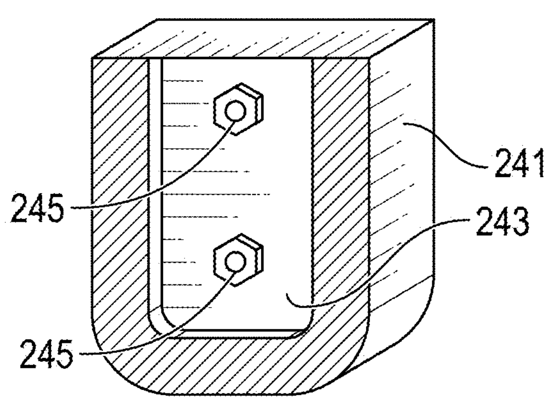
FIG. 40B illustrates another example end of an adjustable arm support.

FIG. 40B illustrates an alternative end 241 of the adjustable arm support 250. The alternative end 241 may have a recess 243 that is shaped to receive the portion 343 of the alternative attachment component 341. The alternative end 241 can have one or more magnets 245 positioned within the recess 243 of the alternative end 241.

Figure 40C:
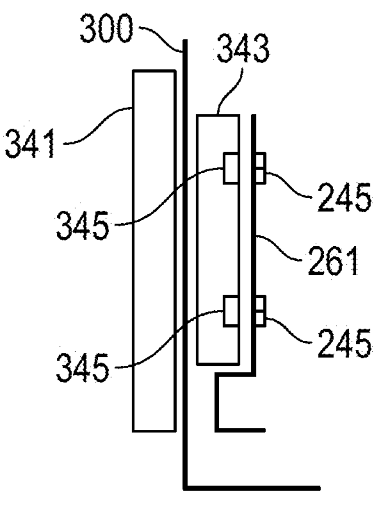
FIG. 40C illustrates the attachment component of FIG. 40A attached to the end of the adjustable arm support of FIG. 40B.

FIG. 40C illustrates the alternative attachment component of FIG. 40A on the alternative end of the adjustable arm support of FIG. 40B.

As shown, the recess 243 can receive the portion 343 of the alternative attachment component 341. The magnets 345 of the portion 343 of the alternative attachment component 341 engages with the magnets 245 of the end 241 of the adjustable arm support. The attachment component 341 can include a magnet 345 that, in use, interacts with a magnet 245 of the adjustable arm support 250.

Figure 41A:
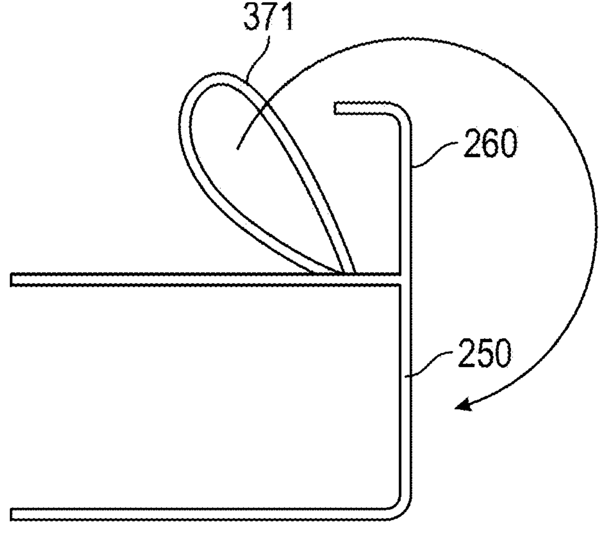
FIG. 41A illustrates yet another example attachment component.
Figure 41B:
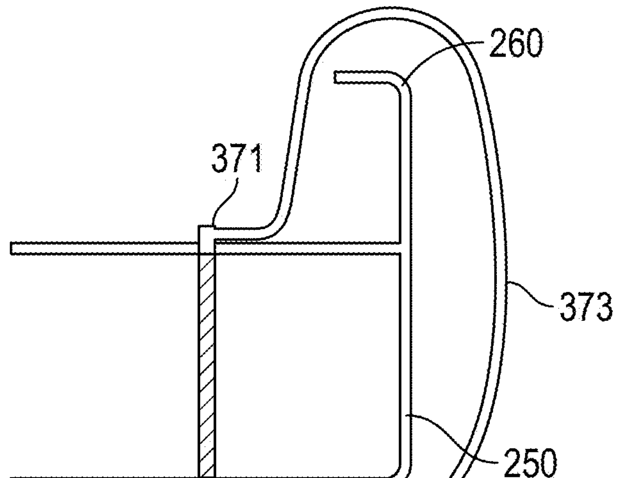
FIG. 41B illustrates the attachment component of FIG. 41A attached to an end of an adjustable arm support.

FIG. 41A illustrates an alternative attachment component 371. The alternative attachment component 371 may be a loop made of an adhesive (such as a wire tape) or an elastic that is wrapped around the adjustable arm support 250 that hooks over the latch or bumper 260. FIG. 41B illustrates the alternative attachment component of FIG. 41A attached to the end of the adjustable arm support 250. As shown in FIG. 41B, when the loop of the alternative attachment component 371 is placed around the adjustable arm support 250, the drape end 373 can be positioned around the end of the adjustable arm support 250.

In some examples, the attachment component can include a cap connected to the drape, the cap can be shaped and configured to fit over an end of the adjustable arm support. The cap may be fastened to the end of the adjustable arm support, such as by friction fit or with one or more fasteners or clamps.

iv. Sterile Adapter

Figure 42A:
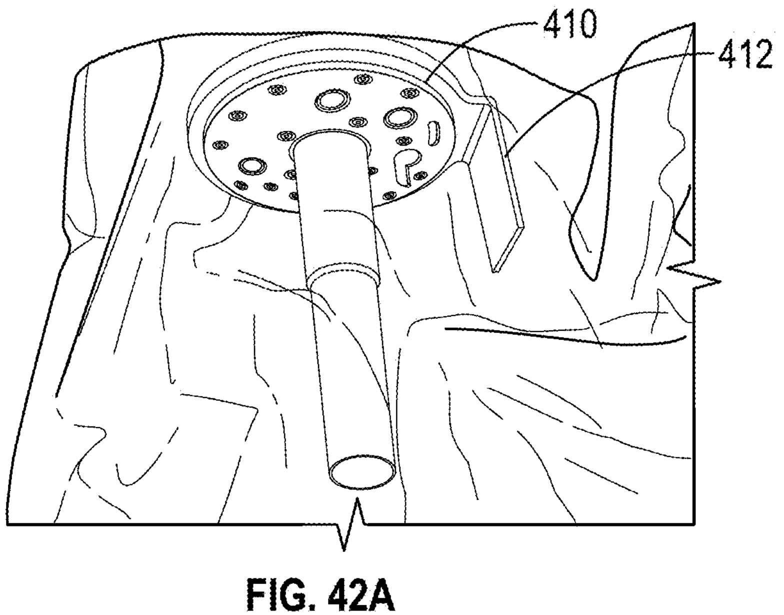
FIGS. 42A-42B illustrate an example sterile adapter connected to the drape.
Figure 42B:
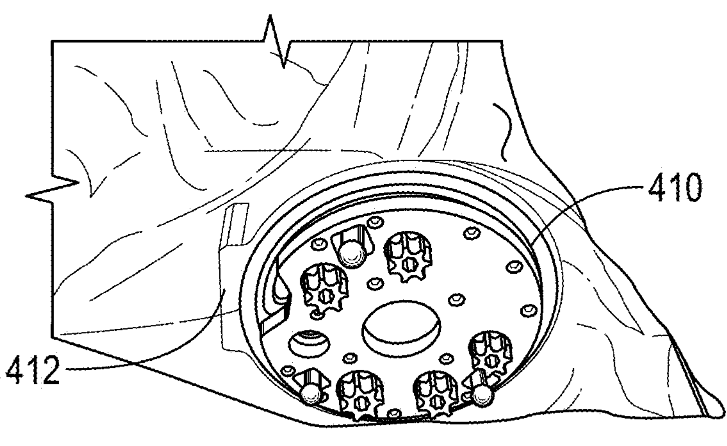

FIGS. 42A-42B illustrate a sterile adapter 410 connected to the drape 300. The drape 300 can include a distal attachment assembly to connect the sterile adapter 410 to the robotic arm 210. Specifically, the sterile adapter 410 can be attached to a distal end of the robotic arm 210. The distal attachment assembly can include a first component 412 and second component 414 to couple to a sterile adapter 410. The sterile adapter 410 is coupled to an instrument drive mechanism 222 of a respective robotic arm 210. The first component 412 can be a frame connected to the drape 300 and configured to receive the sterile adapter 410. The first end of the sterile adapter can be positioned within the first component 412.

The second component 414 can be a tube or component defining or forming an opening or aperture through the drape 300.

As described herein, the distal end 216 of each robotic arm 210 can include an instrument drive mechanism 222. The instrument drive mechanism 222 can include a central bore to receive and engage with a plurality of robotic medical instruments (not shown). In some examples, a shaft of a robotic medical instrument can pass through the central bore of the instrument drive mechanism 222. Once the tubular sleeve 310 is draped over the robotic arm 210 as described herein, the shaft of the sterile adapter 410 can be positioned within the central bore of the instrument drive mechanism 222. The second end of the shaft of the sterile adapter 410 can then be attached to the second component 414.

The second component 414 may be configured to allow an instrument shaft to pass therethrough. The second component 414 can be positioned on a separate position of the drape 300 from the position of the first component 412 of the drape 300.

Figure 43A:
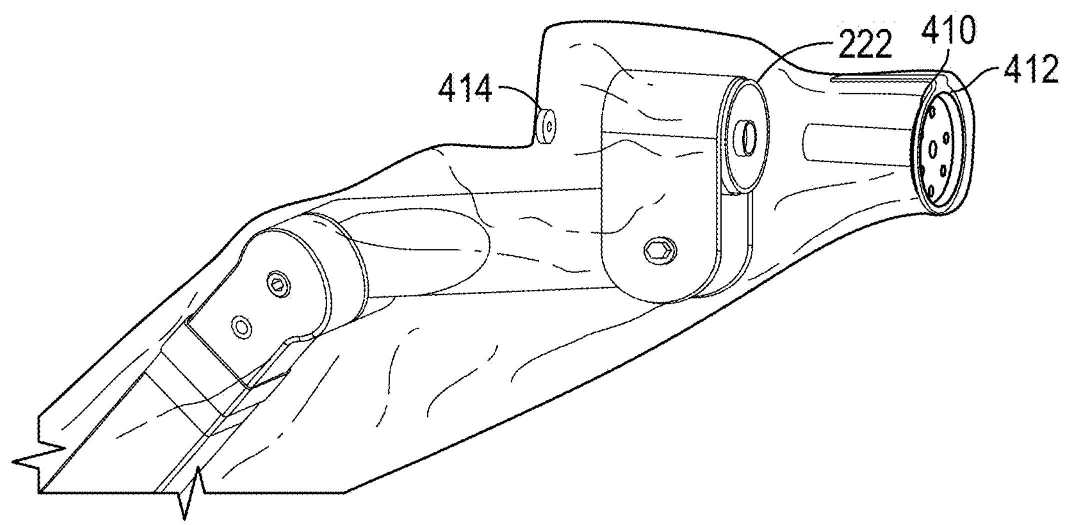
FIG. 43A illustrates a sterile adapter aligned with a distal end of a robotic arm.

FIG. 43A illustrates the sterile adapter aligned with the instrument drive mechanism 222 at the distal end 216 of the robotic arm 210. With the first component 412 and the second component 414 of the distal attachment assembly positioned at two different locations of the drape 300, the instrument shaft can enter through the first component 412 pass through the sterile adapter 410 and exit through the second component 414. As shown in FIG. 43A, an instrument shaft can pass through and linearly translate through the draped instrument drive mechanism 222.

Figure 43B:
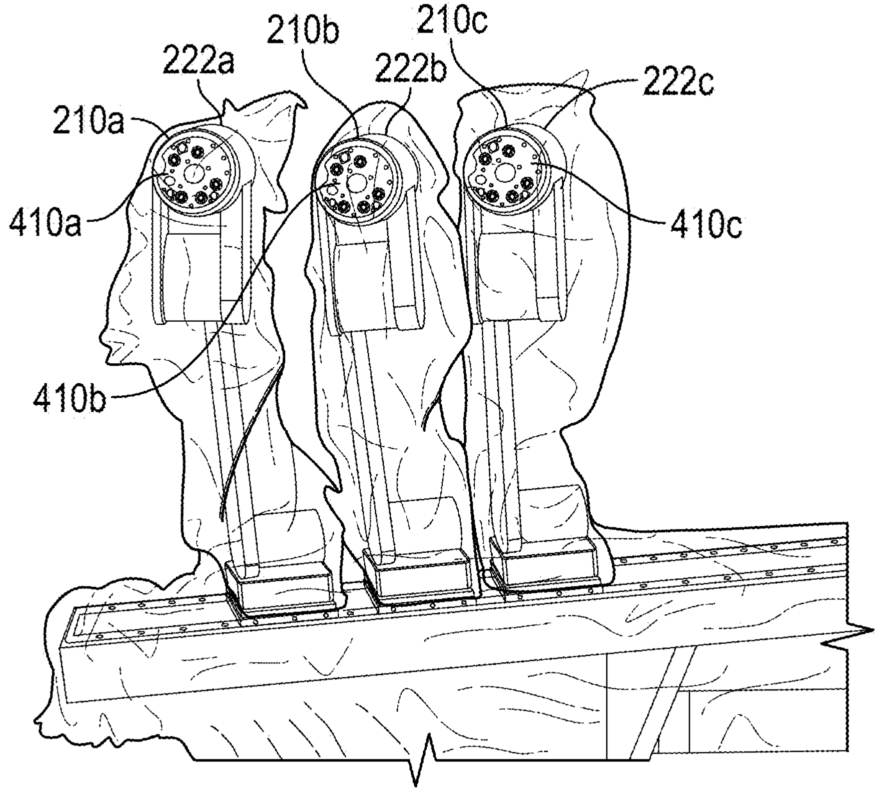
FIG. 43B illustrates sterile adapters positioned within each distal end of the robotic arm.

FIG. 43B illustrates the sterile adapters 410 positioned within each instrument drive mechanisms 222 of the robotic arms 210*a*, 210*b*, 210*c*.

3. Implementing Systems and Terminology

Implementations disclosed herein provide systems, methods and apparatuses related to drapes for a robotic surgical system.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The specific computer-implemented functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical system, comprising:

a first robotic arm comprising a first proximal end, a first distal end, a first series of links between the first proximal end and the first distal end, and a first series of joints connecting the first series of links, the first robotic arm being configured to maintain a drape pose in which the first distal end and the first series of links are directed upwards and positioned above the first proximal end;

a second robotic arm comprising a second proximal end, a second distal end, a second series of links between the second proximal end and the second distal end, and a second series of joints connecting the second series of links, the second robotic arm being configured to maintain a drape pose in which the second distal end and the second series of links are directed upwards and positioned above the second proximal end;

a first tube including a first pocket for receiving the first robotic arm, the first tube having a proximal end, a distal end, a drape material extending between the proximal end and the distal end of the first tube, and a first cuff positioned at the proximal end of the first tube, the first cuff being formed of a stiffer material than the drape material of the first tube, the first tube configured to be downwardly draped over the first robotic arm while the first robotic arm is in the drape pose, the first cuff being configured to hold open the proximal end of the first tube to receive the first robotic arm; and a second tube including a second pocket for receiving the second robotic arm, the second tube having a proximal end, a distal end, a drape material extending between the proximal end and the distal end of the second tube, and a second cuff positioned at the proximal end of the second tube, the second cuff being formed of a stiffer material than the drape material of the second tube, the second tube configured to be downwardly draped over the second robotic arm while the second robotic arm is in the drape pose, the second cuff being configured to hold open the proximal end of the second tube to receive the second robotic arm.

2. The robotic surgical system of claim 1, further comprising:

a drape portion coupled to the first and second tubes, the drape portion configured to be draped over an arm support coupled to the first and second robotic arms.

3. The robotic surgical system of claim 2, further comprising one or more cards attached to the drape portion.

4. The robotic surgical system of claim 1, further comprising a third robotic arm and a third tube, the third tube including a third pocket for receiving a third robotic arm, the third robotic arm comprising a third series of links connected by a third series of joints, the third tube configured to be downwardly draped over the third robotic arm.

5. The robotic surgical system of claim 1, wherein the first cuff and the second cuff are formed of polyethylene or polystyrene.

6. The robotic surgical system of claim 1, wherein the drape material of the first tube is folded over the first cuff repeatedly in a telescoping or pleated manner, and wherein the drape material of the second tube is folded over the second cuff repeatedly in a telescoping or pleated manner.

7. The robotic surgical system of claim 1, wherein a portion of the first tube intermediate the proximal end and the distal end of the first tube has substantially the same diameter as the first cuff, and wherein a portion of the second tube intermediate the proximal end and the distal end of the second tube has substantially the same diameter as the second cuff.

8. The robotic surgical system of claim 1, wherein the drape material of the first tube and the drape material of the second tube are formed of an elastomeric material.

9. The robotic surgical system of claim 1, wherein the first and second tubes are configured to be unfolded downwardly over the first and second robotic arms simultaneously.

10. The robotic surgical system of claim 1, further comprising:

two or more handholds positioned at opposing sides of an assembly that comprises the first and second tubes.

11. The robotic surgical system of claim 1, wherein the first robotic arm and the second robotic arm are configured to position the first distal end and the second distal end at a same height as each other while in the drape pose.

12. The robotic surgical system of claim 1, wherein the first and second tubes are configured to be unfolded downwardly over the first and second robotic arms consecutively.

13. A robotic surgical system, comprising:

a first robotic arm comprising a first proximal end, a first distal end, and a first series of links connected by a first series of joints;

a second robotic arm comprising a second proximal end, a second distal end, and a second series of links connected by a second series of joints;

one or more processors;

a computer readable medium storing instructions that, when executed by the one or more processors, cause the first robotic arm and the second robotic arm to be positioned in a drape pose in which the first series of links and the first distal end are directed upwards above the first proximal end and the second series of links and the second distal end are directed upwards above the second proximal end;

a first tube-shaped drape including a first pocket for receiving the first robotic arm, the first tube-shaped drape having a proximal end, a distal end, a first sleeve portion extending between the proximal end and the distal end of the first tube-shaped drape, and a first cuff positioned at the proximal end of the first tube-shaped drape, the first cuff being stiffer than the first sleeve portion, the first tube-shaped drape configured to be downwardly draped over the first robotic arm while the first robotic arm is in the drape pose, the first cuff being configured to hold open the proximal end of the first tube-shaped drape to receive the first robotic arm; and a second tube-shaped drape including a second pocket for receiving the second robotic arm, the second tube-shaped drape having a proximal end, a distal end, a second sleeve portion extending between the proximal end and the distal end of the second tube-shaped drape, and a second cuff positioned at the proximal end of the second tube-shaped drape, the second cuff being stiffer than the second sleeve portion, the second tube-shaped drape configured to be downwardly draped over the second robotic arm while the second robotic arm is in the drape pose, the second cuff being configured to hold open the proximal end of the second tube-shaped drape to receive the second robotic arm.

14. The robotic surgical system of claim 13, further comprising:

an arm support coupled to the first and second robotic arms; and a drape portion coupled to the first and second tube-shaped drapes, the drape portion configured to be draped over the arm support.

15. The robotic surgical system of claim 13, wherein:

the first and second pockets are configured to be aligned with the first and second robotic arms when the first and second robotic arms are in the drape pose.

16. A method of draping a robotic surgical system, the robotic surgical system comprising a first robotic arm and a second robotic arm, the first robotic arm comprising a first proximal end, a first distal end, a first series of links between the first proximal end and the first distal end, and a first series of joints connecting the first series of links, the second robotic arm comprising a second proximal end, a second distal end, a second series of links between the second proximal end and the second distal end, and a second series of joints connecting the second series of links, the method comprising:

placing the robotic surgical system in a drape pose in which:

each link in the first series of links extends in an upwards direction above the first proximal end of the first robotic arm, each link in the second series of links extends in an upwards direction above the second proximal end of the second robotic arm, and the second series of links of the second robotic arm extends parallel to the first series of links of the first robotic arm;

downwardly draping a first tube-shaped drape over the first robotic arm of the robotic surgical system while the robotic surgical system is in the drape pose, the first tube-shaped drape comprising a first pocket for receiving the first robotic arm, the first tube-shaped drape having a proximal end, a distal end, a first sleeve portion extending between the proximal end and the distal end of the first tube-shaped drape, and a first cuff positioned at the proximal end of the first tube-shaped drape, the first cuff being stiffer than the first sleeve portion, the first cuff holding open the proximal end of the first tube-shaped drape as the first tube-shaped drape receives the first robotic arm; and downwardly draping a second tube-shaped drape over the second robotic arm of the robotic surgical system while the robotic surgical system is in the drape pose, the second tube-shaped drape comprising a second pocket for receiving the second robotic arm, the second tube-shaped drape having a proximal end, a distal end, a second sleeve portion extending between the proximal end and the distal end of the second tube-shaped drape, and a second cuff positioned at the proximal end of the second tube-shaped drape, the second cuff being stiffer than the second sleeve portion, the second cuff holding open the proximal end of the second tube-shaped drape as the second tube-shaped drape receives the second robotic arm.

17. The method of claim 16, wherein the first tube-shaped drape and the second tube-shaped drape are downwardly draped over the first and second robotic arms simultaneously.

18. The method of claim 16, wherein the first tube-shaped drape and the second tube-shaped drape are downwardly draped over the first and second robotic arms consecutively.

* * * * *